(12) United States Patent
Cicchello et al.

(10) Patent No.: US 11,672,895 B2
(45) Date of Patent: Jun. 13, 2023

(54) METHOD FOR PERITONEAL DIALYSIS AND EXTRACORPOREAL BLOOD TREATMENTS

(71) Applicants: Baxter International Inc., Deerfield, IL (US); Baxter Healthcare SA, Glattpark (CH)

(72) Inventors: Gino Cicchello, Vernon Hills, IL (US); Christian Bernard, McHenry, IL (US); Robert W. Childers, New Port Richey, FL (US); Anthony Simiele, Clearwater, FL (US)

(73) Assignees: Baxter International Inc., Deerfield, IL (US); Baxter Healthcare SA, Glattpark (CH)

(*) Notice: Subject to any disclaimer, the term of this patent is extended or adjusted under 35 U.S.C. 154(b) by 71 days.

(21) Appl. No.: 17/360,717

(22) Filed: Jun. 28, 2021

(65) Prior Publication Data

US 2021/0322660 A1 Oct. 21, 2021

Related U.S. Application Data

(63) Continuation of application No. 15/826,978, filed on Nov. 30, 2017, now Pat. No. 11,045,595, which is a
(Continued)

(51) Int. Cl.
*A61M 1/28* (2006.01)
*A61M 1/16* (2006.01)
(Continued)

(52) U.S. Cl.
CPC .............. *A61M 1/282* (2014.02); *A61M 1/16* (2013.01); *A61M 1/1601* (2014.02);
(Continued)

(58) Field of Classification Search
CPC .... A61M 1/16; A61M 1/1601; A61M 1/1603; A61M 1/1611; A61M 1/1639;
(Continued)

(56) References Cited

U.S. PATENT DOCUMENTS

| 3,707,967 A | 1/1973 | Kitrilakis et al. |
| 3,712,474 A | 1/1973 | Martinez |

(Continued)

FOREIGN PATENT DOCUMENTS

| DE | 4020235 | 1/1992 |
| EP | 0694312 | 1/1996 |

(Continued)

OTHER PUBLICATIONS

Search Report for related International Patent Application No. PCT/US2016/018277 dated Apr. 25, 2016. 5 pages.
(Continued)

*Primary Examiner* — Dirk R Bass
(74) *Attorney, Agent, or Firm* — K&L Gates LLP

(57) ABSTRACT

A dialysis method to enable a patient to undergo both peritoneal dialysis and extracorporeal blood treatments is disclosed. The method includes determining, via a base unit controller, whether a peritoneal dialysis treatment or an extracorporeal blood treatment is to be performed. If the peritoneal dialysis treatment is to be performed, the method includes operating first software instructions that cause a base unit to use a first fluid stored in a fluid container. If the extracorporeal blood treatment is to be performed, the method includes operating second software instructions that cause the base unit to use a second, different fluid from an online source and selectively move the second, different fluid to a blood treatment unit for use in the extracorporeal
(Continued)

blood treatment. The blood treatment unit is operable with the base unit to perform the extracorporeal blood treatment on a patient.

16 Claims, 29 Drawing Sheets

Related U.S. Application Data continuation of application No. 15/353,077, filed on Nov. 16, 2016, now Pat. No. 10,434,237, which is a continuation of application No. 14/980,935, filed on Dec. 28, 2015, now Pat. No. 9,744,284, which is a continuation of application No. 14/010,102, filed on Aug. 26, 2013, now Pat. No. 9,227,003, which is a continuation of application No. 13/969,744, filed on Aug. 19, 2013, now abandoned, which is a continuation of application No. 11/773,634, filed on Jul. 5, 2007, now Pat. No. 8,512,553.

(51) Int. Cl.
*A61M 1/30* (2006.01)
*A61M 1/34* (2006.01)
*G16H 20/40* (2018.01)
*A61M 60/279* (2021.01)

(52) U.S. Cl.
CPC .......... *A61M 1/1603* (2014.02); *A61M 1/168* (2013.01); *A61M 1/169* (2013.01); *A61M 1/1611* (2014.02); *A61M 1/1639* (2014.02); *A61M 1/1682* (2014.02); *A61M 1/1686* (2013.01); *A61M 1/1688* (2014.02); *A61M 1/1694* (2013.01); *A61M 1/1696* (2013.01); *A61M 1/28* (2013.01); *A61M 1/284* (2014.02); *A61M 1/288* (2014.02); *A61M 1/30* (2013.01); *A61M 1/34* (2013.01); *A61M 1/3417* (2014.02); *A61M 1/3427* (2014.02); *A61M 1/3431* (2014.02); *A61M 1/3444* (2014.02); *A61M 60/279* (2021.01); *G16H 20/40* (2018.01); *A61M 1/3437* (2014.02); *A61M 2205/12* (2013.01); *A61M 2205/128* (2013.01); *A61M 2205/3331* (2013.01); *A61M 2205/3344* (2013.01); *A61M 2205/3368* (2013.01); *A61M 2205/3379* (2013.01); *A61M 2205/50* (2013.01); *A61M 2205/502* (2013.01); *A61M 2210/1017* (2013.01)

(58) Field of Classification Search
CPC .. A61M 1/168; A61M 1/1682; A61M 1/1686; A61M 1/1688; A61M 1/169; A61M 1/1694; A61M 1/1696; A61M 1/28; A61M 1/282; A61M 1/284; A61M 1/288; A61M 1/30; A61M 1/34; A61M 1/3417; A61M 1/3427; A61M 1/3431; A61M 1/3437; A61M 1/3444; A61M 2205/12; A61M 2205/128; A61M 2205/3331; A61M 2205/3344; A61M 2205/3368; A61M 2205/3379; A61M 2205/50; A61M 2205/502; A61M 2210/1017; A61M 60/279; G16H 20/40
USPC ............ 210/645, 646, 109, 143, 195.2, 741; 604/4, 5, 34
See application file for complete search history.

(56) References Cited

U.S. PATENT DOCUMENTS

| | | |
|---|---|---|
| 3,734,298 A | 5/1973 | Riede et al. |
| 3,791,767 A | 2/1974 | Schill |
| 3,830,234 A | 8/1974 | Kopp |
| 3,837,496 A | 9/1974 | Hagstrom et al. |
| 3,841,491 A | 10/1974 | Hagstrom et al. |
| 3,857,785 A | 12/1974 | Martinez |
| RE29,346 E | 8/1977 | Kopp |
| 4,085,046 A | 4/1978 | Saporito, Jr. |
| 4,093,545 A | 6/1978 | Cullis |
| 4,094,775 A | 6/1978 | Mueller |
| 4,122,010 A | 10/1978 | Riede et al. |
| 4,140,633 A | 2/1979 | Goldhaber |
| 4,141,834 A | 2/1979 | Bellotti et al. |
| 4,142,974 A | 3/1979 | Bellotti et al. |
| 4,202,764 A | 5/1980 | Afflerbaugh et al. |
| 4,234,428 A | 11/1980 | Schnell |
| 4,235,231 A | 11/1980 | Schindler et al. |
| 4,240,408 A | 12/1980 | Schael |
| 4,252,651 A | 2/1981 | Soderstrom |
| 4,267,041 A | 5/1981 | Schael |
| 4,348,280 A | 9/1982 | George et al. |
| 4,353,368 A | 10/1982 | Slovak et al. |
| 4,443,333 A | 4/1984 | Mahurkar |
| 4,468,329 A | 8/1984 | Shaldon et al. |
| 4,479,762 A | 10/1984 | Bilstad et al. |
| 4,486,189 A | 12/1984 | Troutner et al. |
| 4,490,134 A | 12/1984 | Troutner |
| 4,514,295 A | 4/1985 | Mathieu et al. |
| 4,552,552 A | 11/1985 | Polaschegg |
| 4,560,472 A | 12/1985 | Granzow et al. |
| 4,585,436 A | 4/1986 | Davis et al. |
| 4,586,920 A | 5/1986 | Peabody |
| 4,596,550 A | 6/1986 | Troutner |
| 4,610,665 A | 9/1986 | Matsumoto et al. |
| 4,610,781 A | 9/1986 | Bilstad et al. |
| 4,618,343 A | 10/1986 | Polaschegg |
| 4,655,762 A | 4/1987 | Rogers |
| 4,683,053 A | 7/1987 | Polaschegg |
| 4,711,715 A | 12/1987 | Polaschegg |
| 4,718,890 A | 1/1988 | Peabody |
| 4,726,381 A | 2/1988 | Jones |
| 4,747,822 A | 5/1988 | Peabody |
| 4,765,339 A | 8/1988 | Jones |
| 4,828,543 A | 5/1989 | Weiss et al. |
| 4,935,125 A | 6/1990 | Era et al. |
| 4,940,455 A | 7/1990 | Guinn |
| 4,997,570 A | 3/1991 | Polaschegg |
| 5,004,459 A | 4/1991 | Peabody |
| 5,024,756 A | 6/1991 | Sternby |
| 5,141,493 A | 8/1992 | Jacobsen et al. |
| 5,173,125 A | 12/1992 | Felding |
| 5,211,913 A | 5/1993 | Hagiwara et al. |
| 5,334,139 A | 8/1994 | Jeppsson et al. |
| 5,342,527 A | 8/1994 | Chevallet et al. |
| 5,350,357 A | 9/1994 | Kamen et al. |
| 5,421,208 A | 6/1995 | Packard et al. |
| 5,421,823 A | 6/1995 | Packard et al. |
| 5,429,802 A | 7/1995 | Hagiwara et al. |
| 5,431,626 A | 7/1995 | Bryant et al. |
| 5,438,510 A | 8/1995 | Bryant et al. |
| 5,470,483 A | 11/1995 | Bene et al. |
| 5,474,683 A | 12/1995 | Bryant et al. |
| 5,498,338 A | 3/1996 | Kruger et al. |
| 5,507,723 A | 4/1996 | Keshaviah |
| 5,522,998 A | 6/1996 | Polaschegg |
| 5,529,685 A | 6/1996 | Irie et al. |
| 5,542,919 A | 8/1996 | Simon et al. |
| 5,582,794 A | 12/1996 | Hagiwara et al. |
| 5,609,770 A | 3/1997 | Zimmerman |
| 5,620,604 A | 4/1997 | Stone |
| 5,628,908 A | 5/1997 | Kamen et al. |
| 5,641,144 A | 6/1997 | Hendrickson et al. |
| 5,679,245 A | 10/1997 | Manica |
| 5,685,988 A | 11/1997 | Malchesky |
| 5,702,597 A | 12/1997 | Chevallet et al. |

(56) References Cited

U.S. PATENT DOCUMENTS

| | | |
|---|---|---|
| 5,722,947 A | 3/1998 | Jeppsson et al. |
| 5,725,776 A | 3/1998 | Kenley et al. |
| 5,755,968 A | 5/1998 | Stone |
| 5,782,796 A | 7/1998 | Din et al. |
| 5,843,474 A | 12/1998 | Williams |
| 5,938,634 A | 8/1999 | Packard |
| 5,984,891 A | 11/1999 | Keilman et al. |
| 5,989,423 A | 11/1999 | Kamen et al. |
| 6,042,784 A | 3/2000 | Wamsiedler et al. |
| 6,074,359 A | 6/2000 | Keshaviah et al. |
| 6,117,122 A | 9/2000 | Din et al. |
| 6,168,578 B1 | 1/2001 | Diamond |
| 6,196,992 B1 | 3/2001 | Keilman et al. |
| 6,254,567 B1 | 7/2001 | Treu et al. |
| 6,280,634 B1 | 8/2001 | Shah et al. |
| 6,284,131 B1 | 9/2001 | Hogard et al. |
| 6,458,275 B1 | 10/2002 | Shukla et al. |
| 6,488,647 B1 | 12/2002 | Miura et al. |
| 6,491,658 B1 | 12/2002 | Miura et al. |
| 6,558,347 B1 | 5/2003 | Jhuboo et al. |
| 6,595,944 B2 | 7/2003 | Balschat et al. |
| 6,595,948 B2 | 7/2003 | Suzuki et al. |
| 6,638,477 B1 | 10/2003 | Treu et al. |
| 6,645,166 B2 | 11/2003 | Scheunert et al. |
| 6,673,314 B1 | 1/2004 | Burbank et al. |
| 6,676,621 B1 | 1/2004 | Menninger |
| 6,758,975 B2 | 7/2004 | Peabody et al. |
| 6,775,577 B2 | 8/2004 | Crnkovich et al. |
| 6,830,553 B1 | 12/2004 | Burbank et al. |
| 6,868,309 B1 | 3/2005 | Begelman |
| 6,955,655 B2 | 10/2005 | Burbank et al. |
| 6,979,309 B2 | 12/2005 | Burbank et al. |
| 7,004,924 B1 | 2/2006 | Brugger et al. |
| 7,029,456 B2 | 4/2006 | Ware et al. |
| 7,112,273 B2 | 9/2006 | Weigel et al. |
| 7,115,107 B2 | 10/2006 | Delnevo et al. |
| 7,131,956 B1 | 11/2006 | Pirazzoli et al. |
| 7,153,286 B2 | 12/2006 | Busby et al. |
| 7,208,092 B2 | 4/2007 | Micheli |
| 7,214,312 B2 | 5/2007 | Brugger et al. |
| 7,223,336 B2 | 5/2007 | Tonelli et al. |
| 7,223,338 B2 | 5/2007 | Duchamp et al. |
| 7,226,538 B2 | 6/2007 | Brugger et al. |
| 7,232,418 B2 | 6/2007 | Neri et al. |
| 7,238,164 B2 | 7/2007 | Childers et al. |
| 7,247,146 B2 | 7/2007 | Tonelli et al. |
| 7,264,607 B2 | 9/2007 | Caleffi |
| 7,264,730 B2 | 9/2007 | Connell et al. |
| 7,267,658 B2 | 9/2007 | Treu et al. |
| 7,291,123 B2 | 11/2007 | Baraldi et al. |
| 7,291,269 B2 | 11/2007 | Chevallet et al. |
| 7,300,413 B2 | 11/2007 | Burbank et al. |
| 7,303,680 B2 | 12/2007 | Connell et al. |
| 7,314,554 B2 | 1/2008 | Delnevo et al. |
| 7,316,662 B2 | 1/2008 | Delnevo et al. |
| 7,318,892 B2 | 1/2008 | Connell et al. |
| 2003/0135152 A1 | 7/2003 | Kollar et al. |
| 2004/0019312 A1 | 1/2004 | Childers |
| 2005/0006296 A1 | 1/2005 | Sullivan et al. |
| 2005/0082210 A1 | 4/2005 | Favre |
| 2005/0131332 A1 | 6/2005 | Kelly et al. |
| 2005/0173344 A1 | 8/2005 | Bowman et al. |

FOREIGN PATENT DOCUMENTS

| | | |
|---|---|---|
| EP | 1314442 | 5/2003 |
| EP | 1623731 | 2/2006 |
| WO | 2006/011 009 | 2/2006 |
| WO | 2007138367 | 12/2007 |

OTHER PUBLICATIONS

Written Opinion for related International Patent Application No. PCT/US2016/018277 dated Apr. 25, 2016. 3 pages.
Website. "www.flipfins.com/index.php?page=about". Accessed Sep. 21, 2015. 2 pages.
Website. "www.flipfins.com/index.php?page=fins". Accessed Sep. 21, 2015. 1 page.
Website. "www.flipfins.com/index.php?page=fins&product=classic". Accessed Sep. 21, 2015. 2 pages.
Website. "www.flipfins.com/index.php?page=productss&product=navigator". Accessed Sep. 21, 2015. 2 pages.
Website. "www.flipfins.com/index.php?page=products&product=stealth". Accessed Sep. 21, 2015. 2 pages.
Website. "www.flipfins.com/index.php?page=products&product=stealthmax". Accessed Sep. 21, 2015. 2 pages.
Fukui Hara et al., "Review of Combination of Peritoneal Dialysis and Hemodialysis as a Modality of Treatment for Endstage Renal Disease", Therapeutic Apheresis and Dialysis, Aug. 2003, vol. 8(1), pp. 56-61.
Feng GH et al., "Combination of Hemofiltration and Peritoneal Dialysis in the Treatment of Severe Acute Pancreatitis", Chin J. Surg, Mar. 2004, vol. 42, No. 5, pp. 272-275.
Tadashi Torno et al., "The Effect of Peritoneal Rest in Combination Therapy of Peritoneal Dialysis and Hemodialysis Using the Cultured Human Peritoneal Mesothelial Cell Mode", The Japanese Society for Artificial Organs, Mar. 2005, vol. 8, pp. 125-129.
International Search Report and Written Opinion for PCT/US2008/068947 dated Apr. 16, 2009.
Non-Final Office Action issued in U.S. Appl. No. 13/828,731 dated Oct. 20, 2015 (10 pages).
Response to Non-Final Office Action issued in U.S. Appl. No. 13/828,731 dated Oct. 20, 2015, tiled on Jan. 20, 2016 (14 pages).
Extended Search Report for related European Patent Application No. 15198114.9 dated Apr. 1, 2016. 7 pages.

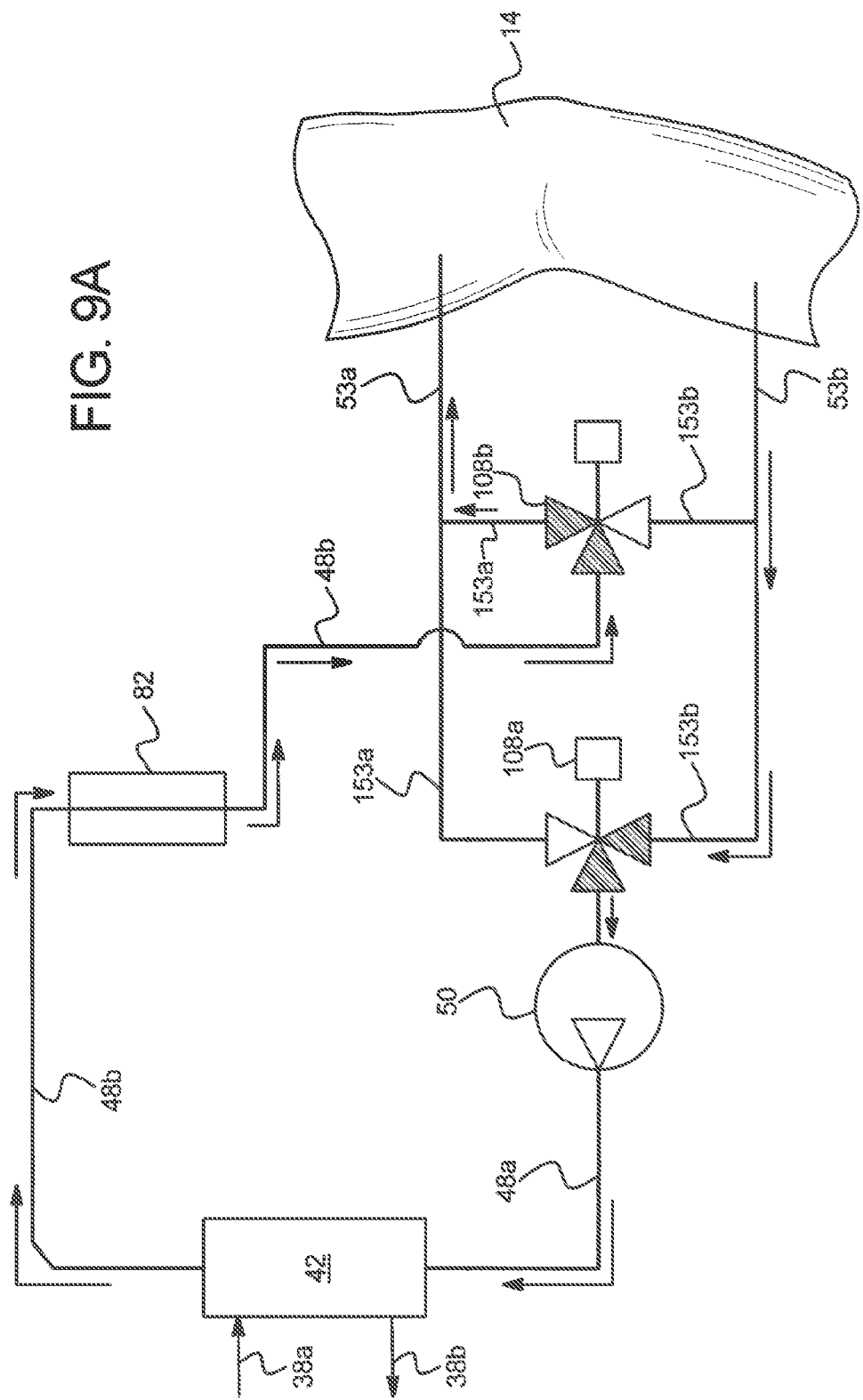

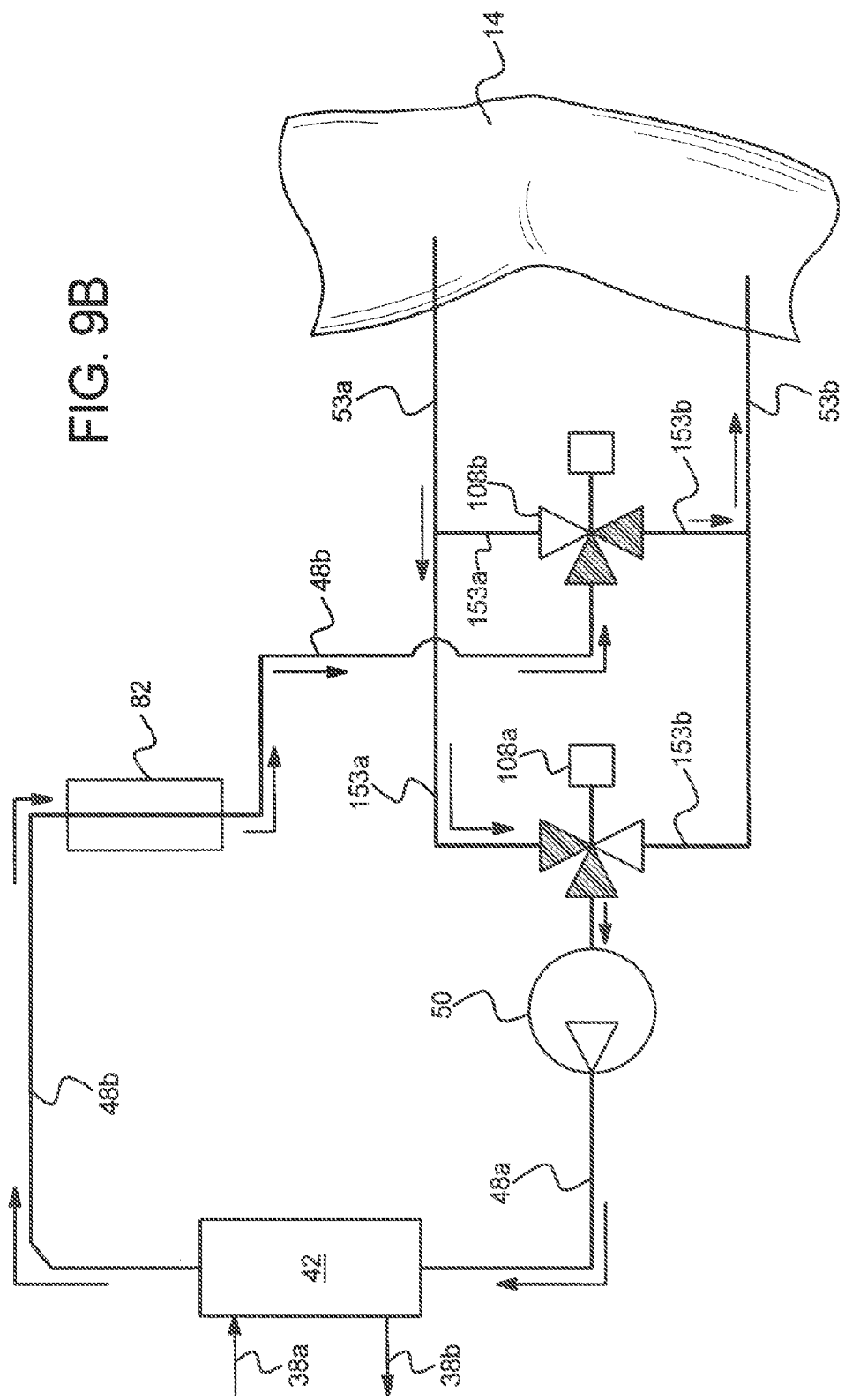

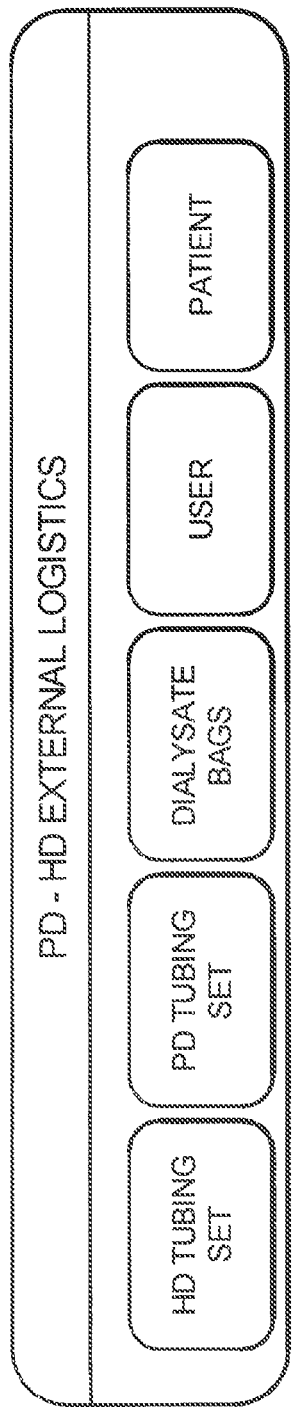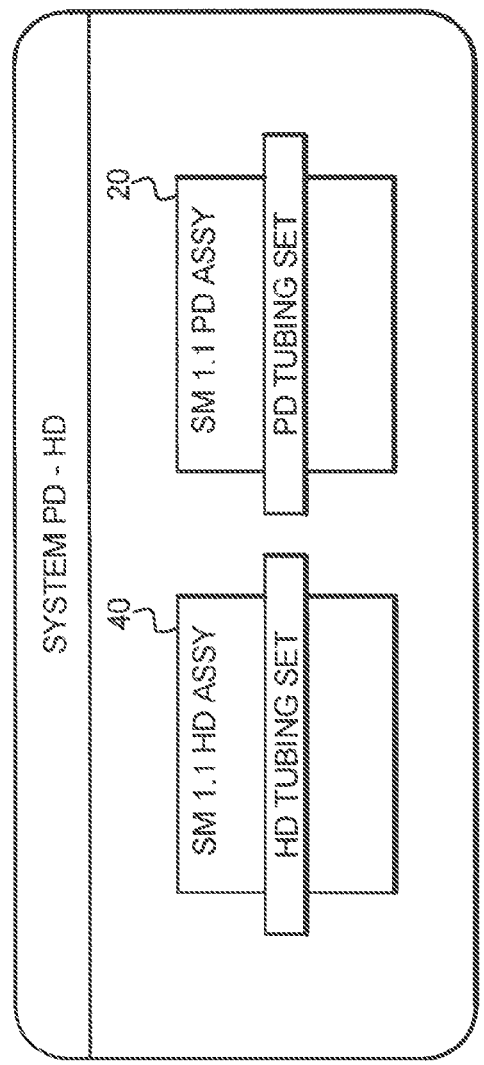

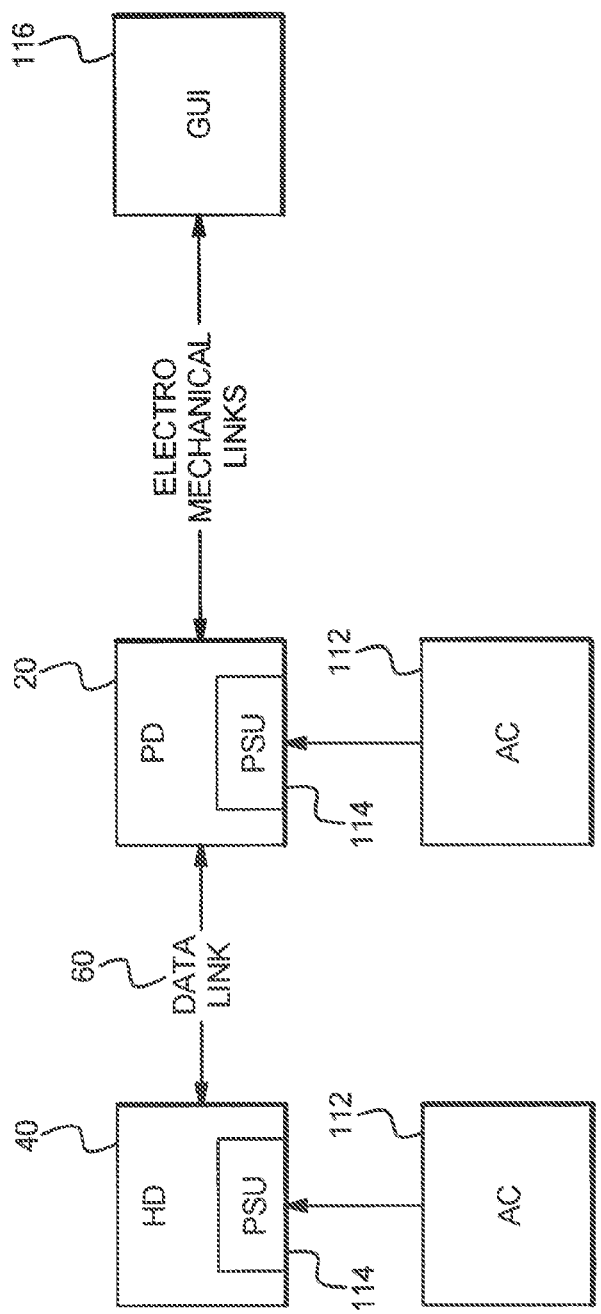

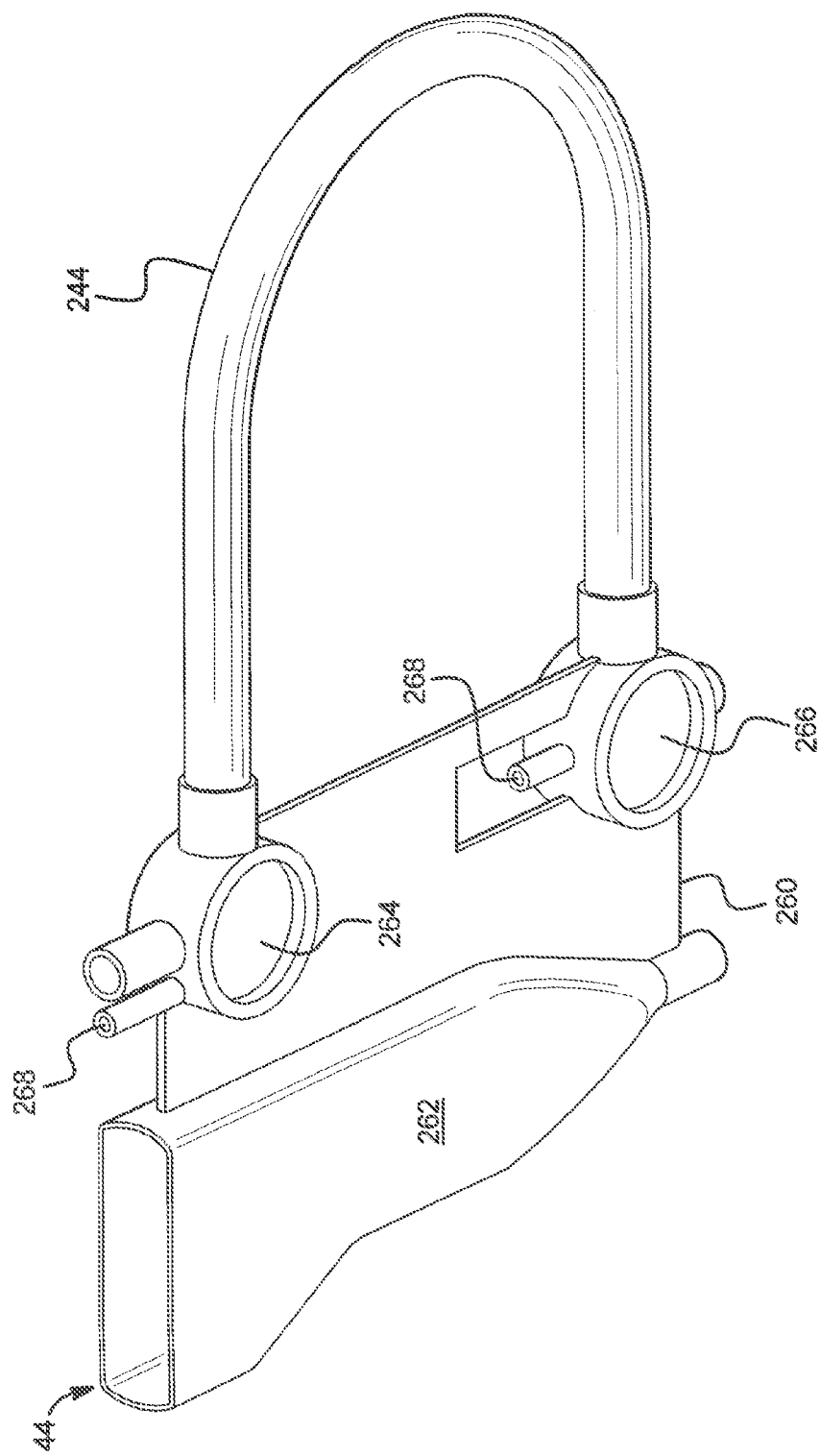

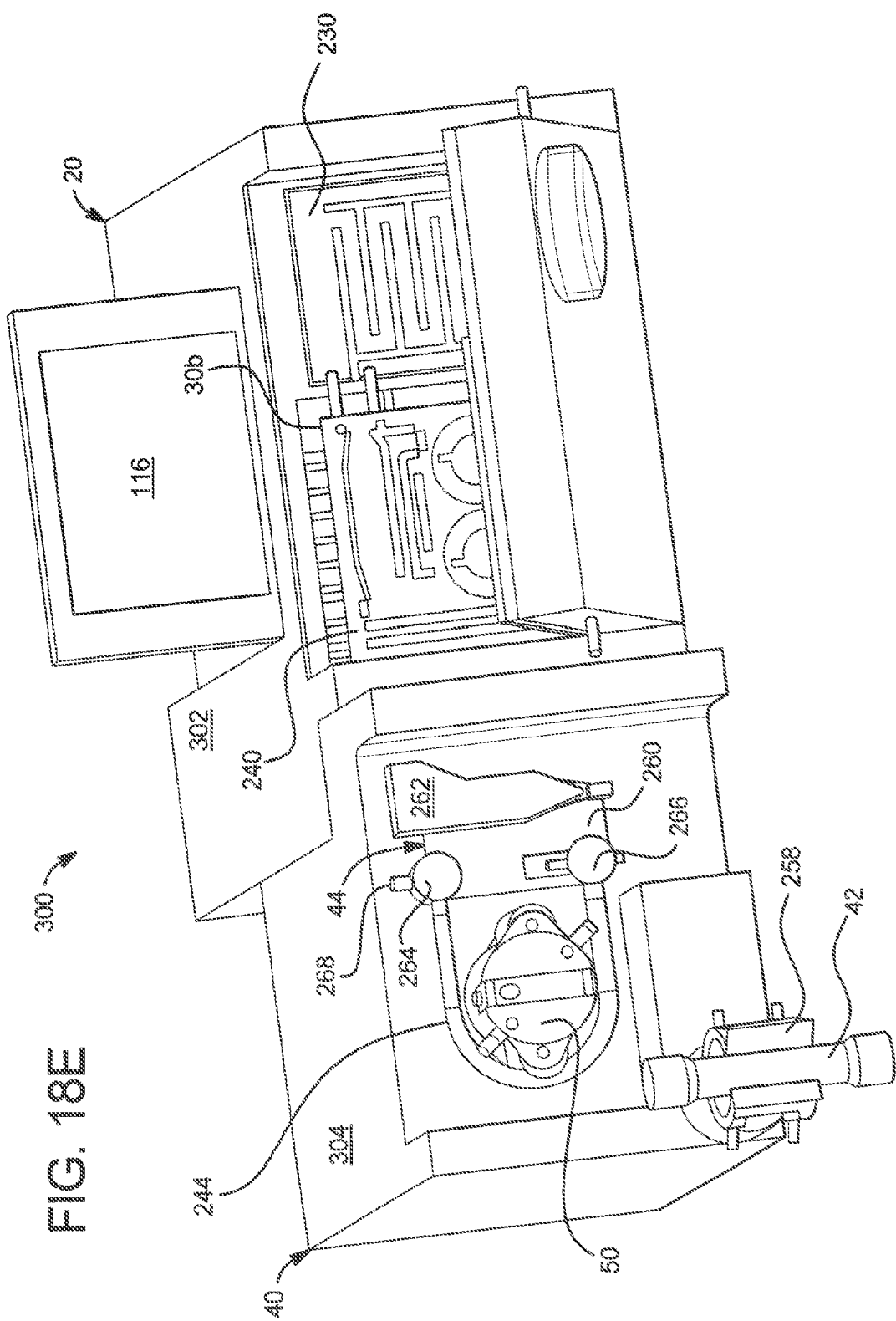

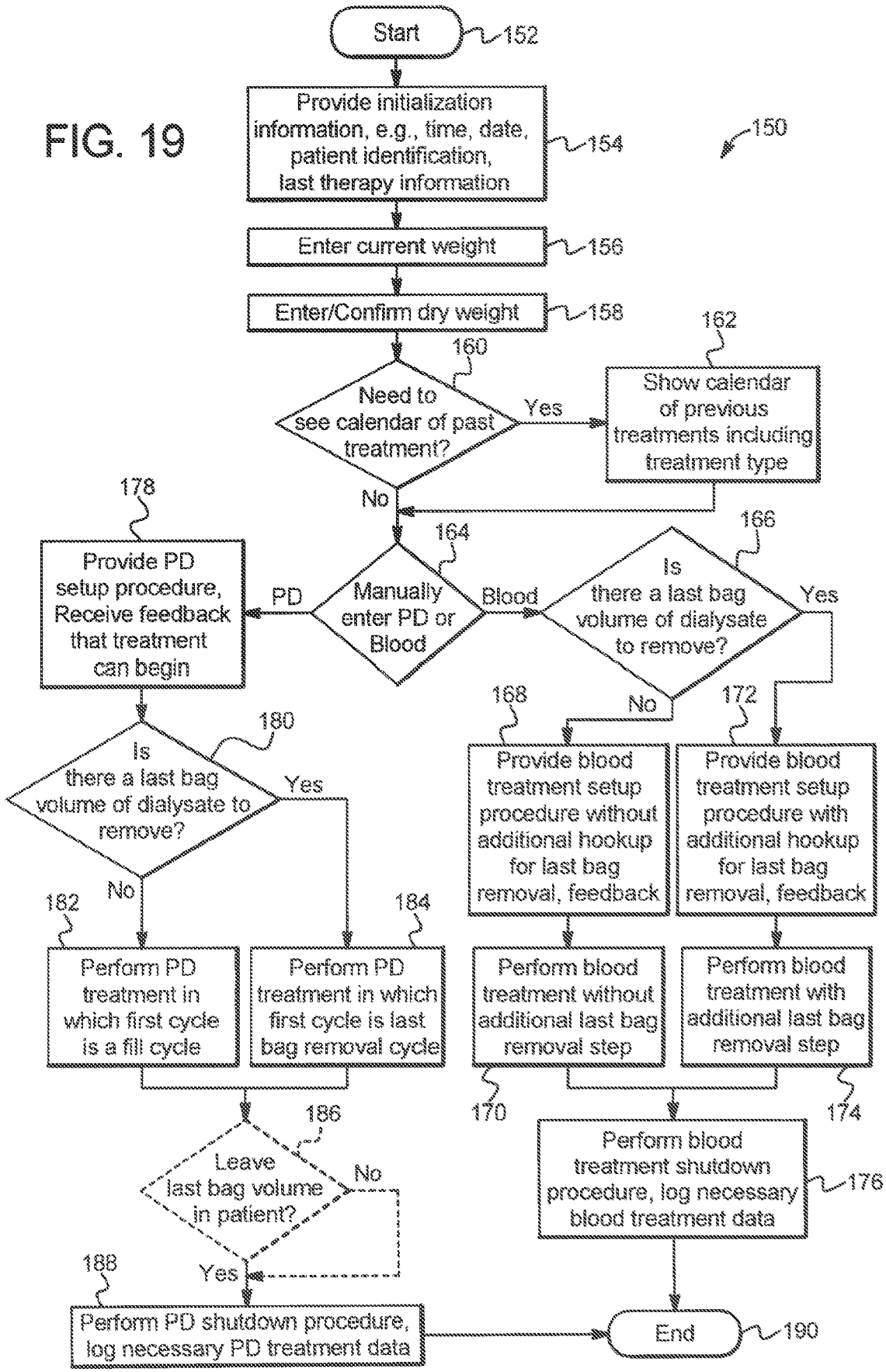

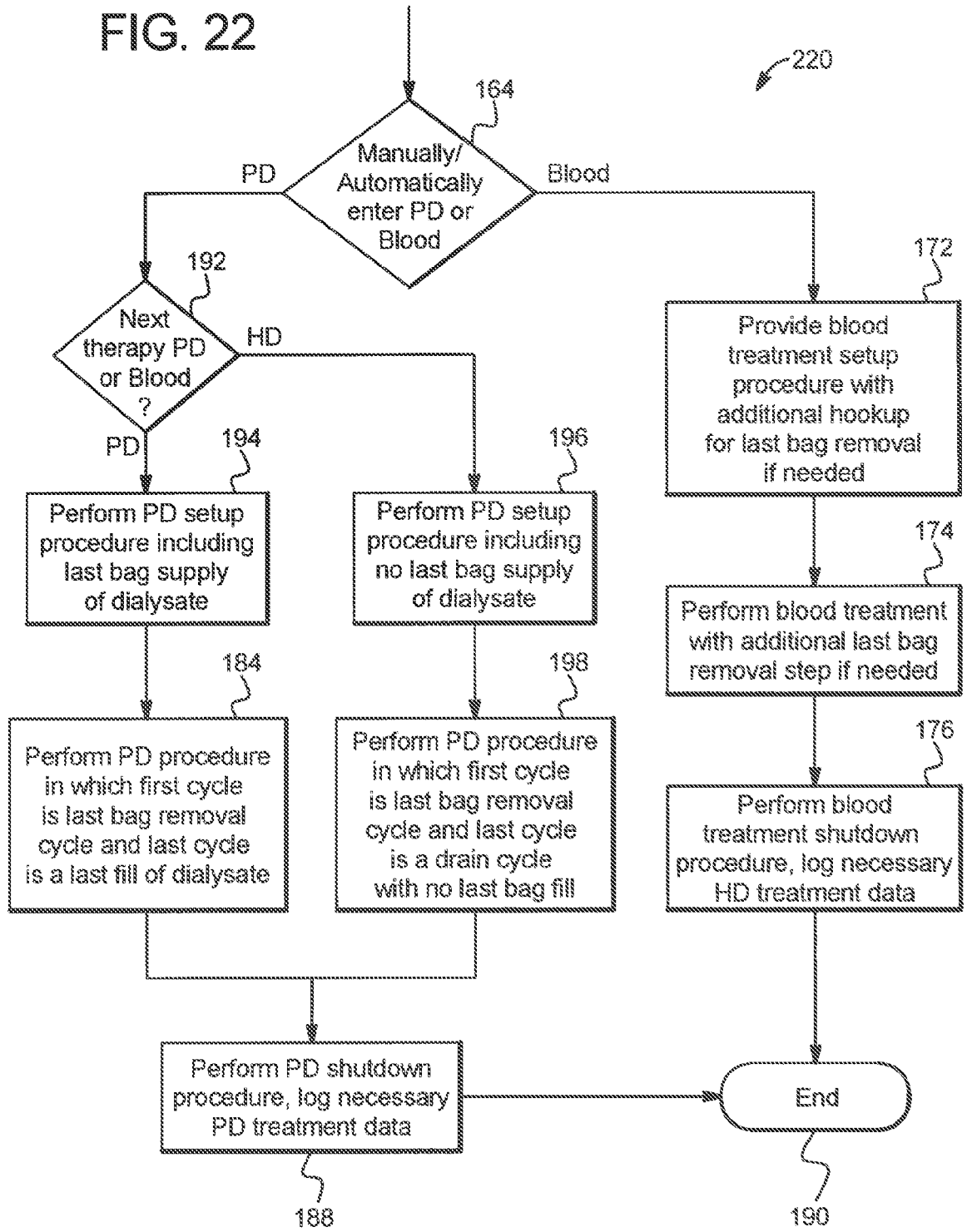

METHOD FOR PERITONEAL DIALYSIS AND EXTRACORPOREAL BLOOD TREATMENTS

PRIORITY

This application claims priority to and the benefit as a continuation application of U.S. application Ser. No. 15/826,978, filed Nov. 30, 2017, entitled, "System for Peritoneal Dialysis and Extracorporeal Blood Treatments", now U.S. Pat. No. 11,045,595, which is a continuation application of U.S. application Ser. No. 15/353,077, filed Nov. 16, 2016, entitled, "Hybrid Blood and Peritoneal Dialysis Treatment Systems and Methods", now U.S. Pat. No. 10,434,237, which is a continuation of U.S. application Ser. No. 14/980,935, filed Dec. 28, 2015, entitled, "Hybrid Blood and Peritoneal Dialysis Treatment Systems and Methods", now U.S. Pat. No. 9,744,284, which is a continuation of U.S. application Ser. No. 14/010,102, filed Aug. 26, 2013, entitled, "Hybrid Blood and Peritoneal Dialysis Treatment Systems and Methods", now U.S. Pat. No. 9,227,003, which is a continuation of U.S. patent application Ser. No. 13/969,744, filed Aug. 19, 2013, entitled "Dual, Single Needle Blood Treatment System and Method", which is a continuation of U.S. patent application Ser. No. 11/773,634, filed Jul. 5, 2007, entitled "Extracorporeal Dialysis Ready Peritoneal Dialysis Machine", now U.S. Pat. No. 8,512,553, the entire contents of each of which is incorporated herein by reference and relied upon.

BACKGROUND

The examples discussed below relate generally to medical fluid delivery. More particularly, the examples disclose systems, methods and apparatuses for the control of fluid flow in kidney failure treatment systems.

Due to various causes, a person's renal system can fail. Renal failure produces several physiological derangements. The balance of water, minerals and the excretion of daily metabolic load is no longer possible and toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving.

Hemodialysis and peritoneal dialysis are two types of dialysis therapies used commonly to treat loss of kidney function. A hemodialysis ("HD") treatment utilizes the patient's blood to remove waste, toxins and excess water from the patient. The patient is connected to a hemodialysis machine and the patient's blood is pumped through the machine. Catheters are inserted into the patient's veins and arteries so that blood can flow to and from the hemodialysis machine. The blood passes through a dialyzer of the machine, which removes waste, toxins and excess water from the blood. The cleaned blood is returned to the patient. A large amount of dialysate, for example about 80 to 120 liters, is consumed to dialyze the blood during a single hemodialysis therapy. Hemodialysis treatment lasts several hours and is generally performed in a treatment center about three or four times per week.

Another form of kidney failure treatment involving blood is hemofiltration ("HF"), which is an alternative renal replacement therapy that relies on a convective transport of toxins from the patient's blood. This therapy is accomplished by adding substitution or replacement fluid to the extracorporeal circuit during treatment (typically ten to ninety liters of such fluid). That substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is another blood treatment modality that combines convective and diffusive clearances. HDF uses dialysate to flow through a dialyzer, similar to standard hemodialysis, providing diffusive clearance. In addition, substitution solution is provided directly to the extracorporeal circuit, providing convective clearance.

Peritoneal dialysis uses a dialysis solution, also called dialysate, which is infused into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. The patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting more than an hour. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow the dialysate to dwell within the cavity, and allow the transfer of waste, toxins and excess water to take place. The source can be multiple sterile dialysate solution bags.

APD machines pump spent dialysate from the peritoneal cavity, though the catheter, to the drain. As with the manual process, several drain, fill and dwell cycles occur during dialysate. A "last fill" sometimes occurs at the end of APD, which remains in the peritoneal cavity of the patient until the next treatment.

Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Continuous flow, or CFPD, systems clean or regenerate spent dialysate instead of discarding it. The systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia. The ammonia is then removed from the dialysate by adsorption prior to reintroduction of the dialysate into the peritoneal cavity. Additional sensors are employed to monitor the removal of ammonia. CFPD systems are typically more complicated than batch systems.

It is known with PD therapy that the diffusive properties of the peritoneum degrade over time due at least in part to chronic exposure to glucose. While research has been done to find an alternative osmotic agent, glucose remains the industry standard. Accordingly, a need exists for an improved PD therapy, which addresses the degradation of the effectiveness of the diffusive properties of the peritoneum over time.

SUMMARY

The examples below describe systems that provide a improved dialysis treatment. The systems address the degradation of clearance effectiveness of PD due to the chronic exposure of the peritoneum to glucose. In one preferred implementation of the systems described below, the systems are tailored to be used by the patient at home. It should be appreciated however that the machines are not limited to at home use and can instead be adapted for in-center or hospital use.

The systems in general provide an opportunity to the patient to alternate between PD, HD and/or HDF. Alternating therapies provides two primary advantages, namely, preserving maximum residual renal function in PD and obtaining maximum urea clearance through HD or HDF. The systems provide "peritoneal rest" by enabling patients to perform HD over given intervals of time. Preliminary studies ([1]: Tomo T et al J Artif Organs, 2005; 8(2): 125-9; [2]Zareie M., et al, *Nephrol Dial Transplant,* 2005 January; 20(1): 189-93; [3]Rodriquez A., *Advanced Peritoneal Dialysis,* 2002; 18:7880) indicate that "peritoneal rest" after one or more PD treatment allows the peritoneum to heal at least to some degree prior to the next exposure to glucose.

The systems provide a PD machine or cycler, which includes additional hardware enabling HD to be performed in intervals as desired. One goal of the system is to provide a similar look, feel and mode of operation for a patient that over time moves from early stages of end-stage renal disease (exclusively or mainly PD through more advanced stages of end-stage renal disease (exclusively or mainly HD). That is, the same machine can be used to perform PD only, HD (HDF) only or to alternate between PD and HD (HDF).

In one embodiment, the PD/blood treatment cycler uses pneumatic technology to control dialysate flow, such as the pneumatic technology successfully employed in the HomeChoice® PD machine marketed by the assignee of this application. The pneumatic technology pumps dialysate in both PD and HD configurations. The PD cycler controls dialysate and ultrafiltrate flow for both PD and HD therapies and also acts as the master controller for a separate blood pump used for HD. In one embodiment, the blood pump is provided separately from the PD cycler or unit, wherein the control unit of the PD unit controls the blood pump via a universal serial bus, serial, hard-dock or other type of communication. The blood pump can be operated pneumatically using the same technology as for dialysate flow or be driven via another type of pumping, such as peristaltic pumping. The blood pump unit removes blood from the patient and pushes it through a dialyzer, returning the blood to the patient. The PD unit drives dialysate through the dialyzer, on the outside of the dialyzer fibers, countercurrent to blood flow through the inside of the fibers in one embodiment.

In an alternative embodiment, the PD unit is configured to accept an add-on blood pump. Here, a single disposable unit can be used for both dialysate delivery and blood flow. Or, as shown below, separate dialysate and blood cassettes can be used. If the machine is used for PD then the blood pump and blood cassette are not used. When the machine used for a blood treatment, such as HD, a blood pump module is added and the blood cassette is used.

It should be appreciated that the HD/PD system is not limited to using pneumatic control for pumping. The dialysate and/or the blood pump can be driven mechanically or hydraulically for example. It is also contemplated to use peristaltic pumping to drive not only the blood but also to pump dialysate. Here, the PD system can employ a separate volumetric control device for the control of dialysate flow, e.g., one or more balance chamber in combination with the pump, to meter the same amount of dialysate to and from the dialyzer or peritoneum. A separate pump driven balance chamber is also used to meter a known amount of spent fluid from the system, known as ultrafiltrate.

As discussed, it is contemplated to use different pumping technologies to drive the blood. In one embodiment, the PD/blood treatment system uses a peristaltic pump to drive the patient's blood. In an alternative embodiment, blood is pumped, pneumatically, mechanically, hydraulically or any suitable combination thereof. The same technology that is used to drive the dialysate can be used to pump blood. Using the same pumping technology to drive both dialysate and blood simplifies the control schemes and accompanying apparatus necessary to control ultrafiltrate for both PD and HD.

The blood pumping unit, whether stand-alone or added to the dialysate or PD unit, includes pressure sensors positioned to sense arterial and venous blood pressure. The blood unit also includes an air trap in at least the return or venous line. The blood unit further includes one or more valves or clamps to shut off the flow of blood in the event air is detected, a leak is detected or upon an access disconnection from the patient. One or more priming and/or rinseback device and method is also used, such as one that gravity feeds saline or to pushes dialysate into the extracorporeal circuit.

The dialysate in both PD and HD needs to be heated. The PD/blood treatment system uses batch type heating in one embodiment, such as that used in the HomeChoice® PD system. The PD/blood treatment system uses inline dialysate heating alternatively, such as resistive, inductive, convective or radiant inline heating (or any combination thereof).

In one HD configuration, the dialysate pumping unit pumps dialysate from a source bag to the dialyzer, which can be connected to the blood unit, and from the dialyzer into a recirculation bag. The recirculation bag enables spent dialysate to be reused. In one embodiment, the system pumps all fresh dialysate from one or more source bag, through the dialyzer, and to one or more recirculation bags. The system then reuses the spent dialysate from the recirculation bags. This method removes urea advantageously when its concentration in the body is the highest, namely, at the beginning of treatment with fresh dialysate. That is, in this counter-concentration arrangement, the freshest of the fresh dialysate meets blood having the highest concentration of urea to maximize the clearance of same. The spent dialysate cycle helps to remove other waste products, such as middle molecules, e.g., Beta-2 Microglobulin that are typically slow to cross the dialyzer fibers. The multiple pass use of dialysate allows the dialysate to become saturated with all of the toxins to be removed.

In one embodiment multiple supply bags are provided. A separate recirculation bag captures spent fluid from a first source bag. The first source bag is then used as the recirculation bag for the second dialysate supply bag. The second dialysate supply bag is then used as the recirculation bag for the third supply bag and so on. After all fresh solution has been pumped through the dialyzer once, the machine or system pumps the once-used dialysate from the recirculation bags, through the dialyzer, and back to the recirculation bags. If each of three supply bags holds six liters of fresh fluid, for example, the dual circulation of the dialysate provides eighteen liters of fresh clearance and eighteen liters of partially spent clearance.

The PD/blood treatment system is also configurable for hemodialfiltration ("HDF"), which combines diffusive and convection clearance modes of HD and hemofiltration, respectively. Molecules such as Beta-2 Microglobulin ("Beta-2"), do not diffuse through the dialyzer as efficiently as urea or creatinine for example. Because of its size, Beta-2 typically needs to be "dragged" across the dialyze membranes. Since the concentration of Beta-2 in the dialysate is likely not to be near equilibrium even after an initial entire eighteen liter circulation of fresh dialysate through the dialyzer, the partially-spent dialysate is used again in a convective way to remove Beta-2 in one embodiment.

In one embodiment, the PD/blood treatment system includes a substitution pump, which introduces a substitution fluid directly into the extracorporeal circuit in front of, down stream of, or both upstream and downstream of, the dialyzer. Here, diffusive and convective clearances occur simultaneously. This can be accomplished with an extra pump and separate fluid holder or by "time sharing" the other pumps.

In one HDF implementation, the first eighteen liters is used diffusively to perform HD, the second eighteen liters is used convectively (in an HF manner) to provide an overall HDF therapy. In the second run the PD/blood treatment system performs HDF using a "push-pull" method. In the push-pull method, the system increases the inlet dialysate pressure to be greater than that of the blood pressure, so that dialysate flows atypically through the membrane walls of the fibers within the dialyzer and into the blood circuit of the HD system. The pressure on the dialysate side of the membranes is then reduced, pulling fluid from the extracorporeal circuit into the dialysate circuit. This cycle is repeated a number of times using the last eighteen liters of dialysate in one implementation. Alternatively, a portion of the first eighteen liters or all thirty-two liters can be used to perform push-pull HF.

As mentioned, the first eighteen liters of HD clears urea primarily, while the eighteen liters of once-used dialysate used in the push-pull manner removes middle molecules or ones that need to be dragged across the dialyzer. It should be appreciated that pushing the dialysate through the membranes has the benefit of filtering the dialysate before it enters the extracorporeal circuit. The convective clearance comes from the fact that the once-used dialysate is still "cleaner" than fluid in the blood, for which the once-used dialysate is substituted. The push-pull method can be implemented in a dual needle or single needle arrangement as shown below.

Regarding single needle operation, another system of the present disclosure includes a dual, single needle arrangement. As described herein, single needle systems are advantageous in one respect due to their inherent and relative immunity to access disconnection problems. One drawback of typical single needle systems however is reduced clearances. Single needle systems are generally less efficient than dual needle systems because single needle systems are either filling or removing fluid to or from the patient at any given time. Dual needle systems perform both functions simultaneously, increasing clearance efficiency. Disclosed herein is a dual, single needle system in which two single needle therapies are performed in essence at the same time. One therapy delivers fluid to the patient, while the other removes fluid from the patient, in an alternating single needle format, in one embodiment.

In a further alternative embodiment, HDF is performed using a pair of high flux dialyzers with a variable flow restriction placed between the two dialyzers. The variable flow restriction causes a dialysate pressure increase in the upstream dialyzer, which is enough to force dialysate into the extracorporeal circuit. This type of system is described in co-pending U.S. patent application Ser. No. 10/982,170, entitled "High Convection Home Hemodialysis/Hemofiltration And Sorbent System", filed Nov. 4, 2004, owned by the assignee of the present application, the entire contents of which are hereby incorporated by reference.

The systems include a control scheme and corresponding user interface that decides which treatment modality to perform manually automatically (e.g., according to a doctor's prescription). For example, if determined automatically, the machine upon power-up recalls which modality is to be performed and prompts the patient or user accordingly. If determined manually (e.g., patient or caregiver determines) or the patient or caregiver can enter the information at the start of treatment according to a prescribed chart or calendar. The machine again prompts the patient accordingly.

It is therefore an advantage of the present disclosure to provide a combination PD/HD, PD/HF or PD/HDF system.

Another advantage of the present disclosure is to provide a single system that can manually or automatically perform different modalities of dialysis as desired, either over a same therapy or different therapies.

A further advantage of the present disclosure to provide a modular PD/blood treatment system, which enables a modular blood pumping unit to operate with a stand alone PD unit.

It is still another advantage of the present disclosure to provide an improved single need dialysis treatment.

Additional features and advantages are described herein, and will be apparent from, the following Detailed Description and the figures.

BRIEF DESCRIPTION OF THE FIGURES

FIG. 9A illustrates a dual-single needle PD/"push-pull" hemo(dia)filtration system in a first valve state.

FIG. 9B illustrates a dual-single needle PD/"push-pull" hemo(dia)filtration system in a second valve state.

FIG. 12A schematically illustrates the logistics involved with the control architecture for the PD systems having blood treatment options described herein.

FIG. 12B schematically illustrates the disposables involved with the control architecture for the PD systems having blood treatment options described herein.

FIG. 12C schematically illustrates various embodiments for power distribution schemes for the control architecture of the PD systems having blood treatment options described herein.

FIG. 15 is a perspective view of one embodiment a blood cassette for the system of FIGS. 13A and 13B.

FIGS. 18A to 18E are perspective views of a PD/HD system in which the blood unit or module (FIG. 18C) is provided as a separate device, which can be docked to (FIGS. 18D and 18E) the PD unit (FIGS. 18A and 18B).

FIG. 19 is a schematic flow diagram illustrating one operational sequence for the PD/blood treatment systems described herein.

FIG. 22 is a schematic flow diagram illustrating a third alternative operational sequence for the PD/blood treatment systems described herein.

DETAILED DESCRIPTION

PD/HD Systems

Figure 1:
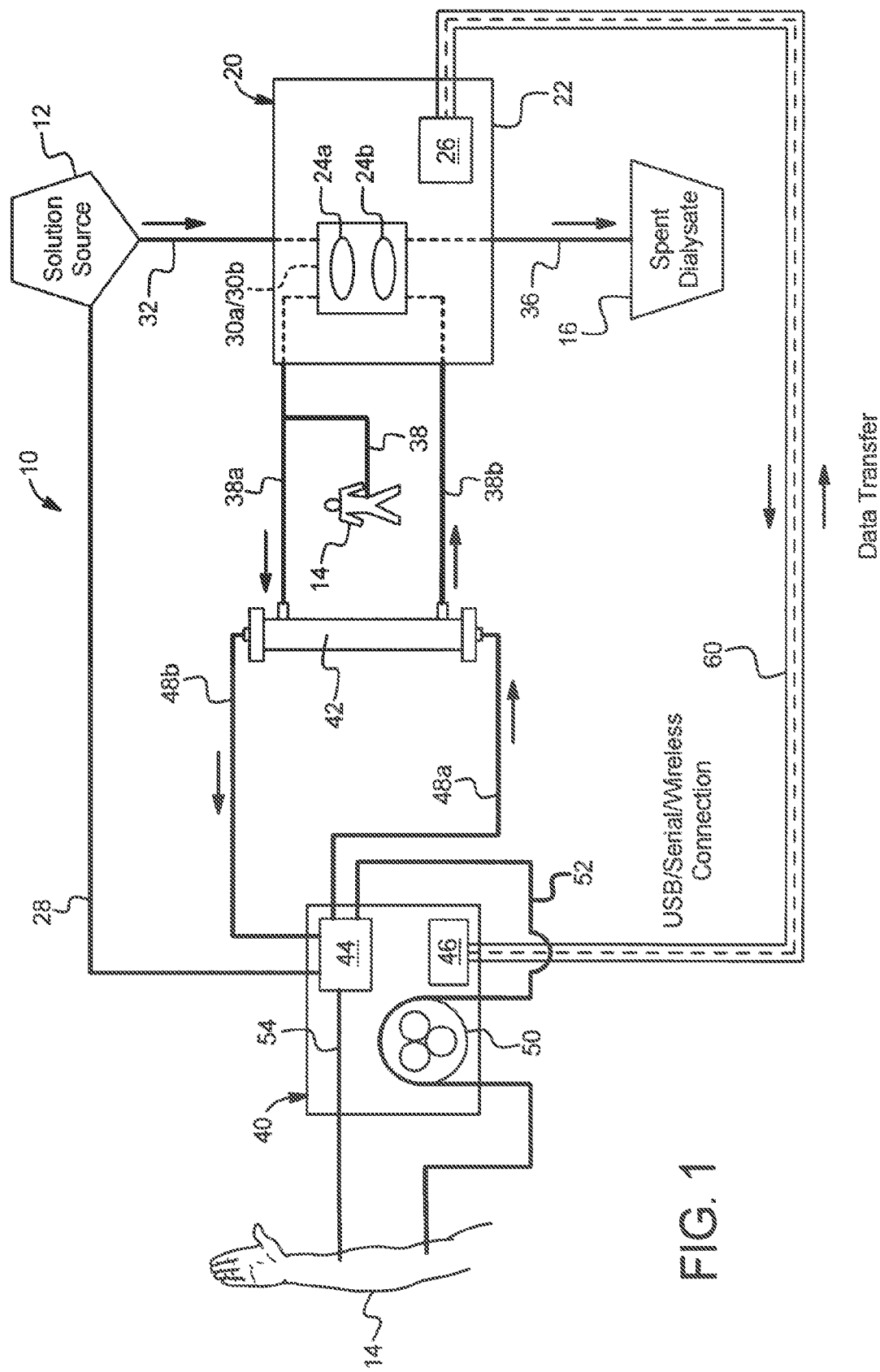
FIG. 1 is a schematic diagram of one embodiment of a PD/blood treatment system in which spent dialysate is sent to a drain.

Referring now to the drawings and in particular to FIG. 1, one embodiment for a combined PD/HD system is illustrated by system 10. System 10 includes a peritoneal dialysis ("PD") machine or unit 20. PD unit 20 as discussed herein is sued interchangeable for PD, HD, HF and HDF. For ease of description, however, unit 20 is generally referred to herein as PD unit 20.

Machine or unit 20 can be any suitable PD machine or unit, such as the HomeChoice® automatic peritoneal dialysis ("APD") machine, marketed by the assignee of this application. PD unit 20 includes a housing 22. Housing 22 houses components necessary to perform peritoneal dialysis, such as pumps 24a and 24b. Pumps 24a and 24b in the illustrated embodiment are pneumatically operated cassette-based pumps. The HomeChoice® machine pumps use a fluid management system ("FMS") to control the volume of fluid and ultrafiltrate removed from the patient accordingly. FMS is described for example in U.S. Pat. No. 5,431,626 ("the '626 Patent"), entitled "Liquid Pumping Mechanisms For Peritoneal Dialysis Systems Employing Fluid Pressure", the entire contents of which are incorporate herein by reference. As discussed in detail below, PD unit 20 can employ any suitable type of pump and valve actuation.

The '626 Patent describes other components located within or on housing 22 necessary for dialysate, such as the pneumatic pump and valve actuators, heater actuator and controller. The control unit of PD unit 20 is shown schematically in FIG. 1 as master controller 26. Master controller 26 is configured with the software and processing needed to run PD unit 20 in a peritoneal dialysis mode. The '626 Patent describes one possible control of PD unit 20. Master controller 26 is also configured to communicate with and control a delegate controller 46 located within a separate blood pump unit 40. The master/delegate control of PD unit 20 and blood pump unit 40 is discussed in detail below.

Blood pump unit 40 as described herein is used interchangeably for HD, HF, HDF. For ease of description, however, blood pump unit 40 is generally referenced to herein as HD unit 40.

As discussed in the '626 Patent, to perform PD dialysate unit 20 operates with a disposable fluid cassette. The disposable fluid cassette connects fluidly to a number of fluid line, such as one or more supply lines, a patient line, and a drain line. The cassette is shown schematically in FIG. 1 as cassette 30a for PD or cassette 30b for HD or HDF (referred collectively as HD cassette 30b for simplicity). Cassette 30a is dedicated solely for PD use and can be the HomeChoice® machine cassette for example. HD cassette 30b is dedicated to HD or HDF.

Generally, automated peritoneal dialysis is done on a batch or semi-batch basis, in which fresh fluid is pumped to the patient's peritoneum and allowed to dwell within the peritoneal cavity before being pumped from the peritoneal cavity to drain. Other PD modalities such as tidal flow remove a portion of the fluid dwelling within the peritoneal cavity and replace that portion with a fresh portion. Here still, only a single catheter is needed because at any one time fluid is either being sent to or drawn from patient 14. In such a case, a single dialysate inlet/outlet line 38 (shown in FIGS. 1 to 8A) is used instead of separate inlet and outlet lines discussed below.

It is contemplated for system 10 to perform CFPD, which includes a simultaneous filling and draining of patient 14. Here, separate lines 38a and 38b lead from PD cassette 30a to patient 14. Or, a single dual lumen catheter is used. In either case, PD cassette 30a provides two patient ports, which are akin to dual ports dialyzer used with HD cassette 30b to connect it fluidly to dialysate outlet and inlet lines 38a and 38b, respectively.

Cassette 30b is configured for HD. It differs from cassette 30a at least in that the "patient" for HD cassette 30b is a dialyzer 42, which requires outlet line 38a and inlet line 38b. Certain flowpaths of HD cassette 30b are also modified.

In one embodiment PD cassette 30a and HD cassette 30b are sized the same, so that each can be placed alternatively into the same dialysate machine 20. This involves structuring the flowpaths of both cassettes so that the pumping chambers and valve chambers of both cassettes 30a and 30b can operate with the same pump and valve actuators of PD unit 20. It is also contemplated to structure and configure the pump and valve actuators of PD unit 20, so that cassette 30a and 30b can be more easily configured to have the same shape, valve operation and pump operation. FIGS. 14A, 14B, 17A and 17B below illustrate suitable configurations for cassettes 30a and 30b, which share the same shape, valve and pump actuation.

As mentioned, HD cassette 30b in one embodiment is loaded into the same area of PD unit 20 as PD cassette 30a when performing a blood treatment. In an alternative embodiment, PD cassette 30a and HD cassette 30b are mounted in a different location of housing 22 of PD unit 20. The two cassettes 30a and 30b can then have different sizes and be configured so that valve actuation and pump actuation take place separately. An advantage here would be to incorporate the movement of blood into HD cassette 30b.

In any case, a supply line 32 is connected fluidly from fluid supply 12 to cassette 30a/30b. With PD a to/from patient line 38 is connected fluidly between PD cassette 30a and patient 14. Further, a drain line 36 is connected fluidly between cassette 30a/30b and drain 16. Cassette 30a/30b operates with pump and valve actuators, such as the pneumatic actuators described in the '626 Patent.

As seen in FIG. 1, HD cassette 30b of PD unit 20 of system 10 communicates fluidly with a dialyzer 42 via to-dialyzer line 38a and from-dialyzer line 38b, which are connected to an HD cassette 30b loaded in PD unit 20.

Cassettes 30a and 30b each connect to a drain line 36 and one or more supply line 32. Depending on the type of heating being used, cassettes 30a and 30b include to- and from-heater lines if the cassettes operate with a stand alone, e.g., inline heater. Alternatively, the fluid heating pathway of the inline heater is integrated into cassette 30a/30b, such that additional to- and from-heating ports are not needed. In a further alternative embodiment, batch heating is used, similar to that described in the '626 Patent, wherein dialysate can be gravity fed from a source 12 into a heater bag, which for example can be placed on top of PD unit 20. Supply line 32 then extends from the heater bag to cassette 30a/30b.

PD cassette 30a and HD cassette 30b include common features as alluded to above. For example, both can be made of the same material, which can include for example a rigid plastic piece defining the flow paths and valve seats. The rigid, plastic piece is then sealed via a thin flexible film or membrane, which is flexed to open and close valves and to pump fluid through pump chambers of pumping portions 24a and 24b of cassette 30a/30b. Also, cassette 30a/30b can have an air removal apparatus, such as air traps or air vents. Copending U.S. patent application Ser. No. 11/530,842 ("the '842 app"), entitled "Medical Fluid System With Flexible Sheeting Disposable Unit", filed Sep. 11, 2006, assigned to the assignee of the present application, the entire contents of which are incorporated by reference discloses purely flexible cassettes, which can be used for cassettes 30a/30b.

A separate blood cassette 44 in one embodiment is used with HD unit 40. Blood cassette 44 in one embodiment is formed integrally with HD cassette 30b in a single overall cassette. This is done for example when PD unit 20 and HD unit 40 are provided within a single housing or enclosure. In an alternative embodiment, blood cassette 44 is physically separate from HD dialysate cassette 30b. This is the case when HD unit 40 is housed in a separate enclosure and when HD cassette 30b and PD cassette 30a are meant to interchangeably mate with PD unit 20. In a further alternative embodiment, blood cassette 44 can be separate from HD dialysate cassette 30b, but wherein both are placed within a same housing or enclosure containing HD unit 40 and PD unit 20.

Blood cassette 44 is connected to a plurality of extracorporeal tubes. For example, blood cassette 44 is connected to a to-dialyzer line 48a and a from-dialyzer line 48b. Blood cassette 44 is also connected to arterial line 52 and venous line 54. As seen, arterial line 52 is also coupled operably to a peristaltic pump 50. Peristaltic pump 50 operates with valves located within blood unit 40 to pump blood from patient 14, through arterial line 52, into blood cassette 44, out through to-dialyzer line 48a, through the inside of hollow fibers within dialyzer 42, through from-dialyzer line 48b, back into blood cassette 44, through venous line 54, sending cleaned blood back into patient 14.

Blood pumped through dialyzer 42 travels inside a plurality of hollow-fiber membranes located within dialyzer 42. PD unit 20 pumps dialysate through to-dialyzer line 38a into dialyzer 42 wherein the dialysate passes along the outside of the hollow-fiber membranes as is known in the art, returning through from-dialyzer line 38b to HD cassette 30b, after which the once-used dialysate is sent via drainline 36 to drain 16 in system 10 of FIG. 1.

Blood cassette 44 is also valved and configured to connect fluidly with and operate a prime and rinseback line 28, which receives fresh solution from source 12. The fresh solution is used to flush to- and from-dialyzer lines 48a and 48b, the extracorporeal portion of dialyzer 42 and arterial and venous lines 52 and 54, respectively, in a prime sequence or blood rinseback sequence.

In one rinseback sequence, blood pump 50 is run in two directions, one direction to pull fresh solution through line 28, cassette 44, through arterial line 52, pushing any blood remaining in the arterial line back into patient 14. Next, blood pump 50 is reversed, pumping fluid from cassette 44, through venous line 54, pushing any blood remaining in venous line 44 back to patient 14.

In one prime sequence (performed before therapy starts), arterial line 52 and venous line 54 are connected together to form a closed loop. Pump 50 operates unidirectionally or bi-directionally to fill the extracorporeal lines with fresh fluid from line 28 completely before arterial line 52 and venous line 54 are connected to patient 14.

In an alternative embodiment, separate prime and rinseback line 28 is not used. Instead fresh dialysate from source 12 is driven via PD unit 20 into dialyzer 42, through the open pores of the membranes located with dialyzer 42, through to- and from-dialyzer lines 48a and 48b, into cassette 44, and then selectively through arterial and venous lines 52 and 54, as needed, to perform a prime or rinseback.

HD unit 40 includes other apparatuses to ensure safe pumping of the patient's blood through the extracorporeal circuit. For example, HD unit 40 includes safety clamps that occlude arterial line 52 and venous line 54 upon an alarm. Unit 40 also includes an air trap or an air vent in venous line 54 for example, which prevent(s) air from being delivered to patient 14. Extracorporeal apparatuses are shown in more detail below in connection with FIGS. 10 and 11.

HD unit 40 in one embodiment has its own user interface, which shows blood parameter settings and readings, such as blood pressure readings, blood temperature readings, transmembrane pressure and the like. The blood unit user interface can also be used to enter blood parameter settings through the use of a touch screen overlay or membrane switches for example. The sensors necessary to read blood parameters are provided within HD unit 40. In an alternative embodiment, the sensor information is sent via a data line or bus 60 to PD unit 20 for display. The blood settings are here made at the user interface of PD unit 20.

As seen in FIG. 1, HD unit 40 includes a controller 46, which can be one or more printed circuit board ("PCB") housing a microprocessor, read only memory ("ROM") and random access memory ("RAM"). Alternatively, controller 46 includes one or more application specific integrated circuit ("ASIC"). Controller 46 communicates via data line or bus 60 with control unit 26 of PD unit 20. In an embodiment, controller 26 is likewise a PCB, which includes a microprocessor, ROM and RAM. Control Unit 26 can be a series of printed circuit boards or otherwise include a supervisory processor that runs one or more delegate processor or delegate PCB. The supervisory role of control unit 26 applies also to the interface between PD unit 20 and HD unit 40, wherein controller 46 is configured as a delegate or subservient controller to the supervisory control unit 26 of PD unit 20. For example, PD unit 20 in one embodiment includes a safety controller, which monitors the safety and performance of components within PD unit 20 as well as within HD unit 40.

Data line or bus 60 is any suitable type of data transmission, such as a universal serial bus ("USB"), serial, hard-docked or wireless transmission. In a wireless embodiment, blood controller 46 communicates with dialysate control unit 26 via radio frequency ("RF"), encoded RF, secure Bluetooth technologies microwave, or other type of wireless communication. For example both blood controller 46 and dialysate control unit 26 can power wireless transceivers that allow two units to communicate back and forth. As described above, HD unit 40 in one embodiment is combined in the same housing with PD unit 20, in which case controller 46 and control cards for control unit 26 are plugged into a data bus 60.

Controller 46 sends and receives data from control unit 26. For example, Controller 46 can send blood pump speed, blood temperature, blood pressure, air detection, access disconnection and other information to control unit 26, which confirms that the information is within safe operating limits and also confirms that PD unit 20 itself is functioning properly to deliver dialysate to dialyzer 42. In the event that control unit 26 receives any information that either a function of blood unit 40 or PD unit 20 is in an alarm state, control unit 26 sends a message along data transmission 60 to controller 46. Controller 46 in turn shuts down blood pump 50 and closes the appropriate valves, either within blood cassette 44 or via a separate occluder to clamp arterial line 52 and venous line 54. The blood valves or clamps are configured to close upon a power off condition, providing fail-safe operation Referring now to FIG. 2, an alternative PD/HD system 70 is illustrated. System 70 includes many of the same components described above in connection with system 10, wherein such like components have the same alternative embodiments and are numbered the same. System 70 includes a number of differences however. For example, in system 10 dialysate pumps 24a and 24b (which are described as being of any of plurality of different types suitable for controlling the amount of dialysate delivered to and removed from dialyzer 42 and also for controlling an amount of ultrafiltrate removed from the patient 14) have been described primarily as being of the type from '626 Patent using the FMS technology. In system 70, pumps 24a and 24b are volumetric or membrane pumps. Membrane pumps 24a and 24b in system 70 each have a membrane 72, which moves back and forward within a chamber having a known volume. Thus with each stroke of membrane 72, a known volume of fluid is pumped to dialyzer 42 as illustrated.

Two or more membrane pumps 24a to 24b can be provided to provide an at least substantially continuous flow of fluid to and from dialyzer 42. That is, while one membrane pump 24a or 24b is in a fill stroke, the other is in a reload stroke. Membrane pumps 24a and 24b alternate in this manner. Membrane pumps 24a and 24b can also be used to remove ultrafiltrate. A separate membrane pump (not illustrated) is provided, in another embodiment for removing ultrafiltrate. The membrane pumps ensure that a precise amount of fluid is delivered to and removed from patient 14 for PD and dialyzer 42 for HD and is removed as ultrafiltrate by totaling the strokes of the dialysate and ultrafiltrate membrane pumps.

Suitable pneumatically and mechanically driven medical fluid pumps and diaphragms therefore are described in commonly owned U.S. patent Ser. No. 10/335,646, entitled, "Systems, Methods And Apparatuses For Pumping Cassette-Based Therapies", filed Dec. 31, 2002, the teachings of which are incorporated herein by reference. The pumps and pumping technologies described in commonly owned U.S. patent Ser. No. 10/155,754, entitled "Medical Fluid Pump", filed May 24, 2002, are also incorporated herein by reference.

Figure 2:
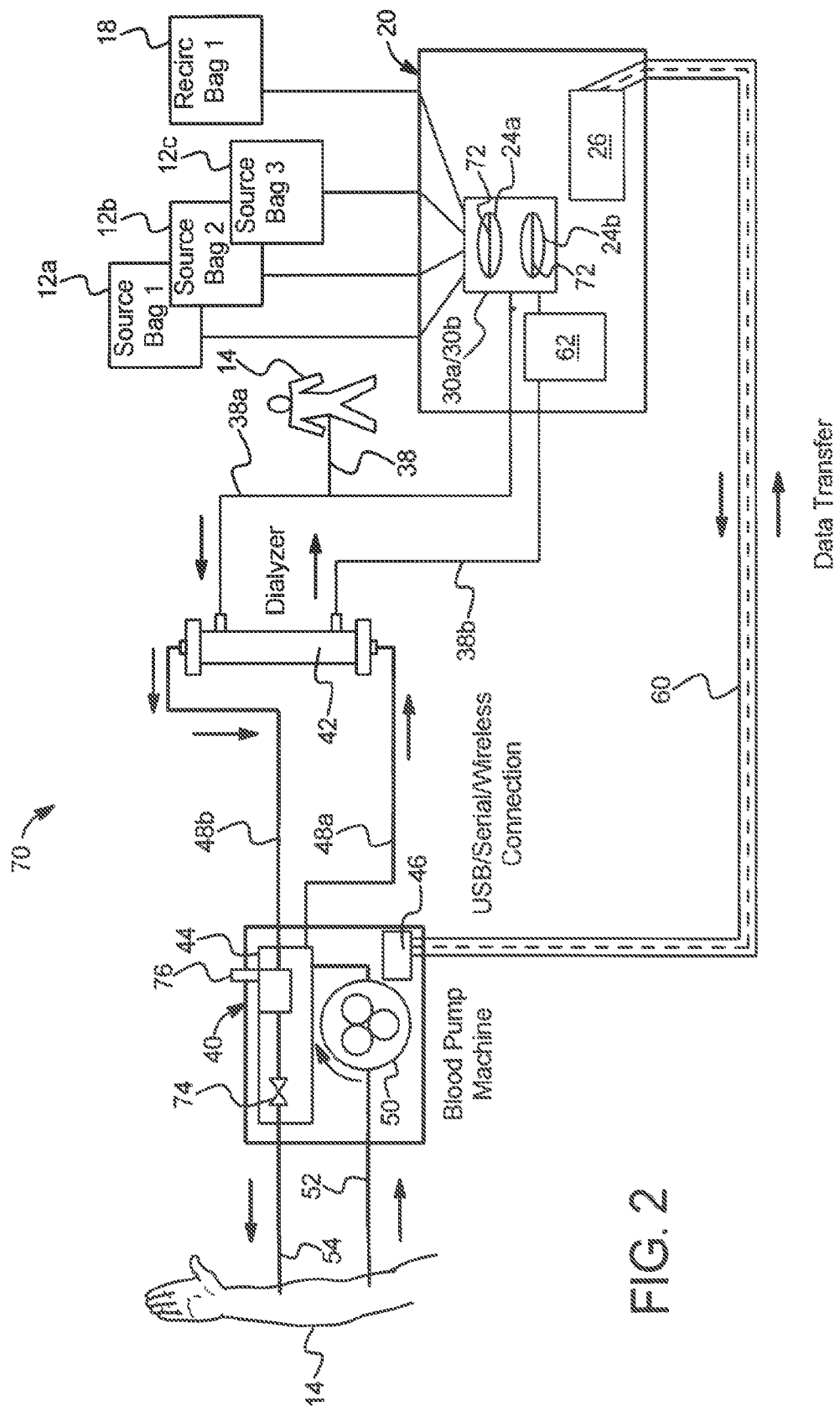
FIG. 2 illustrates another embodiment for the PD/HD system, which uses a peristaltic pump based blood unit in combination with a dialysate unit that pumps from a plurality of supply bags into a plurality of recirculation bags.

FIG. 2 also shows that blood cassette 44 of HD unit 40 includes valves or clamps, such as clamp 74, which for example closes venous line 54 upon an error condition or within a predetermined blood flow sequence. Blood cassette 44 also includes an air collection and removal apparatus 76, which traps air and/or enables air to vent to atmosphere.

Another main difference between system 70 and system 10 is that multiple supply bags 12a to 12c and a separate recirculation bag 18 are provided. In system 70, once-used dialysate is delivered from dialyzer 42 to recirculation bag 18 instead of to drain 16 as shown in connection with FIG. 10. Capturing once-used dialysate in recirculation bag 18 allows system 70 to reuse that solution. To that end, it is known that the concentration of urea in a person with renal failure is highest at the beginning of treatment and that it is recovered most efficiently via diffusion (clearance mode of HD). System 70 is accordingly configured in one embodiment to pump all fresh dialysate from supply bags 12a through 12c to dialyzer 42 advantageously before recycling any solution. This causes an optimum removal of urea.

In one embodiment, PD unit 20 pumps fresh dialysate from initial source bag 12a via HD cassette 30b to dialyzer 42 and pumps the resulting once-used solution into recirculation bag 18. When the pumping of fresh solution from solution bag 12a is complete, solution bag 12a is then used as the second recirculation or storage bag. Next, fresh solution is pumped from second solution bag 12b, through dialyzer 42 and back into first dialysate solution bag 12a (second storage bag). When that pumping is completed, solution is then pumped from third supply bag 12c, through dialyzer 42, back into second supply bag 12b (third recirculation bag).

System 70 then begins its recirculation cycle and causes the once-used solution to be pumped for example from recirculation bag 18, through dialyzer 42, and into fourth recirculation bag 12c. Once-used solution is then pumped from recirculation bag 12a through dialyzer 42, into recirculation bag 18. Finally, once-used solution is pumped from spent supply bag 12b, through dialyzer 42, into recirculation bag 12a. This scenario enables system 70 to pass, e.g., eighteen liters of dialysate through dialyzer 42 (assuming six liter supply bags) two times, once with fresh dialysate and again with once-used dialysate. Passing the once-used dialysate through dialyzer 42 a second time helps to remove more of certain larger molecules, such as beta-2 microglobulin, that are not diffused completely with the first pass. It should be appreciated that the twice-used dialysate can be recirculated a third or fourth time if needed. Recirculation can be used with the FMS pumping of system 10 and any other pumping system described herein.

Also, each of the systems described herein can employ a sorbent and/or carbon filled cartridge 62 that removes at least some of the waste from the once-used dialysate. Such one or more cartridge 62 is shown as being housed by PD unit 20 and in fluid communication with dialysate return line 38b. In this configuration, the cleansing chemicals and materials are provided in a quantity sufficient to clean multiple therapies both of one-used dialysate. PD unit 20 in on embodiment delivers a cartridge replacement message on its user interface after so many strokes of pumps 24a and/or 24b, number of therapies performed, number of days of service or any combination thereof.

In an alternative embodiment, cartridges 62 is provided as part of APD cassette 30b, here in a quantity sized for one treatment's worth of fluid. In a further alternative embodiment, the chemicals and materials are provided in recirculation bag 18 and/or in a compartment of supply bags 12a to 12c separated by an automatically separated frangible seal.

Suitable chemicals and cleaning materials for cartridge 62 include a material that is capable of non-selective removal of solutes from the therapy fluid that have been removed from the patient during therapy. The material includes a suitable sorbent material, such as carbon, activated carbon and/or other like material that can be contained within a, e.g., plastic, cartridge 62, in a medically safe manner. In an embodiment, the non-selective removal of solutes from the dialysate can be used, on its own, to clean the dialysate such that a more effective removal of solutes and excess water from the patient can occur upon reuse of the dialysate.

In an embodiment, cartridge 62 provides materials in addition to those that can non-selectively remove solutes from the dialysate. Additional materials include, for example, materials that can selectively remove certain solutes or the like from solution, such as, a binder material capable of selectively removing urea or a binder material capable of selectively removing phosphate, for example.

In general, the binder materials chemically bind the solutes, such as urea, to remove them from the dialysate or other suitable fluid medium as described below in greater detail. This process does not result in the release of harmful substances as reaction by-products as compared to an enzymatic process. For example, urease is known to enzymatically convert urea into ammonia. However, ammonia should then be removed from the dialysate prior to reintroduction of the fluid for PD, HD or HDF. With binder materials, the dialysate can be reintroduced without further processing of the dialysate as a result of the binder process. Materials capable of selective removal of solutes, particularly urea, can be used to enhance the cleaning efficiency of cartridge 62, so that the original eighteen liters of dialysate is restored closer to its "fresh" state.

Cleaning cartridge 62 can include materials that can selectively remove solutes from solution, such as binder materials, for example polymeric materials that are capable of removing nitrogen-containing compounds, such as urea, creatinine, other like metabolic waste and/or the like in solution. In general, these types of materials contain a functional group(s) that chemically binds with urea or other like solutes. For example, U.S. Pat. Nos. 3,933,753 and 4,012,317, each incorporated herein by reference, disclose alkenylaromatic polymers containing phenylglyoxal that can function to chemically bind urea. In general, the phenylglyoxal polymeric material is made via acetylation performed in, for example, nitrobenzene followed by halogenation of the acetyl group and treatment with dimethylsulfoxide as disclosed in U.S. Pat. Nos. 3,933,753 and 4,012,317. Another example of a polymeric material that is capable of selectively removing solutes, such as urea, from solution includes polymeric materials that contain a tricarbonyl functionality commonly known as ninhydrin as disclosed in U.S. Pat. No. 4,897,200, incorporated herein by reference.

Cleaning cartridge 62 can also include a number of components in addition to the materials capable of removing solutes from the dialysate. For example, cleaning cartridge 62 may have the capability to remove all or a portion of electrolytes, such as sodium, potassium, or the like, from the dialysate solution. In this case, an additional source of electrolytes in solution may be needed to replenish the dialysate after it has been cleaned. Cartridge 62 may also be configured to release bicarbonate or the like into the system depending on the type of cleaning material used. This can facilitate pH regulation of the dialysate. As necessary, cartridge 62 may include a filter to prevent proteins, particulate matter or like constituents from leaching or exiting from the cartridge and into the dialysate.

Molecules such as beta-2 micro microglobulin are known not to diffuse through a dialyzer as efficiently as urea or creatinine due to their size. These molecules can be removed more efficiently by dragging them across the membrane. The systems described herein take advantage of the convective potential remaining in the once-used (and potentially cleaned) dialysate. The once-used dialysate is used convectively, e.g., in an HF model as described below in FIGS. 6 and 7 to drag larger molecules such as beta-2 micro globulin across the dialyzer.

Figure 3:
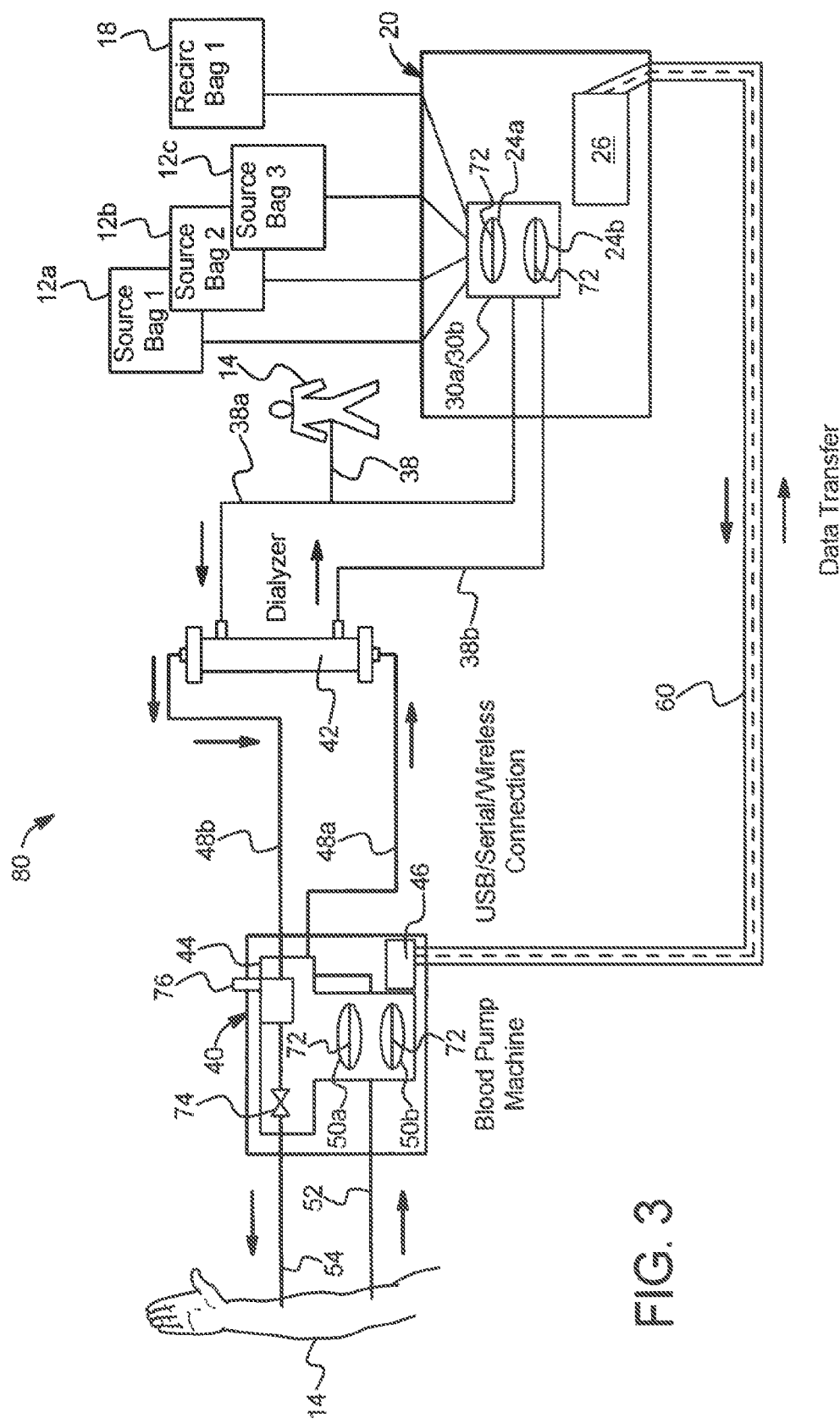
FIG. 3 illustrates another embodiment for the PD/HD system, which uses the same type of pumping for both the pumping of dialysate and blood.
Figure 4:
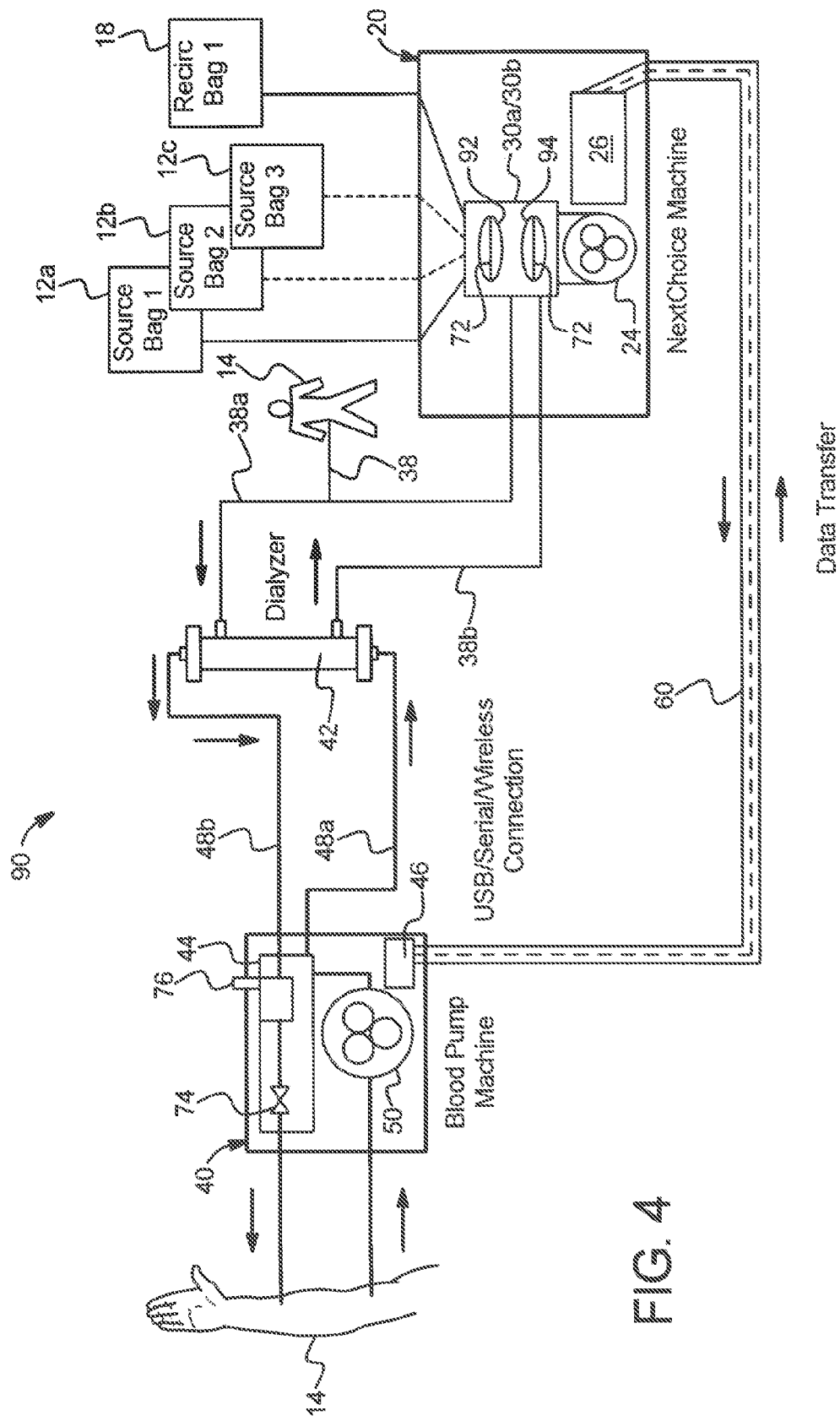
FIG. 4 illustrates a further embodiment of the PD/HD system, in which dialysate is pumped and metered using a peristaltic pump in combination with at least one balance chamber.
Figure 5:
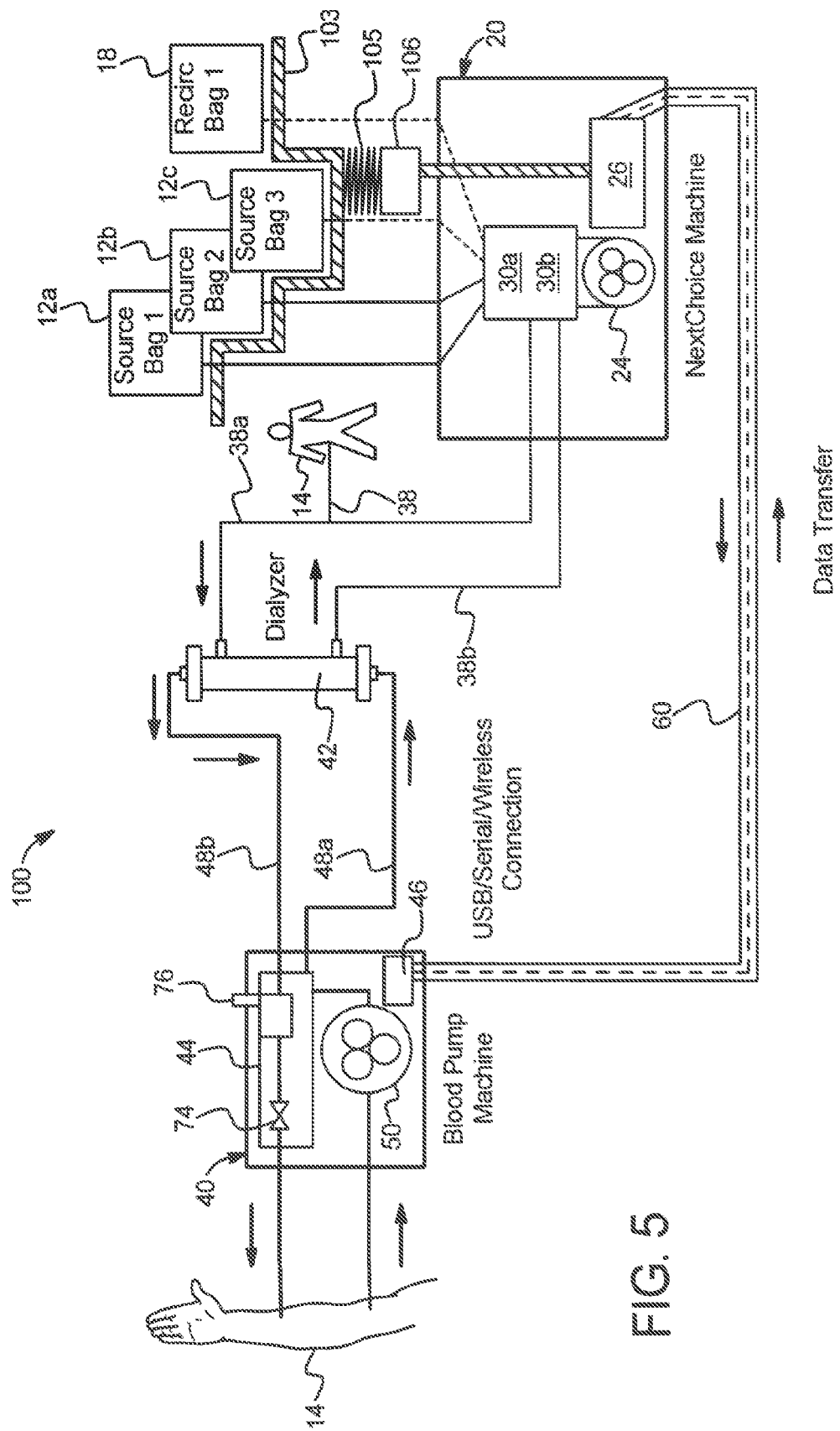
FIG. 5 illustrates yet another PD/HD system in which a weight scale is used to control volume of dialysate delivered and ultrafilteration.

Referring now to FIGS. 3 to 5, systems 80, 90 and 100, respectively, each show different types of pumping technologies that may used in the PD/blood systems to control dialysate and ultrafiltrate flow and volume. Systems 80, 90 and 100 are each shown with the recirculation bag configuration including supply bags 12a to 12c and recirculation bag 18 as illustrated in connection with system 70 of FIG. 2. It should be appreciated however that systems 80, 90 and 100 can alternatively pump spent dialysate to drain 16.

System 80 of FIG. 3 shows that the peristaltic blood pump 50 of systems 10 and 70 is replaced by a pair of volumetric or membrane pumps 50a and 50b. Membrane pumps 50a and 50b use the same pumping technology as dialysate membrane pumps 24a and 24b, each of which include a membrane 72 as described above. The import here is that the same pumping technology is used in both PD unit 20 and HD unit 40. This enables the control function of the PD/blood system to be simplified and standardized. For example, the strokes of the dialysate and blood pumps 24a/24b and 50a/50b, respectively, can be synchronized, such that a same set of end-of-stroke sensors can be used for each. In one embodiment, the FMS pumps of the HomeChoice® machine are used for both dialysate and blood pumping. Here, the same software can be used to calculate the amount of fluid delivered for both PD unit 20 and HD unit 40. The main difference between the operation of the PD unit when performing HD is that, the pumps operate continuously and against higher backpressures compared to the intermittent pumping and lower backpressures of PD.

System 90 of FIG. 4 illustrates a further alternative pumping technology, which combines one or more peristaltic dialysate pump 24 with a pair of balancing chambers 92 and 94. Balance chambers 92 and 94 can be housed in dialysate cassette 30a and 30b as disclosed in the patent application cited above. Balancing chambers 92 and 94 each include a membrane 72 that isolates and separates the fluid on opposite sides of the membrane 72. Although not illustrated, in one preferred embodiment two peristaltic dialysate pumps 24 are provided, one driving fresh and the other driving spent or once-used fluid, respectively, to either sides of both balancing chambers 92 and 94, so that the same exact amount of fluid is delivered to and removed from dialyzer 42 upon each stroke of balance chambers 92 and 94.

In one embodiment, each balancing chamber 92 and 94 includes two compartments, one termed a "pre-dialyzer" compartment and the other a "post-dialyzer" compartment. Each opposing "pre" and "post" compartment of a chamber is separated by a flexible diaphragm. Electrically, mechanically or pneumatically actuated valves control the filling and emptying of each compartment. Also, the "pre" compartments are alternately filled and discharged and the "post" compartments are alternately filled and discharged. Filling a "pre" compartment causes a discharge of a corresponding and opposing "post" compartment, respectively. Filling a "post" compartment causes a discharge of a corresponding and opposing "post" compartment.

Since the volumes of opposing "pre" and "post" compartments of the two chambers are equal, the system volumetrically balances the flow of dialysate to and from the dialyzer. One benefit of this volumetrically controlled system is that dialysate flow to and from the dialyzer can be accurately balanced over a wide range of flowrates.

In an embodiment, a third UF balancing chamber (not illustrated) is provided and driven by a spent peristaltic dialysate pump 24 dedicated to spent fluid, which drives spent fluid to both sides of UF chamber in addition to the spent compartments of balancing chambers 92 and 94. The third balancing chamber is used to meter ultrafiltrate. Here, instead of alternating fresh and spent pump cycles, the third UF balancing chamber receives spent dialysate on both sides of its membrane 72, which drives a known amount spent dialysate as UF to drain 16 or to a recirculation bag 12a to 12c or 18.

The configuration of system 90 is advantageous in one respect because peristaltic pump 24 is a low cost and safe medical fluid pumping technology. The drawback of a peristaltic pump is generally considered to be its accuracy. Balancing chambers 92 and 94, however, provide the accuracy needed to ensure that a prescribed amount of ultrafiltrate is removed from the patient both PD or HD.

Referring now to FIG. 5, a further alternative pumping technology suitable for use with the PD/blood systems is illustrated by system 100. System 100 weighs the dialysate delivered and ultrafiltrate removed. The weighing system uses a pan or container 103 that holds one or more or all of supply bags 12a to 12c and recirculation bag 18. Container 103 is coupled to a weight scale 105, which includes a load cell 106 configured to send a signal to dialysate control unit 26. The accuracy of the weight system enables the simpler, less accurate but safe peristaltic dialysate pump 24 to be used. One drawback with weighing systems is the need to weigh each of supply bags 12a to 12c and drain bags, such as drain 16 or the recirculation bag 18 discussed above. One gravimetric dialysis system overcoming this particular problem is disclosed in U.S. patent application Ser. No. 11/422, 267, filed on Jun. 5, 2006, entitled "Dynamic Weight Balancing Of Flow In Kidney Failure Treatments", assigned to the assignee of the present application, the entire contents of which are incorporated herein by reference.

As discussed above, certain molecules, such as beta-2 microglobulin, are removed more effectively via a convective clearance. One way of obtaining the benefits of both diffusive and convective modes of transport is via hemodiafiltration ("HDF"), which combines the diffusive clearance of dialysis and the convective clearance of hemofiltration. In general, hemofiltration involves the injection of a substitution fluid into the extracorporeal circuit directly (as opposed to the outside of dialysis membranes). Waste and toxins are removed from the blood liquid via a dilution or convection process, in which cleaned fluid is introduced into the patient's blood stream and clean-mixed-with toxic laden blood liquid is removed. Over time this process cleans the blood.

One way for the systems herein to perform hemodiafiltration is to connect a substitution fluid line to the to-dialyzer line 48a (predilution hemofiltration) or from-dialyzer line 48b (post dilution hemofiltration). This enables dialysate to be delivered to dialyzer 42 as discussed above and at the same time substitution fluid to be delivered to the extracorporeal circuit directly. A net amount of ultrafiltration is removed from the system through dialysate return line 38b from dialyzer 42 as discussed above with pure HD. The combined diffusive and convective clearance makes are generally thought to be one very effective way of treating a patient with kidney failure.

A separate pump in one embodiment is provided to pump the replacement fluid to the extracorporeal circuit directly. The separate replacement fluid pump can be provided on the PD unit 20 or the HD unit 40. The separate replacement fluid is more likely provided with PD unit 20, so that the replacement fluid supply can be kept with the dialysate supply 12 (e.g., either bagged dialysate or on-line dialysate). Any of the pumping technologies described herein for dialysate pump 24 can be used for the separate replacement fluid pump.

Figure 6:
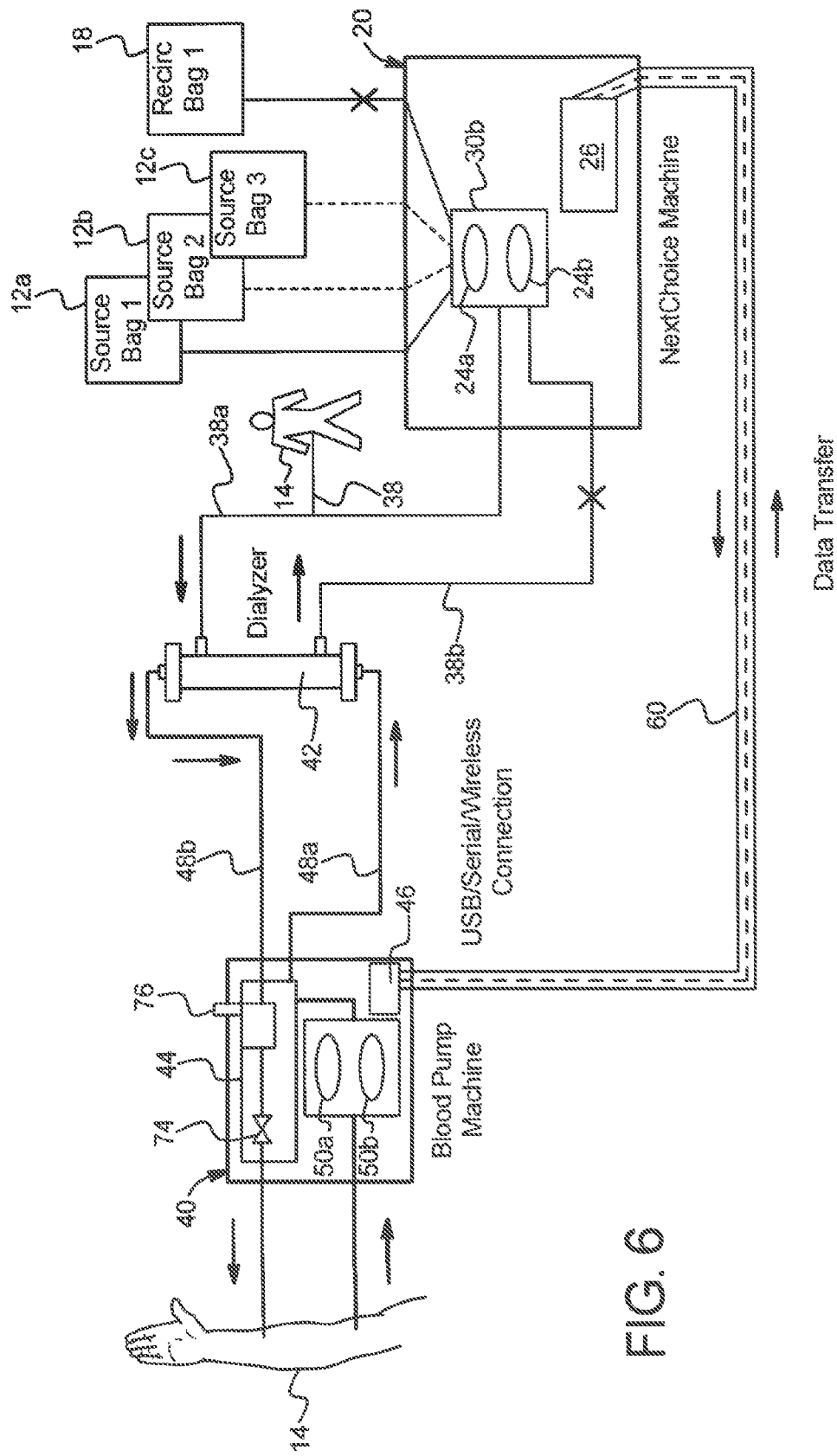
FIG. 6 illustrates a PD/HDF system in a first valve state configured to push dialysate into the extracorporeal circuit in a "push-pull" hemo(dia)filtration ("HDF") modality.
Figure 7:
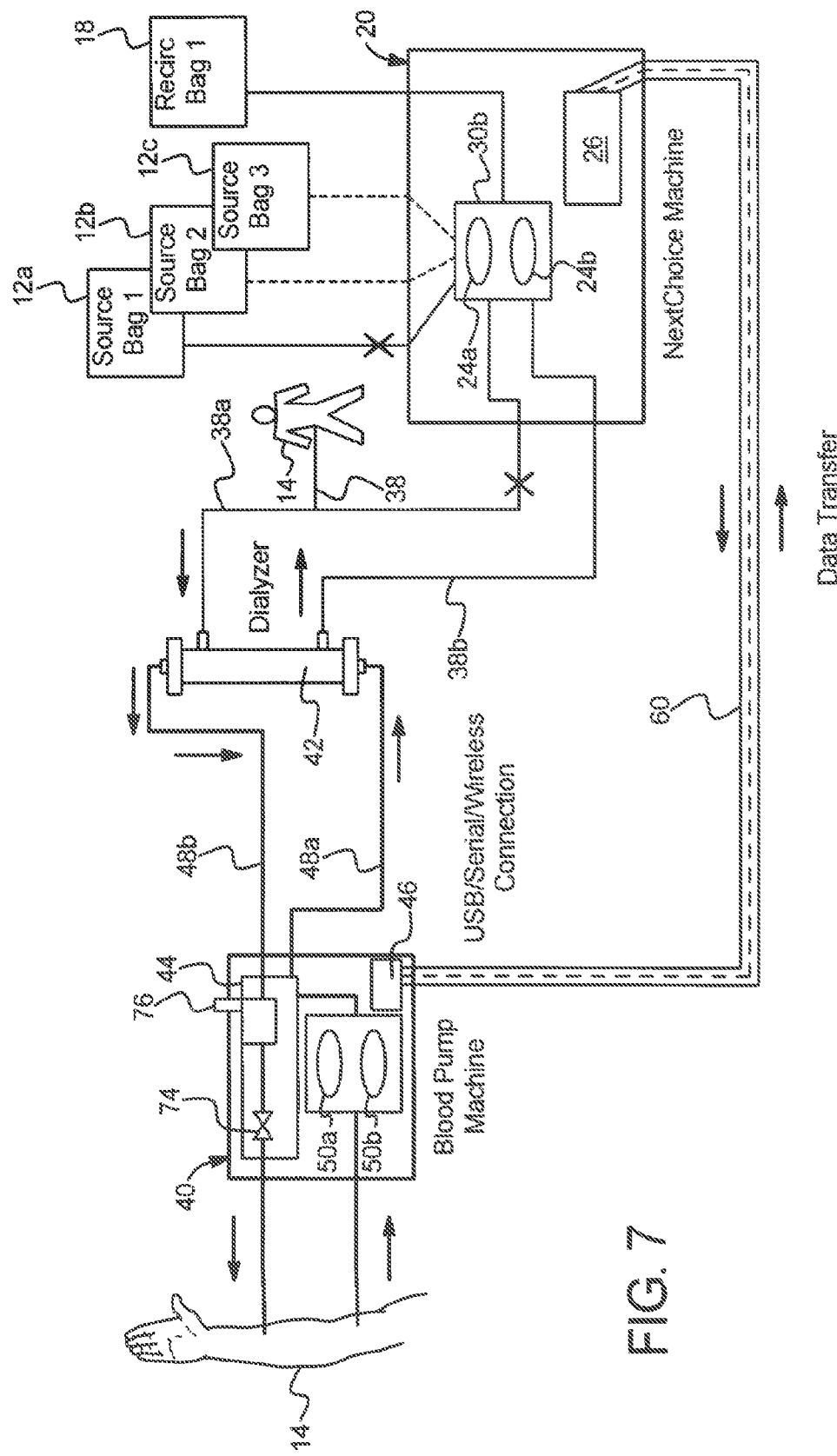
FIG. 7 illustrates a PD/HDF system in a second valve state, in which dialysate is pulled from the extracorporeal circuit into the dialysate circuit to perform a pull portion of the "push-pull" HDF.

While the PD/blood systems described herein can be provided with a separate substitution fluid supply and pump, one alternative apparatus is discussed in connection with FIGS. 6 and 7. FIGS. 6 and 7 illustrate a system having the pumping configuration of system 80. It should be appreciated however that any of the pumping technologies of the different PD/blood systems can be used in connection with the teachings of FIGS. 6 and 7. FIGS. 6 and 7 illustrate a push-pull technique for performing hemodiafiltration. Here, after using the fresh dialysate to perform pure HD, the PD/blood system uses the eighteen liters of once-used dialysate to perform a convective clearance. To do so, the to- and from-dialysate lines 38*a* and 38*b*, respectively, are opened and closed selectively to cause dialysate to be pushed either into the extracorporeal circuit or to be pulled from the extracorporeal circuit. The hollow fiber membranes located within dialyzer 42 act as a filter to help prevent some of the waste and toxins located within the once-used dialysate from re-entering the extracorporeal circuit. That is, the membranes tend to reclean the spent fluid. Dialysate cleaning cartridge 62 may also be used to at least partially clean the once-used, dialysate for the push-pull convective phase.

In FIG. 6, HD cassette 30*b* causes recirculation bag line from-dialysate line 38*b* to be closed (as indicated by the X's). Pumps 24*a* into 24*b* drive spent dialysate through to-dialyzer line 38*a* and into the extracorporeal circuit through the membranes of dialyzer 42. In FIG. 7, the valve state of HD cassette 30*b* is reversed, so that source bag 12*a* (for example) and to-dialyzer line 38*a* are closed (as indicated by the X's), while from-dialyzer line 38*b* and a valve enabling dialysate to flow to recirculation bag 18 are opened. Pumps 24*a* and 24*b* pull spent dialysate from the extracorporeal circuit, through the porous membranes of dialyzer 42, to recirculation bag 18. Over a number of push-pull cycles, more fluid is removed from the extracorporeal circuit than is sent into the extracorporeal circuit, resulting in a net fluid removal from the patient or ultrafiltrate.

Using the first eighteen liters to perform a diffusive clearance and the second eighteen liters to perform a convective clearance makes use of the fact that at the end of the diffusive process, the dialysate and blood liquid concentrations tend to be at a equilibrium. That is, the osmotic gradient between the blood liquid and dialysate has been lessened to the point that dialyzing the patient further at least for certain toxins may not have much cleansing affect.

Delivering the second eighteen liters to the extracorporeal circuit directly makes use of any remaining convective potential in the dialysate. The notion here is that the dialysate after one pass is still "cleaner" than the blood liquid. thus replacing the blood liquid with the once-used dialysate via, e.g., the push-pull method has a further cleansing effect.

The dual eighteen liter diffusive than convective treatment has an overall hemodiafiltration effect because both types of clearance modes are used. The method is a-typical however because the different clearance modes are performed at different times. Typical HDF using an additional substitution fluid-pump enables dialysate to be passed along the membranes of the dialyzer and substitution to be delivered to the extracorporeal circuit at the same time.

Figure 8A:
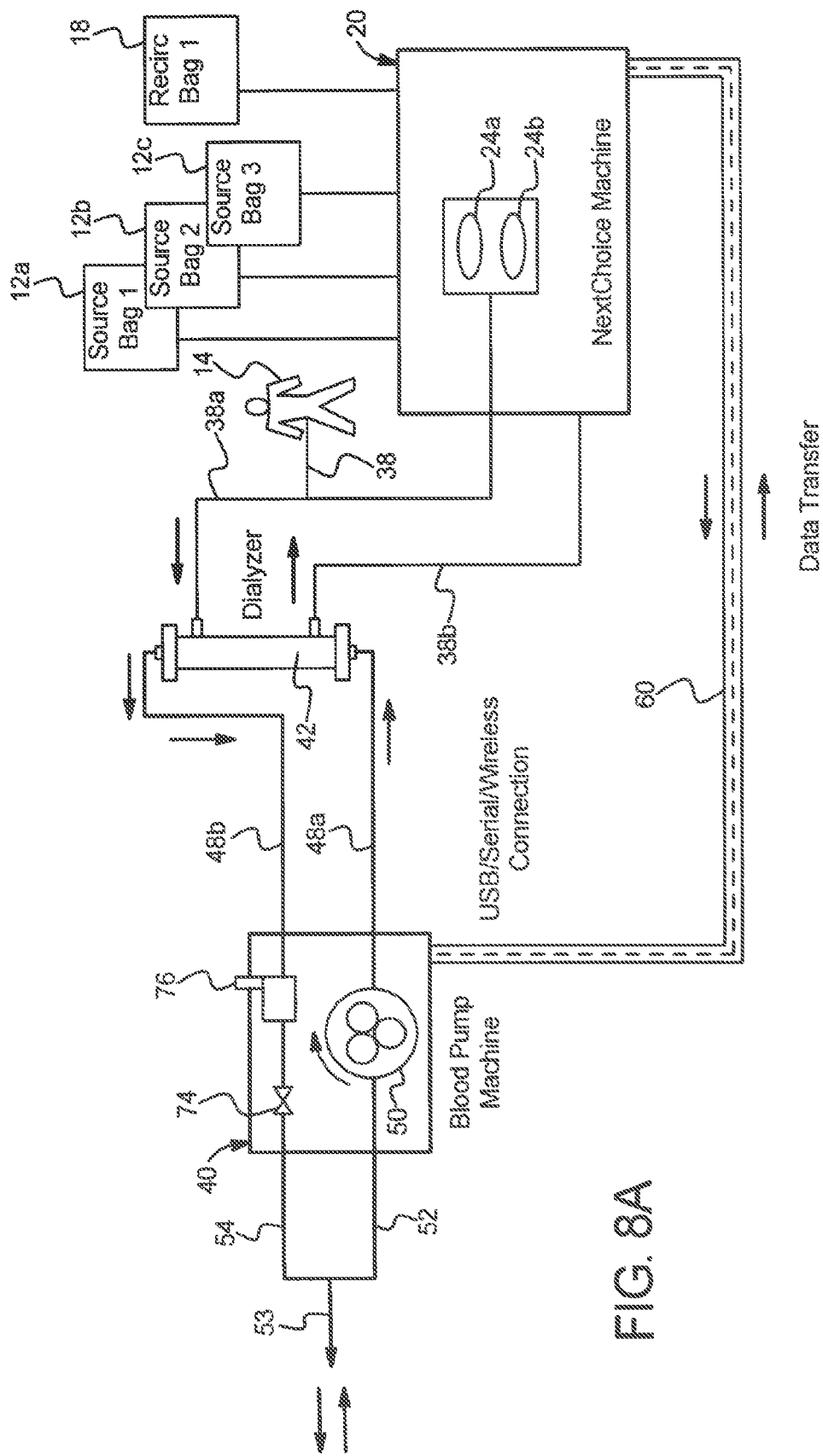
FIG. 8A illustrates a single needle PD/"push-pull" hemo(dia)filtration system.

FIGS. 8A to 8D illustrate a single needle type push-pull HD/PD system. FIG. 8A shows dialysate pumps 24*a* and 24*b* generally and a peristaltic version of blood pump 50. It should be appreciated however that any of the pumping technologies of the different PD/blood systems can be used in connection with the teachings of FIGS. 8A to 8D. It is contemplated to use the push-pull technique for the single needle system in combination with pure HD, pure HF or alone throughout the entire course of therapy. That is, assuming eighteen liters of bagged solution in supplies 12*a* to 12*c* is used, the first eighteen liters can be pure HD or pure HF, after which the second eighteen liters is used with the single needle push-pull method of FIGS. 8A to 8D. Alternatively, the single needle push-pull method can be used throughout the entire therapy, for example, using it with the fresh eighteen liters only or in combination with a reuse of the eighteen liters.

As with the push-pull system of FIGS. 6 and 7, to- and from-dialyzer lines 38*a* and 38*b*, respectively, are opened and closed selectively to cause dialysate to be pushed either into the extracorporeal circuit or to be pulled from the extracorporeal circuit. If it is intended to reuse the first eighteen liters of dialysate, dialyzer 42 acts as a filter for the reused dialysate. Alternatively, cleaning cartridge 62 described above is provided to clean the once-used dialysate.

In FIG. 8A, arterial line 52 and venous line 54 tee into a single lumen or needle 53. Single needle 53 is used to allow the system of FIG. 8A to push or pull blood to or from the patient intermittently.

Figure 8B:
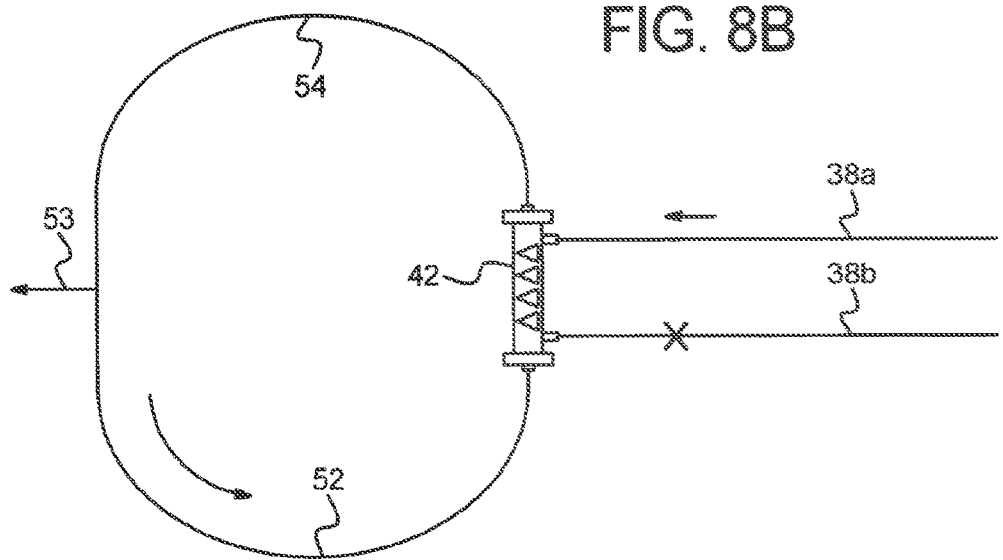
FIGS. 8B to 8D illustrate three stages of dialysate delivery for the single needle PD/"push-pull" hemo(dia)filtration system of FIG. 8A.

FIG. 8B illustrates a "push" phase of the single needle system of FIG. 8A. Here, a valve within PD unit 20 closes or occludes dialysate return line 38*b* or a corresponding path within dialysate cassette 30*b*. Dialysate pumps 24*a* and 24*b* pump dialysate through to-dialyzer line 38*a* into dialyzer 42. The arrows shown in FIG. 8B within the circuit of dialyzer 42 indicate that the resulting transmembrane pressure is such that dialysate is forced through the membranes of dialyzer 42 and into arterial and venous lines 52 and 54 of the extracorporeal circuit, resulting in a net flow of blood and dialysate into the patient through single needle access 53.

Figure 8C:
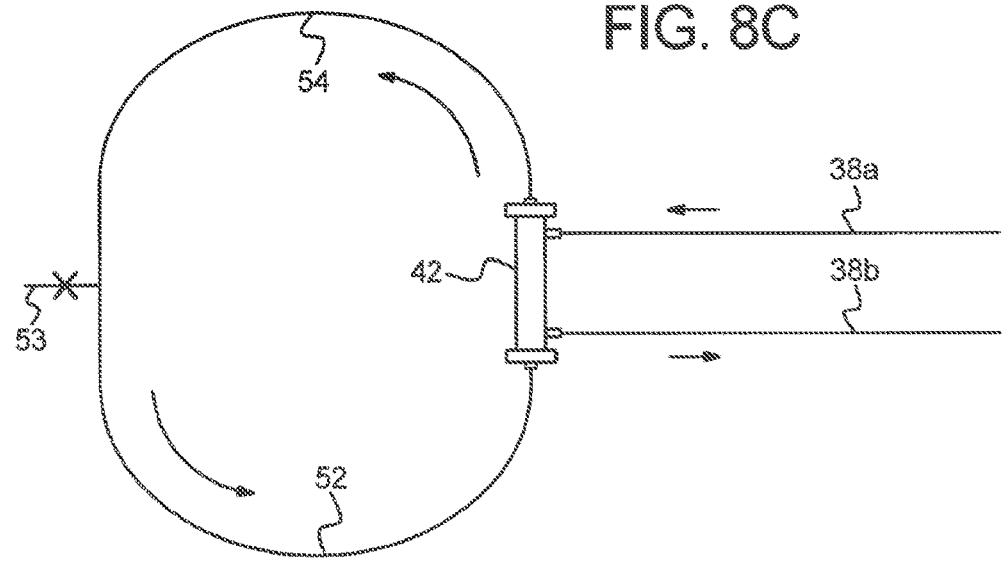

FIG. 8C illustrates a "hemodialysis" phase of the therapy for the single needle system of FIG. 8A. Here, between "push" and "pull" phases, PD unit 20 pumps fresh dialysate to dialyzer 42 through line 38*a* and removes spent dialysate from the dialyzer 42 via return dialysate line 38*b*. This procedure for example is performed for a long enough time to clean the amount of blood residing within arterial line 52, dialyzer 42 and venous line 54. Ultrafiltration or a net removal of liquid can also be performed during the hemodialysis phase of FIG. 8C. During this phase, single access line 53 is occluded as illustrated in FIG. 8C, for example, via a valve or occluder, such as valve 74 located within blood unit 40.

Figure 8D:
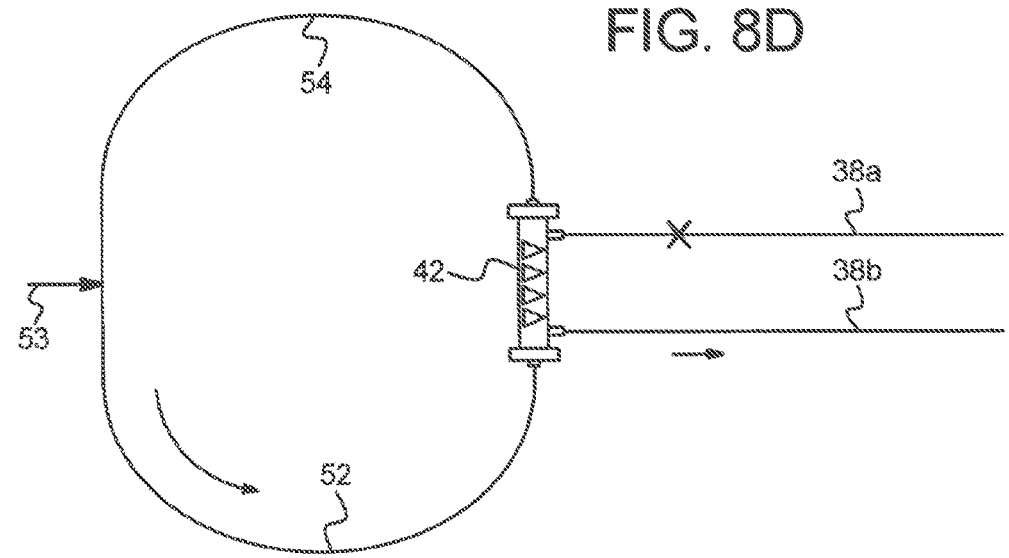

Referring now to FIG. 8D, a "pull" phase of the single needle system of FIG. 8A is illustrated. Here, single needle access 53 is opened, to-dialyzer line 38*a* is occluded and PD unit 20 pulls fluid from dialyzer 42. This sequence causes a transmembrane pressure within dialyzer 42 to conduct fluid from the extracorporeal circuit, through the membranes of dialyzer 42, and out from-dialyzer line 38*b* as indicated by the arrows of FIG. 8D.

The single needle, push-pull system of FIG. 8A is advantageous in a number of respects. For one, single needle access is less cumbersome to the patient. Second, problems due to needle dislodgement are not nearly as serious as with a dual access system. The most serious access disconnection problem occurs when a venous or return needle in a dual access system becomes dislodged, while the arterial needle remains lodged. Here, blood pump can continue to pull blood from the patient and return the blood outside of the patient. In the single needle system of FIG. 8A, if a needle dislodgement occurs, the patient potentially loses the amount of blood existing within dialyzer 42 and arterial and venous lines 52 and 54, but no more.

A further advantage of the single needle system of FIG. 8A is that blood pump 50 only has to rotate in one direction. In many single needle systems, two blood pumps are provided. Or, a complex valve and line arrangement is needed for a single blood pump 50 to be used. Here, on the other hand, arterial and venous lines 52 and 54 can be left open, while blood pump 50 rotates in single direction, simplifying the valving to occlude access line 53 and the dialysate to- and from-lines 38a and 38b at the appropriate times.

Referring now to FIGS. 9A and 9B, a continuous or dual, single needle system is illustrated in two valve states. As stated above, single needle systems are advantageous in one respect due to their inherent and relative immunity to access disconnection problems. One drawback of typical single needle systems however is reduced clearances. In essence, single needle systems are less efficient than dual needle systems because single needle systems are either filling or removing fluid to or from the patient at any given time. Dual needle systems perform both functions simultaneously, increasing clearance efficiency.

The system of FIGS. 9A and 9B performs two single needle therapies simultaneously, increasing the overall efficiency of the system. In one embodiment, one single needle fills the patient while the other single needle removes fluid from the patient, and vice versa, creating a virtually continuous flow. Pushing and pulling through each needle eliminates the dedicated "venous" needle found with circulatory dual needle systems and thus eliminates the most dangerous access disconnection element. Providing two single needle therapies however allows more fluid to be delivered to and removed from the patient for a given period of time versus standard single needle systems.

It is contemplated to use the dual, single needle system in combination with pure HD, pure HF or alone throughout the entire course of therapy. That is, assuming eighteen liters of bagged solution in supplies 12a to 12c is used, the first eighteen liters can be pure HD or pure HF, after which the second eighteen liters is used with the dual, single needle system and method of FIGS. 9A and 9B. Alternatively, the dual, single needle system and method can be used throughout the entire therapy, for example, using it with the fresh eighteen liters only or in combination with a reuse of the eighteen liters.

For convenience, dialysate pumps 24a and 24b of the dual-single needle system of FIGS. 9A and 9B are not illustrated but connect to dialyzer 42 via to- and from-dialyzer lines 38a and 38b as has been described herein. A peristaltic version of blood pump 50 is illustrated, however, it should be appreciated that any of the pumping technologies of the different PD/blood systems described herein can be used in connection with the teachings of FIGS. 9A to 9B.

Unlike the push-pull system of FIGS. 8A to 8D, to- and from-dialyzer lines 38a and 38b, respectively, do not have to be opened and closed selectively to cause dialysate to be pushed either into the extracorporeal circuit or to be pulled from the extracorporeal circuit. Here instead, fresh dialysate is fed continuously (or semi-continuously) to dialyzer 42 via to-dialyzer line 38a. Spent dialysate and ultrafiltrate is pulled continuously (or semi-continuously) from dialyzer 42 via from-dialyzer line 38b. The dual, single needle switching is performed via two three-way 108a and 108b that can be actuated electrically, pneumatically or mechanically.

In the illustrated embodiment, single lumen or needle 53a and 53b provide both arterial and venous access to patient 14. Single lumen or needle 53a connects to arterial and venous access line 153a. Single lumen or needle 53b connects to arterial and venous access line 153b. Access lines 153a and 153b each connect fluidly to both three-way valves 108a and 108b. Valve 108a is the valve through which all fluid removed (through either line 153a or 153b) from the patient (arterial fluid) flows. Valve 108b is the valve through which all fluid delivered (through either line 153a or 153b) to the patient (venous fluid) flows. Accordingly, all fluid flowing through valve 108b must flow through drip chamber 82 (and any other desirable apparatus disclosed for example in connection with FIGS. 10 and 11) and blood return line 48.

In the extracorporeal circuit of FIGS. 9A and 9B, blood pump 50 pulls fluid from patient 14, through three-way valve 108a and pushes blood through dialyzer 42, drip chamber 82 and three-way valve 108b back to patient 14. Three-way valves 108a and 108b are reversed in synchronization in one embodiment such that: (i) pump 50 pulls fluid from patient 14, though single access needle 53b, line 153b and valve 108a, while pumping fluid through drip chamber 82, valve 108b, line 153a and single access needle 53a to patient 14 (FIG. 9A, in which opened valves are darkened); after which valves 108a and 108b switch states so (ii) pump 50 pulls fluid from patient 14, though single access needle 53a, line 153a and valve 108a, while pumping fluid through drip chamber 82, valve 108b, line 153b and single access needle 53b to patient 14 (FIG. 9B, in which opened valves are darkened).

The embodiment illustrated in FIGS. 9A and 9B is most likely used for conventional HD, HF or HDF and not push/pull variations of those therapies, since it may be difficult to combine the push-pull switching in the dialysate circuit (e.g., FIGS. 8A to 8D) with the switching of blood valves 108a and 108b. The embodiment illustrated in FIGS. 9A and 9B can also be used with conventional hemodialysis machines as a way to address assess disconnect issues. It should be appreciated that the fluid through blood return line 48b can come from dialyzer 42 (HD), a source of replacement fluid (HF) or both (HDF). Further alternatively, the dual dialyzers 42a and 42b and backpressure restriction 56 of FIGS. 10 and 11 can be used in place of dialyzer 42 in the system of FIGS. 9A and 9B.

Figure 10:
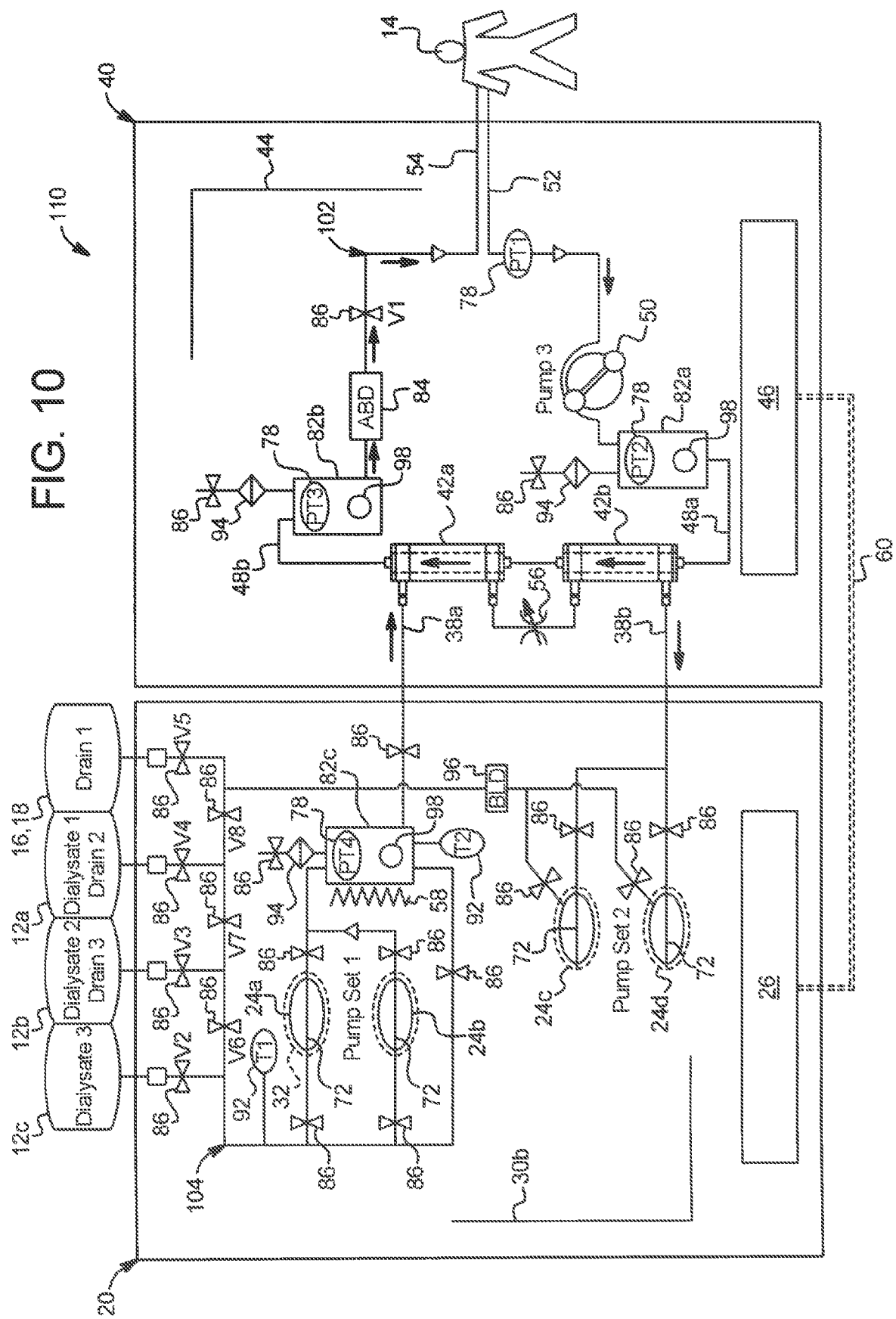
FIG. 10 illustrates a first alternative PD/HDF system for performing HDF using membrane pumps and a variable restriction placed between a pair of high flux dialyzers.
Figure 11:
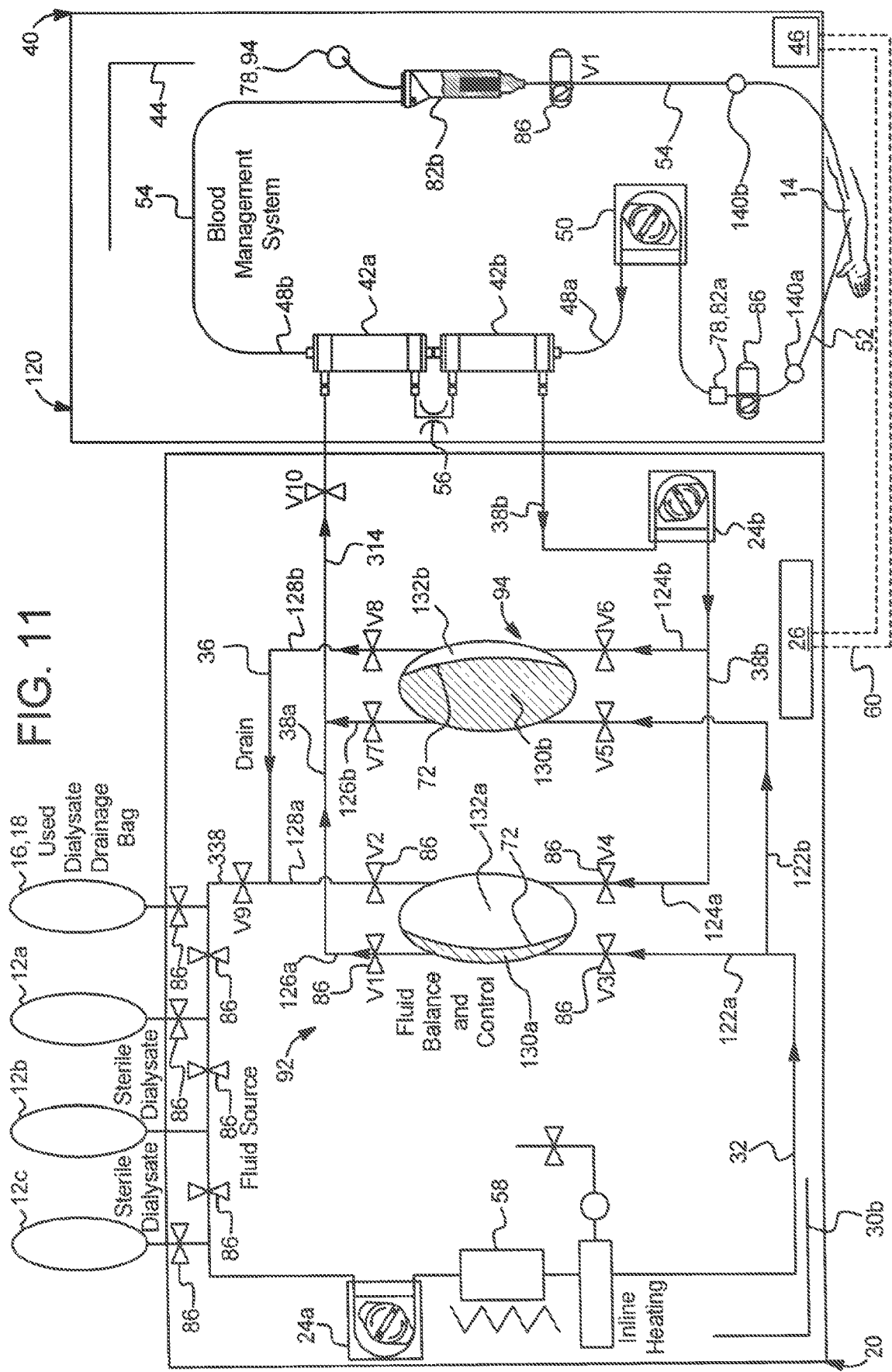
FIG. 11 illustrates a second alternative PD/HDF system for performing HDF using peristaltic pumps, a pair of balance chambers and a variable restriction placed between a pair of high flux dialyzers.

Referring now to FIGS. 10 and 11, two systems 110 and 120 for performing a simultaneous diffusion/convection therapy are illustrated, respectively. Systems 110 and 120, like the push-pull method, are advantageous because a separate substitution supply is not needed. Systems 110 and 120 are described in detail in U.S. patent application Ser. No. 10/982,170, entitled: "High Convection Home Hemodialysis/Hemofiltration And Sorbent System", filed Nov. 4, 2004, assigned to the assignee of the present application, the entire contents of which are incorporated herein by reference.

Systems 110 and 120 have separate or combined PD and HD units 20 and 40 as described above (shown separately here). System 110 employs two or more high flux hemodialyzers, such as a venous dialyzer 42a and an arterial dialyzer 42b. In one embodiment, hemodialyzers 42a and 42b are relatively small, e.g., on the order of one quarter meter to three meters of membrane surface area. Dialyzers 42a and 42b are relatively high flux dialyzers, e.g., having a UF coefficient of eight milliliters of water diffused per hour per millimeters Hg pressure or greater (as used herein, the term "flux" refers to the above UF coefficient, which measures the ease of water transport through the membrane, expressed in milliliters/hour/millimeter Hg.

Variable restriction 56 placed between dialyzers 42a and 42b cause backfiltration in the venous dialyzer 42a of a relatively large portion of the fresh dialysate. The backfiltered dialysate and the fluid accumulated during the interdialytic period is ultrafiltered or removed from the patient 42 via the arterial dialyzer 42b. The fluid not backfiltered flows across the semi-permeable membranes in the arterial and venous dialyzers, enabling system 110 to provide both diffusive and convective removal of waste from the patient's blood.

As above, sterile dialysate is stored in bags or containers 12a to 12c (more than three solution bags may be used). System 110 employs volumetric dialysate pumps 24a to 24d that each operate with a flexible membrane 72 as described above to pump dialysate accurately. Here, flowrate and volume pumped are calculated based on a summation of pump chamber volumes per unit time or over time for dialysate pumps 24a to 24d.

System 110 of FIG. 10 illustrates two pumps 24a and 24b for a Pump Set 1 and two pumps 24c and 24d for a Pump Set 2. Alternatively, a single pump is used in place of each set of pumps, e.g., one to input dialysate to the dialyzers 42a and 42b and one to remove dialysate from the dialyzers and UF from the patient. That configuration however creates pulsatile or uneven flow, which may be less desirable. In the illustrated configuration, a first pump of each set is pulling fluid from the pump set's source, while a second pump of each set is pushing fluid towards the pump set's destination. After that set of pump strokes, the roles of the pumps in the respective sets alternate, so that the first pump (now full of fluid) pushes fluid towards the pump set's destination, while the second pump (now empty) pulls fluid from the pump set's source. The above cycle is repeated multiple times.

Pump Set 1 inputs fresh dialysate from bags 12a to 12c to dialyzers 42a and 42b of system 110 and Pump Set 2 removes a volumetric equivalent of the fluid pumped by Pump Set 1 and any extra fluid removed from patient 14 ("UF") during the course of the treatment. As illustrated, fresh dialysate is pumped via pumps 24a and 24b from sources 12a to 12c through to-dialyzer line 38a to the venous dialyzer 42a. A restriction 56 is located between venous dialyzer 42a and arterial dialyzer 42b. Restriction 56 builds pressure in venous dialyzer 42a, so that a relatively large amount of fresh dialysate entering venous dialyzer 42a is forced through the walls of the membranes inside venous dialyzer 42a and into the extracorporeal or blood circuit 102. The other portion of the fresh dialysate entering venous dialyzer 42a flows across the membranes inside venous dialyzer 42a, through restriction 56 and into arterial dialyzer 42b. Restriction 56 can be varied automatically to control back filtration.

Convective clearance occurs when a volumetric equivalent of the fluid backfiltered through venous dialyzer 42a is removed through return line 38b from the arterial dialyzer 42b. Also, a diffusive transport of toxins occurs across both dialyzers 42a and 42b due to a diffusive gradient that exists between blood within the dialyzers and blood path 102 and the dialysate flowing through the dialyzers. Over the total therapy, the total amount of fluid removed from the arterial dialyzer 42b is greater than the total amount of dialysate supplied to the venous dialyzer 42a, accounting for an amount of UF removal prescribed for the therapy.

In one example, pumps 24a and 24b of Pump Set 1 infuse eighteen liters of dialysate from sources 12a to 12c over two hours. Of that volume, one hundred ml/min of dialysate is backfiltered into the blood circuit 102 through the membrane walls of venous dialyzer 42a. Fifty ml/min of dialysate passes through the venous dialyzer 42a, restriction 56, and into venous dialyzer 42b. Pumps 24c and 24d of Pump Set 2 remove the total of eighteen liters of dialysate from dialyzer 42b and back into drain or bags 16, 18 and potentially 12a to 12c plus any desired amount of fluid from the patient. Over the example two hours, twelve liters (100 ml/min multiplied by 120 minutes) of dialysate is backfiltered into the patient's blood through the venous dialyzer 42a. Pumps 24c and 24d of Pump Set 2 remove that twelve liters, the six liters of dialysate that is not backfiltered into blood circuit 102 plus any fluid ultrafiltered from the patient.

The addition and removal of the twelve liters of dialysate from blood circuit 102 over the two hour therapy yields an overall convective removal according to the equation HF stdKt/V of ~2, which has been reported to be a suitable daily amount (see Jaber B T, Zimmerman D L, Leypoldt J K. *Adequacy of Daily Hemofiltration: Clinical Evaluation of Standard Kt/V (stdKt/V)*, Abstract Hemodialysis International Volume 7, number 1, p 80, 2003. Additionally, over the course of the example two hours, six liters of dialysate is used for diffusive clearance via the dialysate gradient across the membranes of dialyzers 42a and 42b. The dialysate flowrates and percent convective versus diffusive could be higher or lower than those used in the example.

Dialyzers 42a and 42b and flow restriction 56 may be attached to either HDF dialysate cassette 30b or blood cassette 44. Blood cassette 44 as seen includes at least a portion of the extracorporeal circuit 102. For example, in system 110 all of extracorporeal circuit 102 is integrated into cassette 44 with the exception of the arterial and venous tubing 52 and 54 going to and from the patient. HHD dialysate cassette 30b in turn provides a space efficient apparatus for handling the dialysate or therapy fluid flow portions of the pumps 24a to 24d and valves 86 described herein, which are actuated pneumatically or mechanically as desired. Cassettes 30b and 44 are well suited for home use, where space, capability and resources are limited.

In one preferred embodiment, HDF dialysate cassette 30b and blood cassette 44 and any associated attached tubing are gamma sterilized and sealed prior to use. Alternatively, sterilization via ethylene oxide or E-Beam is employed. The patient or operator opens a sealed wrapper just prior to use, inserts cassettes 30b and 44 (or single cassette for both) into PD and HD units 20 and 40, respectively (or single combined unit) for a single use and then discards the cassettes and associated tubing after use. While blood cassette 44 and HDF cassette 30b and respective flow paths 102 and 104 are intended for a single use in one embodiment, they could be reused with suitable disinfection and/or sterilization.

As seen in FIG. 10, beginning from the arterial access 52 of the patient 14, the extracorporeal or blood circuit 102 includes a pressure sensor 78, labeled PT1. PT1 is alternatively a pressure switch with the ability to stop blood flow prior to reaching blood pump 50. As a safety measure, system 110 in one embodiment includes a multitude of electrodes (shown in FIG. 11), such as two to four electrodes, which provide electrical contacts for an access disconnection sensor described for example in copending patent application entitled, "Conductive Polymer Materials And Applications Thereof Including Monitoring And Providing Effective Therapy", Ser. No. 10/760,849, filed Jan. 19, 2004, assigned to the assignee of the present disclosure, the entire contents of which are incorporated herein by reference. An alternative mechanism for detection of accidental needle disconnections is the use of a conductive blanket underneath the patient access. The presence of blood changes the conductivity of the blanket, causing an alarm and a stoppage of the pumps.

Blood pump 50 is a peristaltic pump in the illustrated embodiment and is located between pressure sensor PT1 and a drip chamber 82*a*, which has an integral pressure transducer 78, labeled PT2. The drip chambers 82*a* to 82*c* remove air from fluid passing through the drip chambers. One, a multiple of or all the drip chambers 82*a* to 82*c* in an alternative embodiment includes an associated level sensor 98. Sensors 98 are connected to or integrated into the associated drip chambers. Level sensors 98 sense and indicate the level or height of dialysate or therapy fluid in the. Each drip chamber 82*a* to 82*c* can also include a vent 44 and associated valve 86.

As discussed above in connection with FIG. 3, blood pump 50 is alternatively a volumetric pumping device (or otherwise the same type of pump as dialysate pumps 24*a* and 24*b*). Blood pump 50 can also be bidirectional for system priming and rinseback as discussed herein. Pressure sensor PT2 78 is alternatively not associated with a drip chamber, for example in a case in which pressure transducers associated with blood circuit 102 are used instead. Arterial and venous lines 52 and 54, pressure sensors PT1 and PT2, drip chambers 82*a* to 82*c* as well as the pathways for much of blood circuit 102 and tubing for peristaltic pump 50 are provided by or connected to blood cassette 44 in one embodiment.

After drip chamber 82*a*, blood flows out of cassette 44 and into a relatively small, high flux arterial dialyzer 42*b*. Arterial dialyzer 42*b* and venous dialyzer 42*a* are attached in one embodiment to a housing of blood cassette 44. In an alternative embodiment, the dialyzers are connected to HDF dialysate cassette 30*b* (or a single cassette for both blood and dialysate). Blood then flows from the arterial dialyzer 42*b* to the venous dialyzer 42*a*, back into blood cassette 44 and through a second drip chamber 82*b*. Drip chamber 82*b* also has an integral pressure sensor 78, labeled PT3. PT3 is alternatively provided without a drip chamber when, for example, pressure transducers coupled directly to blood circuit 102.

An air bubble detector 84 labeled ABD is located downstream from drip chamber 82*b* in blood circuit 102. A venous line clamp or valve 86, labeled V1, which may be cassette-based or provided externally to blood cassette 44, and which shuts down blood flow if detector 84 detects air in blood circuit 102, is located between the air detector 84 and arterial access 54, which returns cleansed blood to patient 14. An air level sensor (not illustrated) on drip chamber 82*b* is used alternatively or in addition to ABD 84.

To detect air in the blood, a level detect scheme is alternatively or additionally provided with drip chamber 82*b* or pressure transmitter 78, labeled PT3. For example, an ultrasonic sensor can be placed on opposite sides of the drip chamber. The ultrasonic sensor generates a signal that depends upon the percentage of air in the blood passing between transmitting and receiving portions of the sensor. Under normal operation, when no air is present, the blood within drip chamber 82*b* resides at a relatively steady level, although level fluctuations do occur due to changes in pressure, amount of blood pumped, etc. A threshold level of blood in chamber 82*b* does exist below which the blood should not drop. When air in the blood lines is present, the blood level in the chamber 82*b* is lower than threshold level, triggering an alarm from the alternative air/blood detector. It is important to note that an air detector and line clamp may be used additionally on the arterial side of blood circuit 102, if required for rinse, prime or blood rinseback, for example.

The dialysate flow path is also located primarily in HDF cassette 30*b* (or in a combined blood and dialysate cassette). The dialysate is supplied from dialysate supply bags 12*a* to 12*c*. In alternative embodiments (applicable to each of systems 10, 70, 80, 90, 100, 110 and 120), the dialysate source can be an on-line source or other type of non-prepackaged source. In systems 10, 70, 80, 90, 100, 110 and 120, a minimum of one infusion bag is provided, and in one preferred embodiment multiple bags, such as three sources 12*a* to 12*c* are provided. As discussed above, system 110 can also be provided with an empty drain or recirculation bag 18, which is filled with spent solution from the supply bag that is used first, and so on. Because the therapy in the end removes more fluid than is inputted, each of the supply bags 12*a* to 12*c* and recirculation bag is used to receive spent fluid and UF. The bag sequencing is controlled as illustrated by valves 86, labeled V2 to V8.

Dialysate flows from one of sources 12*a* to 12*c* to the volumetric diaphragm pumps 24*a* and 24*b* of Set 1. The volumetric accuracy of pumps is confirmed by monitoring. As discussed above, it is desirable to use two alternating solution delivery pumps 24*a* and 24*b* to limit the amount of pulsitile flow. As a safety measure, the diaphragms of each of the pumps 24*a* to 24*d* are configured so that if they leak, they can only leak externally. Any leaks collected externally from pumps 24*a* to 24*d* are then diverted towards a moisture sensor built into the cassette 30*b*, machine and/or cassette/machine interface, which senses such leak and signals: (i) an alarm; (ii) to shut down pumps 24*a* to 24*d* and 50; and (iii) to take any other appropriate action.

Referring now to FIG. 11, HDF system 120 employing balancing chambers (discussed in connection with FIG. 4) is illustrated. System 120 includes many of the same components described above, which are shown with like numbers that do not need to be re-described. Further, system 120 is shown in operation with the enhanced convection hemodialysis ("ECHD") dual high flux dialyzers 42*a* and 42*b* and variable restriction 56. It should be apparent however from the previous descriptions that system 120 can operate with any of the modalities described herein.

System 120 includes HD unit 40 and PD unit 20. In the illustrated embodiment, HD unit 40 operates with a blood cassette 44, which includes portions for valves 86, such as venous line 54 valve V1, drip chambers 82*b* and 82*c* (including pressure sensors 78 and vents 94). Tubing for blood pump 50 is also connected to blood cassette 44 in one embodiment as is tubing connected to the blood connectors of dialyzers 42*a* and 42*b*. Blood cassette 44 is also connected to a portion of arterial line 52 and venous line 54. Cassette 44 also defines valved blood flow pathways in fluid communication with the external tubing mentioned above.

HD unit 40 in one embodiment provides access disconnection points 140*a* and 140*b*, which sense and cause an alarm if an electrical condition changes due to an access disconnection of either arterial line 52 or venous line 54 from patient 14. HD unit 40 in the illustrated embodiment also houses or holds dialyzers 42*a* and 42*b* and flow restriction 56. In an alternative embodiment, PD unit 20 houses or holds those items. In a further alternative embodiment, HD unit 40 and PD unit 20 are combined into a single unit, which houses or holds those items.

In the illustrated embodiment, PD unit 20 operates with an HDF dialysate cassette 30*b*, which includes all or portions of fresh solution inlet pathways 122*a* and 122*b* (extending from supply line 32), spent solution inlet pathways 124*a* and 124*b* (extending from from-dialyzer line 38*b*), fresh solution outlet pathways 126*a* and 126*b* (feeding into to-dialyzer line 38*a*), and spent solution outlet pathways 126*a* and 126*b* (feeding into drain line 36). Pathways 122*a* and 126*a* communicate fluidly with a fresh compartment 130*a* of balance chamber 92. Pathways 124*a* and 128*a* communicate fluidly with a spent compartment 132*a* of balance chamber 92. Fresh compartment 130*a* and spent compartment 132*a* are separated by a flexible membrane 72 discussed above. Pathways 122*b* and 126*b* communicate fluidly with a fresh compartment 130*b* of balance chamber 94. Pathways 124*b* and 128*b* communicate fluidly with a spent compartment 132*b* of balance chamber 94. Fresh compartment 130*b* and spent compartment 132*b* are also separated by a flexible membrane 72.

In an embodiment, HDF dialysate cassette 30*b* supplies the fluid carrying portion of balance chambers 92 and 94. Balance chambers 92 and 94 may be referred to herein collectively as a flow equalizer. Suitable embodiments for incorporating balance chambers 92 and 94 into a cassette such, as HDF dialysate cassette 30*b* are disclosed in copending patent application referenced above. PD unit 20 provides rigid chambers into which the flexible components of balance chambers 92 and 94 of cassette 30*b* are positioned. PD unit 20 also provides pneumatic actuation in one embodiment to pull the outer sheets of balance chambers 92 and 94 apart so that inner flexible membranes 72 can be flexed back and forth by incoming fresh/spent and outgoing spent/fresh fluids, respectively.

In a first exchange cycle, one of the balance chambers 92 or 94 fills with fresh solution and at the same time delivers an equal volume of spent dialysate to drain. In that same first cycle, the other balance chamber 92 or 94 fills with effluent dialysate and at the same time pushes a like volume of fresh dialysate to dialyzers 42*a* and 42*b* or the patient according to the modality. Then, in a second cycle, the balance chambers 92 and 94 alternate functions so that the balance chamber that previously delivered fresh dialysate to the patient now delivers spent dialysate to drain, while the balance chamber that previously delivered spent dialysate to drain now delivers fresh dialysate to the dialyzer or patient. There is a short dwell time at the end of each exchange cycle when all valves are closed. The valves can be checked for leaks at this time.

In one embodiment (not illustrated), system 120 dedicates the flow equalizer or dual balance chambers 92 and 94 to removing an amount of fluid from the dialyzer, while at the same time filling the dialyzer with a like amount of fluid. Here, a separate UF pump or UF meter is used to remove a known amount of UF. In the illustrated embodiment, however, system 120 uses the flow equalizer or balance chambers 92 and 94 for UF removal as well as for balancing flow to and from dialyzers 42*a* and 42*b*. The valve operation for removing a net loss or ultrafiltration of fluid from the patient includes opening valves V1, V2, V6, V7, and V9, while closing valves V3, V4, V5, V8 and V10. This valve configuration pushes effluent dialysate to drain by pushing the fresh dialysate from balance chamber 94 to balance chamber 92.

System 120 enables an ultrafiltrate removal rate to vary over time, which is sometimes referred to as an ultrafiltrate profile. For example, if an ultrafiltrate cycle is performed on average after five exchange cycles to remove a desired amount of UF over the course of treatment, one could change the frequency at which ultrafiltrate is removed from the patient by increasing or decreasing the frequency of cycles during different times of treatment, but which average out to one UF stroke to every five exchange strokes. This could result, for example, in more fluid being removed during a first part of therapy than a second. The processor of control unit 26 is configured to run an algorithm, which enables the patient to select a profile, a treatment time and an overall volume to be removed. The algorithm automatically calculates an ultrafiltrate rate profile that achieves, according to the profile, an entered net cumulative ultrafiltrate volume over an entered treatment time. Those parameters may be entered alternatively through a patient data card or through a secure data connection.

In the illustrated embodiment, dialysate pumps 24*a* and 24*b* are peristaltic pumps. They may alternatively be membrane pumps or other types of pumps described herein. Tubes for dialysate pumps 24*a* and 24*b* in an embodiment are connected fluidly to appropriate valved pathways of HDF cassette 30*b*. Fresh dialysate pump 24*a* is shown upstream of heater 58. Alternatively, heater 58 is located upstream of pump 24*a*. Heater 58 can be of any suitable type, such as resistive, convective, radiant, and any combination thereof. Heater 58 is shown as being an in-line fluid heater. Heater 58 for any of the systems described herein can be inline or of a batch type, such as with the HomeChoice® APD system.

System 120 can also provide a bolus of solution to the patient when needed. Valves V2, V3, V7, V8 and V10 are opened and valves V1, V4, V5, V6 and V9 are closed. Pump 24*a* is run forcing one balance chamber bolus of dialysate and/or substitution fluid to the dialyzer or patient.

In any of the embodiments described herein, it is important that valves 86 of the systems are checked to ensure that they open and close properly. In one embodiment, the valves are checked periodically throughout treatment using conductive sensing. That is, if fluid escapes from the system via a faulty valve or tear in a cassette membrane, conductive sensors that measure a flow of electricity across a liquid can send an alarm and trigger appropriate action. Further, with cassettes 30*b* and 44, temperature sensing may be employed, for example, by applying a thermistor, IR sensor or thermocouple on one side of the sheeting of the cassette. Here, the temperature sensors are attached to PD and HD units 20 and 40 and, for example, contact the sheeting membrane so as to obtain a quick reading of the temperature of the dialysate or blood.

The above described systems show multiple embodiments for performing a combination therapy including any one or more of peritoneal dialysis, hemodialysis, hemofiltration and hemodiafiltration. The embodiments also show different pumping technologies that can be used for any of these. The embodiments enable a dialysis patient to alternate from PD to HD in the same week or even the same day if desired. The tradeoff is that a patient is willing to accept and perform a dual access, namely, one for PD and one for HD.

The hybrid therapy allows the patient to take advantage of beneficial characteristics for each of PD and blood treatment such as HD, HF and HDF, while minimizing less desirable traits of each. For example, with PD, an osmotic agent, e.g., glucose, is needed to perform UF. The osmotic agent is believed to cause gradual (diffusive) deterioration of the peritoneal lining. HD on the other hand can accurately achieve UF without use of an osmotic agent. HD extracts UF directly from the blood. With HD however blood is pulled from the body and is exposed to inner and foreign surfaces and pressure involved with the pumping of the blood. In many cases, HD therapy requires the addition of anticollagens, such as hyperion, into the blood to keep blood from congealing within arterial line 52, venous line 54 and dialyzer 42.

The above described systems enable the patient to take advantage of HD's ability to control UF without an osmotic agent and PD's ability to remove solutes without removing blood from the patient. Here, it is contemplated to perform PD using a psychologically stable solution in the absence of an osmotic agent. Accordingly, the gradual detrimental effects due to PD would not occur. This would allow PD patients to remain on PD for a longer period of time. The PD solution would take advantage of the concentration ingredient of solute, e.g., creatinine, urea, uric acid, etc. In essence, PD is used to perform necessary clearance of impurity that build up within the patient due to the patient's kidney failure. HD or one of the blood treatments are then performed to provide the necessary ultrafiltration. In this manner, the blood treatment can be performed as quickly and safely as possible because its primary purpose is to remove UF. In this manner, the amount of time the patient spends performing HD could be minimized, thereby minimizing the amount of time that blood is external to the patient's body.

As described herein, in one preferred embodiment, HD unit 40 is provided separately from PD unit 20. In this manner it is contemplated to provide a PD unit 20 that stands alone to perform peritoneal dialysis. If it is desired to perform a blood treatment additionally or alternatively to the PD therapy, then the HD unit 40 can be added. Providing separate units creates various issues related to electromechanical architecture, which are now addressed.

Control Architecture

Figure 12D:
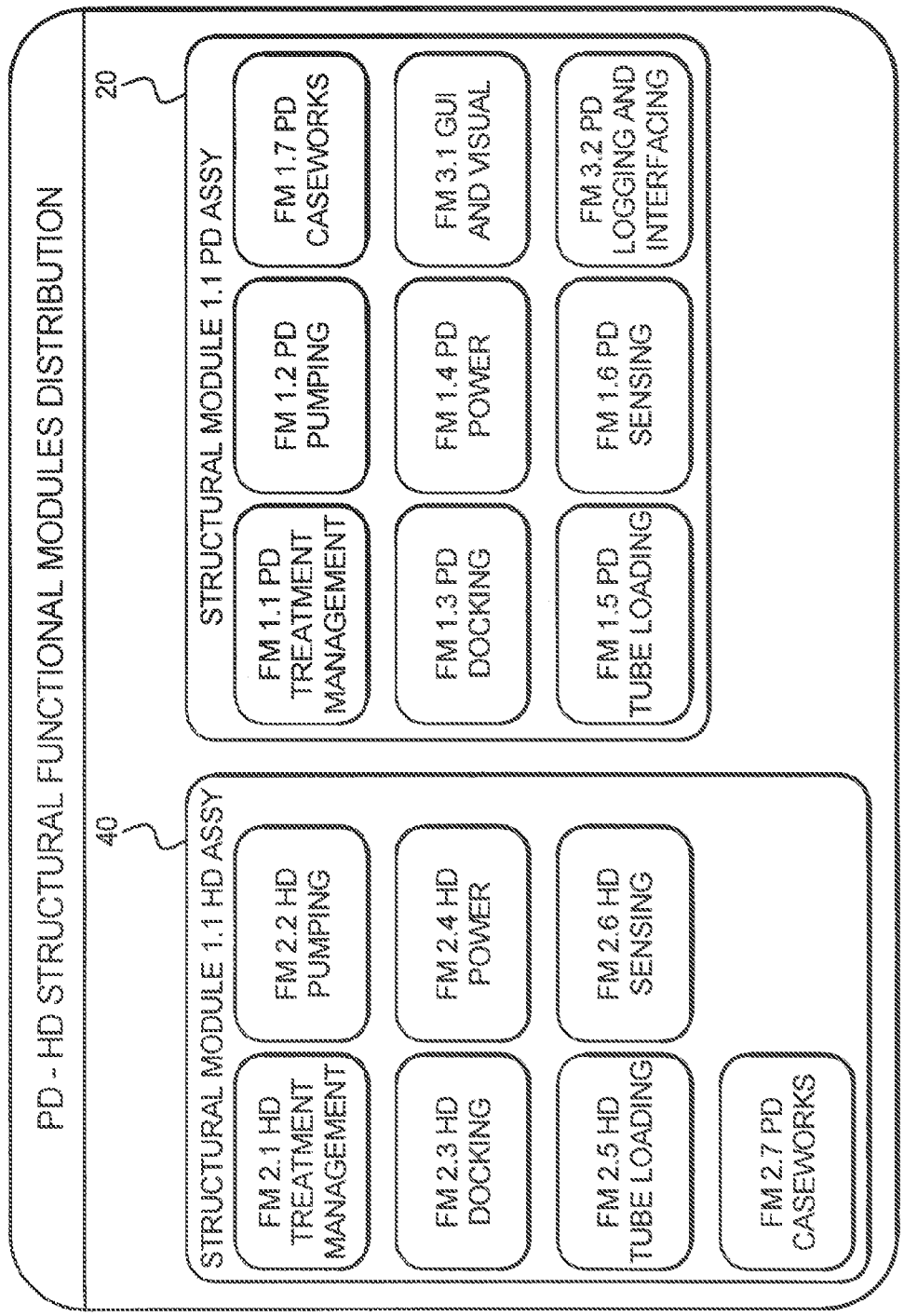
FIG. 12D schematically illustrates one embodiment of the software modules used for the control architecture of the PD systems having blood treatment options described herein.

Referring now to FIGS. 12A to 12G, various system architectures for the systems described herein are illustrated. FIG. 12A illustrates various external factors or logistics affecting the PD/HD control architecture described below. The systems described herein are configurable to be used at home, in which case the user of the system can be the same as the patient. Alternatively, the systems described herein are configurable to be used in a center or at home, but wherein the system is operated by someone other than the patient, e.g., a clinician, nurse, doctor or family member. The systems typically have to accommodate dialysate supply bags and other supply bags for HD (or other type of blood therapy described herein), such as heparin (or other anticoagulant) and saline (for priming and blood rinseback). It is also contemplated that the systems in an HD or HDF mode use dialysate made online instead of bagged dialysate. The systems also have to accommodate both PD and HD disposable sets including the relevant disposable cassette and associated tubing. HD can use separate dialysate and blood cassettes or a single cassette for both the flow of dialysate and blood.

FIG. 12B illustrates one embodiment of a disposables architecture for the HD and PD units 40 and 20 in connection with the various systems described herein. Each unit includes its own disposable set including an associated disposable cassette and associated tubing. For example, PD unit 20 operates a dialysate cassette 30, which can be configured for PD as cassette 30a or for HD as cassette 30b as described in detail herein.

When PD is performed, tubing associated with dialysate cassette 30a includes patient line 34, one or more supply line 32 and drain line 36 (see, e.g., FIG. 1). Depending on the type of dialysate heating employed, the associated tubing can also include a to- and from-heater line.

When HD is performed, tubing associated with dialysate cassette 30b includes to- and from-dialyzer lines 38a and 38b, one or more supply line 32 and drain line 36 (see, e.g., FIG. 1). Again, depending on the type of dialysate heating employed, the associated tubing can also include a to- and from-heater line. Further, when HD is performed a separate (or integrated) blood cassette 44 is also provided as shown in detail below. Tubing associated with blood cassette 44 includes arterial and venous lines 52 and 54, dialyzer blood lines 48a and 48b and prime and rinseback line 28.

FIG. 12C schematically illustrates various embodiments for a power supply architecture for PD unit 20 and HD unit 40. In FIG. 12C, each unit or system 20 and 40 includes a separate supply of power 112, e.g., an alternating current supply. It should be appreciated however that the power supply 112 is alternatively a direct current power supply. Further alternatively, universal power supplies 112 can be formatted for operating with 120 VAC or 240 VAC mains voltage as needed. In one embodiment, power supplies 112 are identical for both PD units 20 and HD unit 40.

AC power 112 feeds a power supply unit 114, which in one embodiment is the same for both PD unit 20 and HD unit 40. In an embodiment, power supply unit 114 converts the input voltage 112 to a desired type and level. The dual power supply arrangement alleviates problems due to electromagnetic interference ("EMI"), electromagnetic compatibility ("EMC") and electrostatic discharge ("ESD"), which could otherwise occur by using the same power unit 114 for both PD unit 20 and HD unit 40. Using the same power supply 114, one each for PD and HD units 20 and 40, simplifies design and manufacturing costs.

It is also contemplated however to use a single AC power supply 112 and power supply unit 114 if it is believed that conductive path problems will be minimal or can be minimized. The single supply configuration reduces hardware and potentially software otherwise associated with two separate power supplies.

As discussed above, in one embodiment HD unit 40 and PD unit 20 communicate via a non-electrical or wireless mode 60 of transmission. This also alleviates problems due to EMI, EMC and ESD, which can create problems at the design level because of possible conduction paths that a hard-wired linking of PD unit 20 and HD unit 40 can create. The wireless communication 60 can be of any suitable type, such as RF, encoded RF, secured Bluetooth, microwave, infrared or others.

In the illustrated embodiment, PD unit 20 is linked electromechanically with a graphical user interface ("GUI") 116. It should be appreciated however that HD unit 40 can also be connected to a separate GUI 116. In one embodiment, GUI 116 enters and provides information for any of the treatments discussed herein including PD and/or blood treatments. In this manner, the user does not have to learn or become familiar with a new interface when adding a blood therapy to PD unit 20. To this end, in one embodiment software within PD unit 20 looks for a connection via data link 60 to HD unit 40. Upon sensing the presence of HD unit 40, data link 60 triggers additional and/or different software, so that PD unit 20 enables the HD functions of GUI 116. Allowing the PD module to be the primary module in the PD unit 20/HD unit 40 combination also reduces the amount of mechanical integration needed.

GUI 116 in an embodiment operates with a touch screen, membrane switches, dials, other mechanical switches and any combination thereof. GUI 116 can also be foldable so that the screen collapses into the machine for protection during travel or when not in use.

FIG. 12D illustrates different software modules that can run an interchangeable PD or HD therapy. When PD treatment is used, only the software associated with PD unit 20 is needed. When HD is performed, software modules for both PD unit 20 and HD unit 40 are used. PD software includes a treatment management module FM 1.1 PD, which includes software configured to control the overall dialysate treatment, e.g., dialysate temperature control, air handling, patient alarms, safety control, etc. For example, treatment management module FM 1.1 PD can run a part or all of the dialysate portions of the routines shown below in connection with FIGS. 19 to 22.

Module FM 1.2 PD includes software configured to control parameters related to dialysate pumping, such as, dialysate pumping speed, ultrafiltration control, dialysate line priming, dialysate line occlusion correction, etc. Module FM 1.2 PD can interface with other modules, for example, sensing module FM 1.6 PD to receive flowrate feedback for example to maintain one or more dialysate pump at a desired speed. In another example, pumping module FM 1.2 PD interfaces with sensing module FM 1.6 PD, such that when the sensing module detects air in the system, the pumping module stops pumping dialysate to the patient or dialyzer or shunts the air laden dialysate to drain. In another example, pumping module FM 1.2 PD interfaces with sensing module FM 1.6 PD to run an occlusion correction routine when the sensing module detects a low or occluded flow or overpressure condition.

PD dialysis pumping module FM 1.2 PD also interfaces with treatment management module FM 1.1 PD, which in a pure PD mode tells the dialysate pumping module when the dialysate pump(s) should be pumping dialysis fluid to the patient, be in a dwell state, or to pump effluent or spent dialysate from the patient to drain. PD mode pumping also includes PD priming, line occlusion correction, air correction, etc.

When in HD dialysis mode, treatment management module FM 1.1 PD can for example tell pumping module FM 1.2 PD when it is proper to begin pumping. Also, HD dialysate will be pumped typically at a higher pressure than for PD. The dialysate pumping is adjusted accordingly for HD. Further, it is known to run ultrafiltration profiles for HD. The ultrafiltration profiles can be stored for example on treatment management module FM 1.1 PD, which then interfaces with pumping module FM 1.2 PD to tell the pumping module how much ultrafiltration to remove at a given point during therapy. The modules can interface in a similar manner for sodium profiling.

Module FM 1.3 PD includes software configured to control parameters related to docking, e.g., when HD unit 40 is docked to PD unit 20 via data link 60 as described above in connection with FIG. 12C. In one embodiment, the architecture is set at a default to run a pure PD treatment. That is, the system is caused to run software that looks for a PD dialysate cassette 30a, runs PD dialysate pumping routine and does not look for blood cassette 44 or to run a blood pumping routine.

When a separate HD unit is docked to the PD unit (see e.g., FIG. 13B for integrated HD unit 40, here docking software is triggered when HD cassette 44 is installed; see alternatively FIGS. 18C to 18E when separate HD unit 40 is docked to PD unit 20), docking module FM 1.3 PD senses the additional HD hardware and causes PD unit 20 to run a HD therapy instead of a PD therapy. That is, the system is caused to run software that looks for an HD dialysate cassette 30b, runs an HD dialysate pumping routine and also looks for blood cassette 44 and runs a blood pumping routine.

Module FM 1.4 PD includes software configured to control parameters related to powering PD unit 20. Particulars for powering PD unit 20 are discussed above in connection with FIG. 12C.

Module FM 1.5 PD includes software configured to control parameters related to the loading of the disposable for PD unit 20. As discussed above, the system is set in one embodiment at a default to look for PD cassette 30a and associated tubing. If HD unit 40 is docked, module FM 1.5 PD instead runs software for HD cassette 30b and associated tubing. Module FM 2.5 HD runs software for controlling HD cassette 44 as discussed below. Alternatively, the HD cassette software can be located at module FM 1.5 PD as discussed in connection with FIG. 12E.

Module FM 1.6 PD includes software configured to control parameters related to sensing for PD unit 20. Sensing PD dialysis parameters includes, for example, sensing PD dialysate pump speed and pressure, PD dialysate temperature, air sensing, conductivity sensing, volumetric sensing (e.g., for total fluid flow and ultrafiltration), etc. As discussed above, the system is preset to sense PD parameters, e.g., enable readings from PD sensors and use parameter setpoints associated with a PD treatment. If HD unit 40 is docked, module FM 1.6 PD instead runs software for HD dialysis sensing. Many of the same parameters listed above for PD dialysate sensing are also sensed for the HD therapy. One difference with HD versus PD is that HD looks for a leaking dialyzer by checking dialysate return line 38b for the presence of blood. Another difference for HD dialysate sensing is the monitoring of sodium level in the dialysate. Module FM 2.6 HD runs software for sensing parameters relating to blood pumping as discussed below. Alternatively, the HD blood flow software can be located at module FM 1.6 PD.

Module FM 1.6 PD interfaces with other modules (as do many of the dialysate modules), such as treatment management module FM 1.1 PD and PD dialysis pumping module FM 1.2 PD. The interfacing of different modules is performed for example via a central processing unit ("CPU") or other one or more supervisory processor located on PD unit 20. The CPU for example runs treatment management module FM 1.1 PD.

Caseworks module FM 1.7 PD refers to the frame or enclosure of the PD unit 20. The enclosure can include lights or other electrical devices mounted to the enclosure, which require electrical power. Caseworks module FM 1.7 PD also includes electrical insulation and radiation shielding associated with PD unit 20.

GUI module FM 3.1 GUI resides on PD unit 20 and in one embodiment controls GUI 116 for both PD and HD treatments as described above in connection with FIG. 12C. Module FM 3.1 GUI includes a video card and a sound card if necessary to display information and graphics and to provide audio instructions or alarms if desired. It is also contemplated to have module FM 3.1 GUI run patient voice guidance software to receive certain information from the patient via voice command.

Module FM 3.2 PD includes software configured to control parameters related to logging onto and interfacing with PD unit 20, e.g., via a computer directly, via a wireless network connection, or via a wired data network, such as an Ethernet, intranet or internet. Module FM 3.2 PD can be used by a hospital or clinician for diagnostic purposes, to monitor treatment effectiveness, to set parameters, etc. For example, certain parameters can be set in the routines of FIGS. 19 to 22 via module FM 3.2 PD. Module FM 3.2 PD is configured to enter data and provide data concerning PD and HD treatments.

FIG. 12D also illustrates software modules that run the blood pumping of HD unit 40. The HD modules can be located physically on PD unit 20, for example, if HD unit 40 is located within the same housing as PD unit (see, e.g., FIGS. 12E, 13A and 13B). Alternatively, the HD modules are located physically on HD unit 40, for example, if HD unit 40 is a separate unit that is docked to PD unit 20 (see, e.g., FIGS. 12F and 18A to 18G).

HD software includes a treatment management module FM 2.1 HD, which includes software configured to control the blood pumping portion of an HD or blood therapy treatment, e.g., to control blood temperature control, air in blood handling, blood patient alarms, blood safety control, etc. For example, treatment management module FM 2.1 HD can run the blood pumping portion of the HD routines shown generally below in connection with FIGS. 19 to 22.

Module FM 2.2 HD includes software configured to control parameters related to blood pumping, such as, blood pumping speed, blood line priming, blood rinseback, etc. Module FM 2.2 HD can interface with other modules, for example, sensing module FM 2.6 HD to receive flowrate feedback for example to maintain the blood pump at a desired speed. In another example, pumping module FM 2.2 HD interfaces with sensing module FM 2.6 HD, such that when the sensing module detects air in the extracorporeal system, the blood pumping module stops pumping or shunts the air laden blood to drain. In a further example, blood pumping module FM 2.2 HD interfaces with sensing module FM 2.6 HD to stop the blood pump when the sensing module detects that a venous (more serious) or arterial (less serious) needle or cannula access disconnection has occurred. Still further, blood pumping module FM 2.2 HD interfaces with sensing module FM 2.6 HD to stop the blood pump when the sensing module detects that the patient has become hypotensive, e.g., when the dialyzer becomes clogged due to low blood fluid volume.

Blood pumping module FM 2.2 HD also interfaces with treatment management module FM 2.1 HD, which tells the blood pumping module when the blood pump should be pumping blood, running a priming or rinseback routine, etc.

Module FM 2.3 HD includes software configured to control parameters related to docking, e.g., when HD unit 40 is docked to PD unit 20 over a data network 60 shown in FIG. 12C. Here, HD unit 40 can for example include a handshaking routine that informs HD unit 40 that PD unit 20 recognizes that the HD unit 40 has been docked to the PD unit. HD unit 40 can also check to make sure that it has been docked properly, e.g., that all data lines are working properly (for hardwired connection) or that a wireless communication is functioning properly. This function can alternatively or additionally be performed via dialysate docketing module FM 1.3 PD. As shown below in connection with FIG. 12F, docking modules FM 1.3 PD and FM 2.3 HD in one embodiment operate via data network 60 to interface between the CPU's of PD device 20 and HD device 40.

Module FM 2.4 HD includes software configured to control parameters related to powering HD unit 20. Particulars for powering HD unit 20 are discussed above in connection with FIG. 12C.

Module FM 2.5 HD includes software configured to control parameters related to the loading of the disposable for HD unit 20. Module FM 2.5 HD runs software for controlling HD cassette 44, which for example determines whether the peristaltic pump tubing has been loaded properly around the race of blood pump 50. Module 2.5 also operates the valves of HD cassette 44 or occluders operating with tubes connected to HD cassette 44. Module FM 2.5 HD can also check that blood pressure sensing areas of HD cassette 44 are positioned properly with arterial and venous pressure sensors located within blood unit 40. In a similar manner, HD cassette 44 can include an air separation or drip chamber that operates with a level detector located within blood unit 40. Disposables module FM 2.5 HD can therefore further look to ensure that the level detector is aligned properly with the drip chamber of the cassette. Still further, module FM 2.5 HD can interface with sensing module FM 2.6 HD (discussed next) to ensure that patient access has been made properly.

Sensing module FM 2.6 HD includes software configured to control parameters related to sensing for HD unit 40. Sensing HD dialysis parameters includes for example sensing blood pump speed, arterial and venous blood pressure, blood temperature, air in the blood, venous and possibly arterial access disconnection. Sensing module FM 1.6 HD can also calculate and monitor transmembrane pressure ("TMS") at the dialyzer. Sensing module FM 2.6 HD interfaces with other modules (as do many of the HD modules), such as treatment management module FM 2.1 HD and HD dialysis pumping module FM 2.2 HD. The interfacing of different modules is performed for example via a central processing unit ("CPU") or other one or more supervisory processor located on blood unit 40. The CPU of blood unit 40 in one embodiment runs the HD treatment management module FM 2.1 HD.

Caseworks module FM 2.7 HD refers to the frame or enclosure of the HD unit 40. The HD enclosure can include lights or other electrical devices mounted to the enclosure, which require electrical power. Caseworks module FM 2.7 HD also includes electrical insulation and radiation shielding associated with HD unit 40.

Figure 12E:
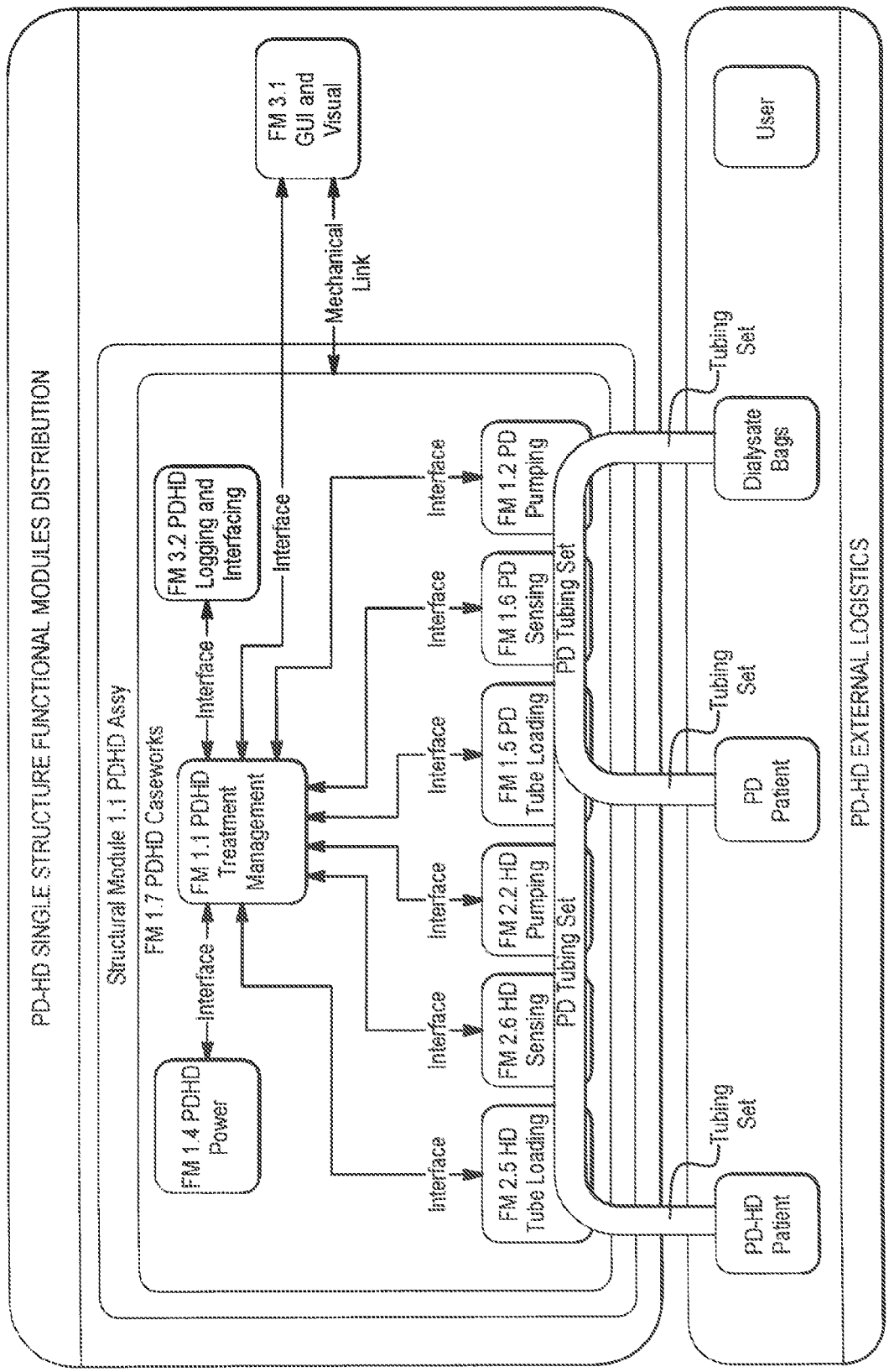
FIG. 12E schematically illustrates one embodiment of a single PD/HD distribution of software modules used for the control architecture of the PD systems having blood treatment options described herein.

Referring now to FIG. 12E, a single PD/HD structure functional modules distribution is illustrated. In FIG. 12E, virtually all control is located on PD unit 20, with HD unit 40 having for example a simple connector for receiving power wires from PD unit 20, which power various components within HD unit 40 at appropriate times and at appropriate levels (e.g., vary power to blood pump as needed). Alternatively, HD unit 40 includes low level controllers, e.g., motor and pinch valve controllers, which receive commands from PD unit 20 for operation. All interfacing between modules is done at the PD unit 30 (e.g., via one or more CPU at PD unit 30). All sensor evaluation is done at PD unit 30.

An advantage of the architecture of FIG. 12E is that high level control is simplified and centralized. The docking modules are eliminated and communication between PD unit 20 and HD unit 40 is simplified, perhaps making wireless control easier. Further, HD unit 40 here is likely a less expensive option. A drawback of the single system is that additional functionality, firmware, software and hardware has to be installed in PD unit 20, which may never be used if the patient never uses the HD option.

In the single distribution architecture of FIG. 12E, treatment management module for HD (FM 2.1 HD) is eliminated and treatment management module for PD (FM 1.1 PD) is expanded to control treatment management for both modalities (FM 1.1 PD/HD). Bi-treatment management module FM 1.1 PD/HD interfaces with GUI module FM 3.1 GUI described above as operating with GUI 116. Bi-treatment management module FM 1.1 PD/HD also interfaces with integrated power module FM 1.4 PD/HD, which powers both PD unit 20 and HD unit 40. Bi-treatment management module FM 1.1 PD/HD further interfaces with integrated logging and interfacing module FM 3.2 PD/HD, which as described above allows remote or wired bi-directional data interfacing with both PD module 20 and HD module 40 in this case.

Bi-treatment management module FM 1.1 PD/HD also controls individual modules for both dialysate and blood flow described above including (i): HD tube loading module FM 2.5 HD, (ii) HD sensing module FM 2.6 HD, (iii) HD pumping module FM 2.2, (iv) PD tube loading module FM 1.5 PD, (v) PD sensing module FM 1.6 PD, and (vi) PD pumping module FM 1.2 PD. The individual modules are capable of operation with any logistical requirement (including associated disposables) for a PD/HD patient, pure PD patient, using dialysate bags or online fluid, and allowing for the patient to operate the system at home or for another uses to operate the system at home or outside the home.

Figure 12F:
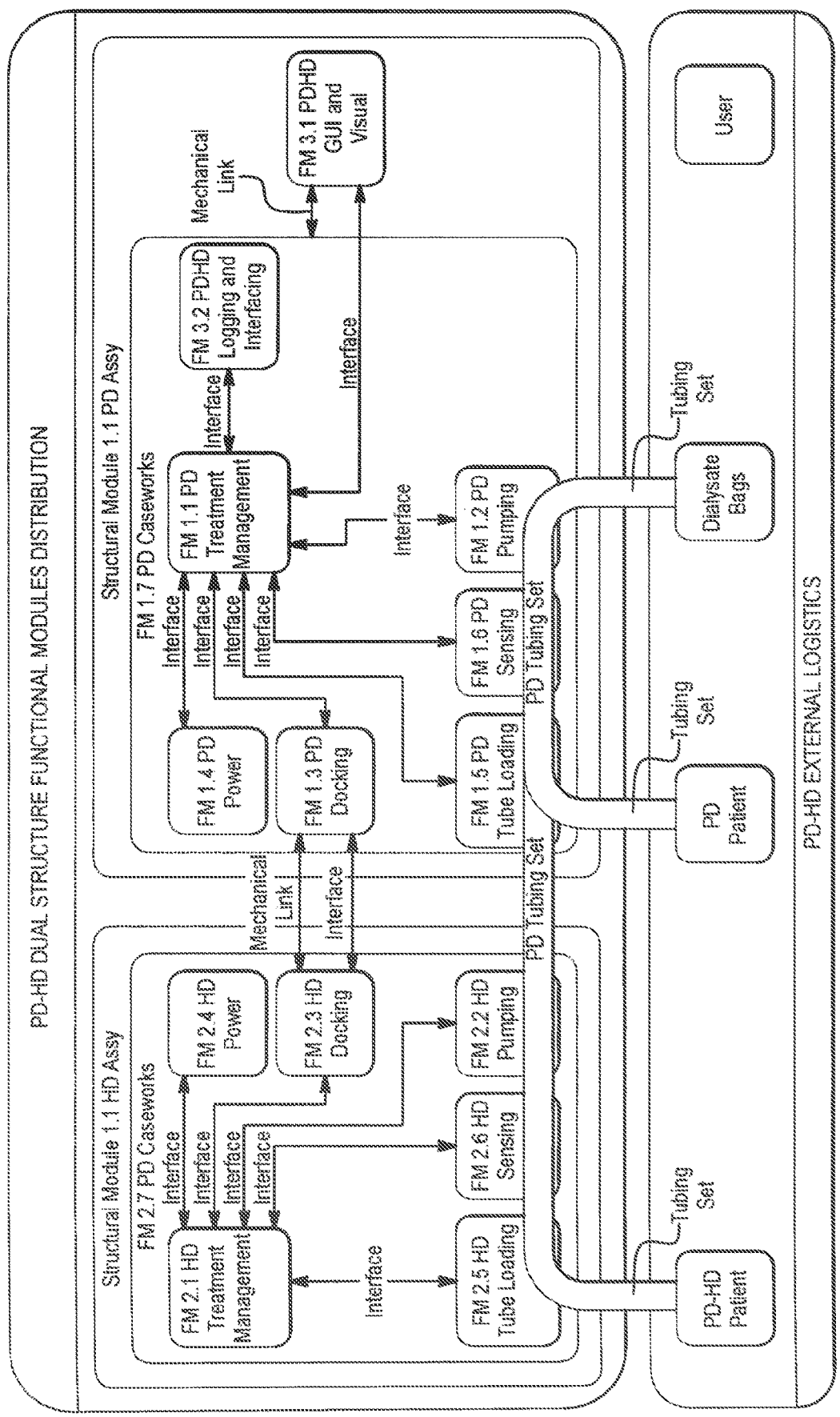
FIG. 12F schematically illustrates one embodiment of a dual PD/HD distribution of software modules used for the control architecture of the PD systems having blood treatment options described herein.

Referring now to FIG. 12F, a dual PD/HD structure functional modules distribution is illustrated. In FIG. 12F, virtually all blood control is located on HD unit 40, with PD unit 20 controlling dialysate flow for either PD or HD. Here, blood pump unit 40 receives its own power, monitors its own sensing and tube loading and controls its own pumping. Here also, the docking modules are required for communication between units 20 and 40.

An advantage of the dual architecture of FIG. 12F is that high level blood control is not present until needed with HD unit 40. Advantages of having separate power supplies is discussed above in connection with FIG. 12C. Correcting a problem with blood flow control can also be easier because HD unit 40 can likely just be swapped-out, allowing PD unit 20 to be used in the meantime and without having to replace or fix PD unit 20 due to a problem with HD unit 40.

Drawbacks with of the dual architecture of FIG. 12F include increased complexity due to the dual high level control and enhanced data exchange. The dual architecture of FIG. 12F also likely increases firmware, software, hardware, and cost if the patient uses the HD option.

Even with the dual architecture, a single integrated GUI module FM 3.1 PD/HD is used in one embodiment. This is advantageous to the user who uses the same GUI 116 regardless of the therapy mode. Even though different screens and parameters will be different for different treatments, the same physical display, with the same controls, screen layouts and feel should make the user more comfortable when learning the HD option. Further, only one integrated logging and interfacing module FM 3.2 PD/HD is needed because blood data can be sent and received through the PD unit via the docking interface of the PD unit 20 and HD unit 40.

In the dual distribution architecture of FIG. 12F, PD treatment management module for FM 1.1 PD: (i) interfaces with GUI module FM 3.1 GUI PD/HD, (ii) interfaces with PD power module FM 1.4 PD, (iii) interfaces with integrated logging and interfacing module FM 3.2 PD/HD, (iv) controls PD tube loading module FM 1.5 PD, (v) controls PD sensing module FM 1.6 PD, and (vi) controls PD pumping module FM 1.2 PD.

PD treatment management module for FM 1.1 PD also interfaces with PD docking module FM 1.3 PD, which in turn communicates via wired connection or wirelessly with HD docking module FM 2.3 HD, allowing PD treatment management module FM 1.1 PD to share data with HD treatment management module FM 2.1 HD.

In the dual distribution architecture of FIG. 12F, HD treatment management module for FM 2.1 HD: (i) interfaces with HD power module FM 2.4 HD, (ii) controls HD tube loading module FM 2.5 HD, (iii) controls HD sensing module FM 2.6 HD, and (iv) controls HD pumping module FM 2.2.

The individual PD and HD modules are again capable of operation with any logistical requirement (including associated disposables) for a PD/HD patient, pure PD patient, using dialysate bags or online fluid, and allowing for the patient to operate the system at home or for another uses to operate the system at home or outside the home.

Hardware

Figure 13A:
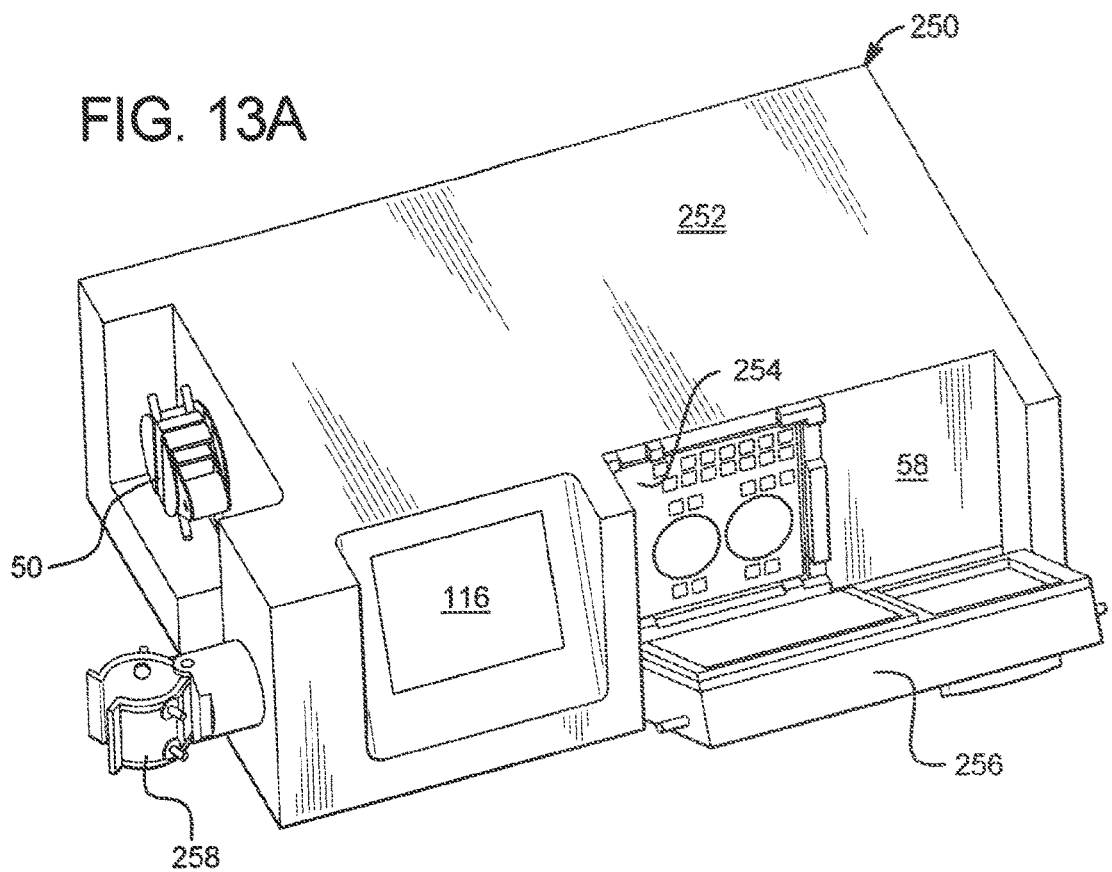
FIG. 13A and FIG. 13B are perspective views of one embodiment of a combined PD/HD system with dialysate and blood cassettes for a blood treatment therapy not loaded and loaded, respectively.
Figure 13B:
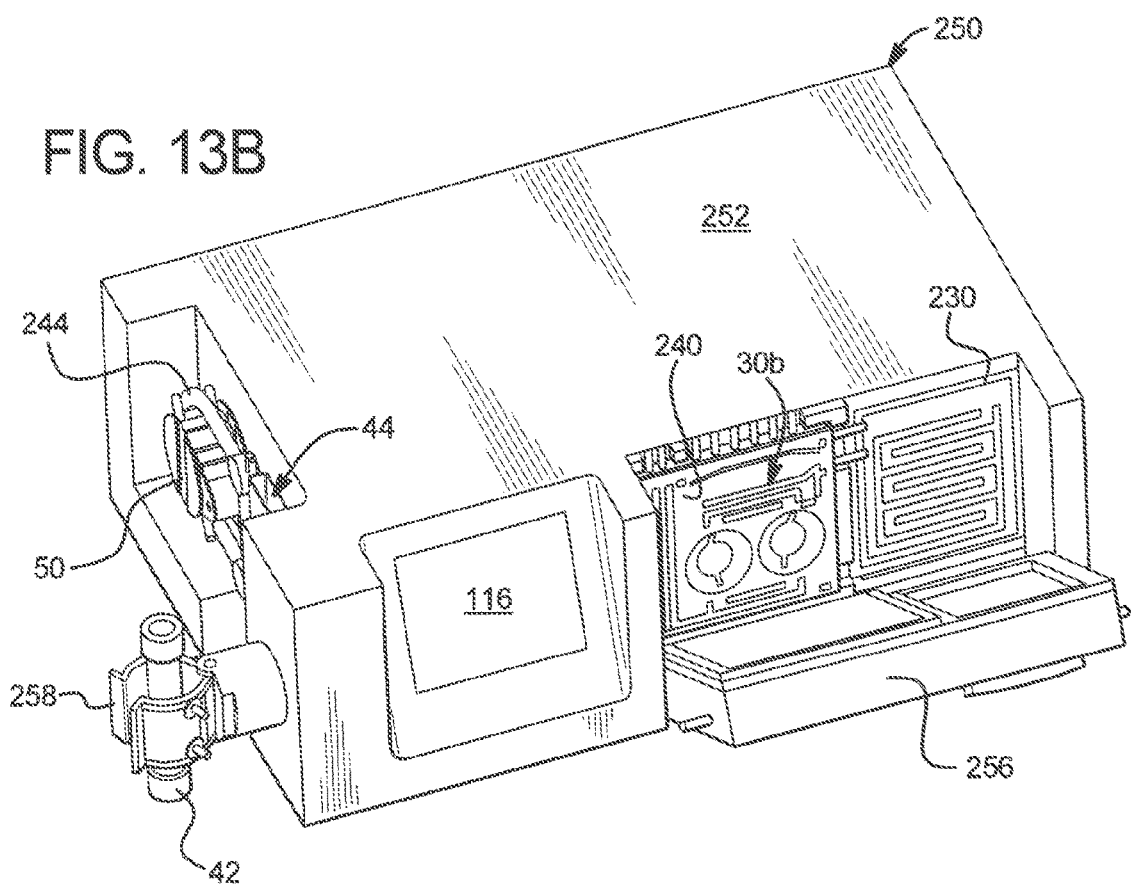

Referring now to FIGS. 13A, 13B, 14A, 14B, 15, 16A, 16B, 17A and 17B, one embodiment for a combined PD/HD system is illustrated by system 250. Here, HD unit 40 is integrated into PD unit 20 to form integrated PD/HD system 250. A similar system in which HD unit 40 is separate from PD unit 20 is shown below in connection with FIGS. 18A to 18E. While system 250 is shown as being integrated, the teachings applicable to PD and HD dialysate cassettes 30a and 30b shown below (and the fact that the dialysate portion of the HD cassette and the dialysate cassette of the PD system can be loaded into the same part of the machine system 250) are applicable whether or not the system is integrated, as here, or whether separate PD and HD units 20 and 40 are provided (FIGS. 18A to 18E). As seen in FIGS. 13B and 15, blood cassette 44 is separated from the dialysate HD cassette 30b, such that blood cassette 44 (and associated blood pump 50) can be mounted on a separate HD unit 40 or the integrated system 250 as desired.

Figure 14A:
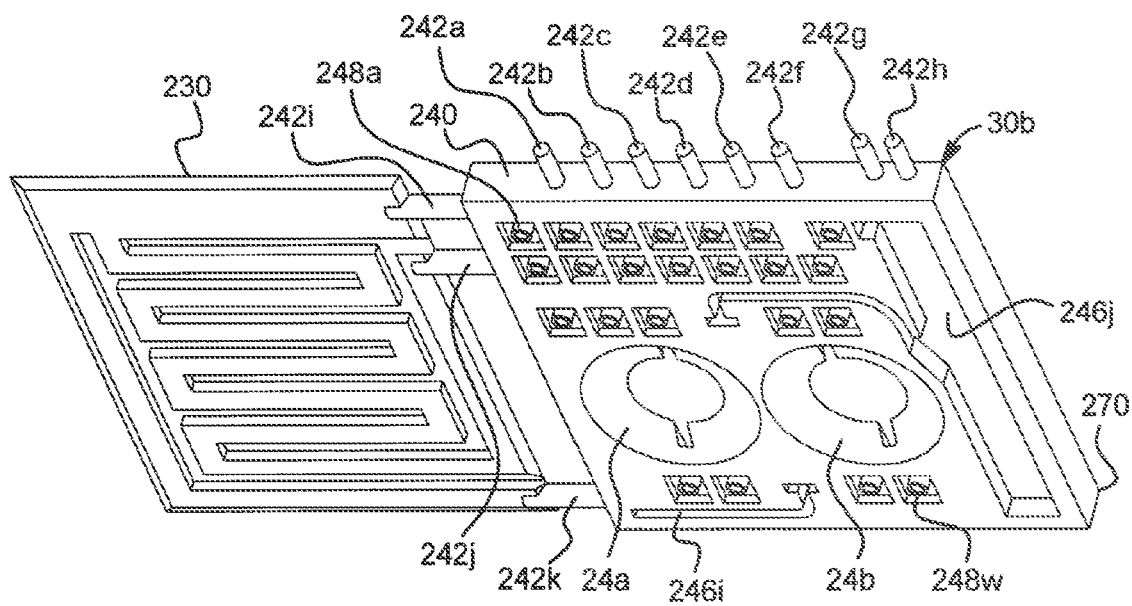
FIGS. 14A and 14B are perspective views of one embodiment of a dialysate side cassette for the system of FIGS. 13A and 13B.
Figure 14B:
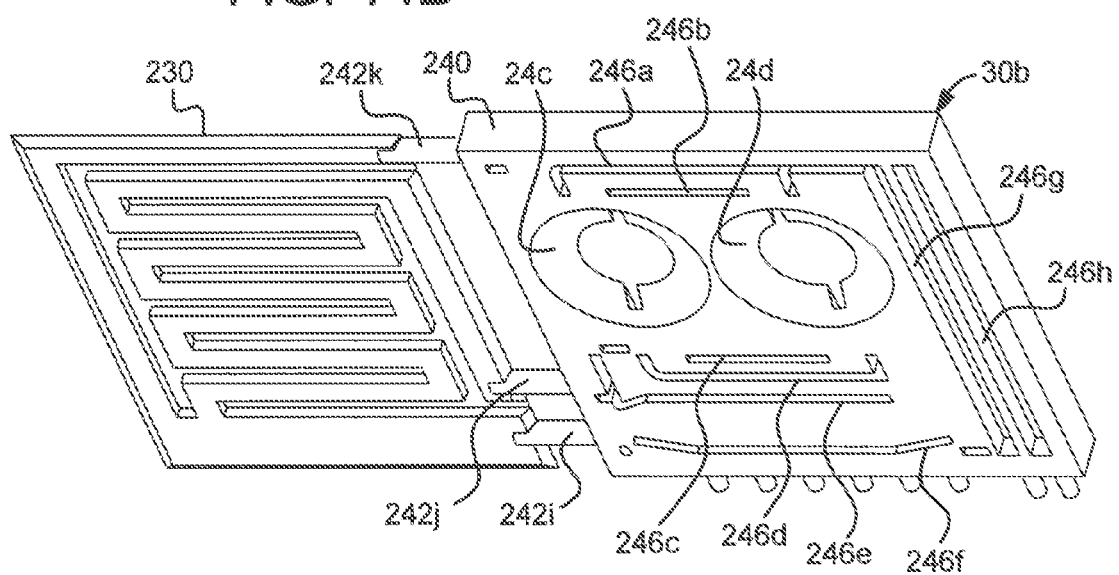

System 250 includes a housing 252 and GUI 116 described above in connection with FIG. 12. Housing 252 includes a cassette interface 254 which interfaces interchangeably with HD dialysate cassette 30b and PD dialysate cassette 30a. Housing 252 connects hingedly to door 256, which compresses HD cassette 30b or PD cassette 30a in place against cassette interface 254. As seen in FIGS. 14A and 14B, both HD cassette 30b and PD cassette 30a include or are attached to an inline heating path 230. Hinged door 256 also compresses inline fluid heating pathway 230 against a heater 58 built into housing 252 of integrated system 250.

FIGS. 13A and 13B show a system 250 with blood pump 50 and dialyzer holder 258 installed. As seen in FIG. 13B, dialyzer holder 258 clamps onto and holds dialyzer 42 when integrated machine 250 is to be used for a blood treatment, such as hemodialysis. Also, FIG. 13B shows HD or blood treatment cassette 44 installed, such that pump tubing 244 of cassette 44 is placed around and in operable communication with blood pump 50.

FIGS. 14A and 14B illustrate HD disposable dialysate cassette 30b. Valve and pump portion 240 includes ports 242a to 242h. In one implementation, port 242a is a drain port, port 242b is a supply 1/drain 2 port, port 242c is a supply 2/drain 3 port, port 242d is a supply 3/drain 4 port, port 242e is a supply 4/drain 5 port, port 242f is a supply 5 port, port 242g is a from-dialyzer port and port 242h is a to-dialyzer port. Ports 242a to 242h interface with flow paths 246a through 246j shown on the front and reverse sides of valve and pump portion 240 of cassette 30b.

Cassette 30*b* includes an attached fluid heating pathway 230 as discussed above, which attaches to a valve and pump portion 240 of cassette 30*b* via ports 242*i* to 242*k* as shown. In one implementation, port 242*i* is a vent port, port 242*j* is a to-heater port and port 242*k* is a from-heater port.

Valve and pump portion 240 in an embodiment is made of a rigid material, such as polyvinyl chloride ("PVC"), acrylic, ABS, polycarbonate, polyolefin blends, polyethylene and polypropylene. The rigid portion in one embodiment is welded on both sides to a flexible sheet (not numbered). Suitable materials for include PVC, e.g., monolayer PVC films, non-DEHP PVC monolayer film, multilayer non-PVC films (wherein different layers are chosen to provide strength, weldability, abrasion resistance and minimal "sticktion" to other materials such as rigid cassette materials), polypropylene/polyethylene blend, polypropylene or Kraton blend, coextruded or laminated, with or without gas barrier, polyester, polyolefin, ULDPE.

Ports 242 (referring collectively to 242*a* to 242*h*) can be isolated from flow paths 246 (referring collectively to flow paths 246*a* to 246*i*) via valve ports 248*a* to 248*w* (referred to collectively as valve ports 248). Valve ports 248*a* to 248*w* are operated mechanically, pneumatically or combined mechanically/pneumatically as desired.

HD dialysate cassette 30*b* defines or includes four pumping portions 24*a* to 24*d*. In the illustrated embodiment, pump actuators (mechanical, pneumatic or combined) operating with pump portions 24*a* to 24*d* form high accuracy volumetric or diaphragm type pumps. In the illustrated embodiment, two pumping portions 24*a* and are provided on the front of valve and pump portion 240 of HD dialysate cassette 30*b*, while two pumping portions 24*a* and are provided on the back of valve and pump portion 240.

FIG. 15 illustrates an embodiment for blood cassette 44. Blood cassette 44 includes peristaltic pumping tube 244. Suitable materials for tubing 244 include PVC, non-DEHP PVC, norprene, silicone, pharmel, pharmapure, C-flex, viton, polybutadiene ("PB"), ethylene vinyl acetate ("EVA"), polypropylene ("PP") blend, polyethylene ("PE") blend, Kraton blend and polyolefin blends.

Peristaltic pumping tube 244 connects fluidly to a sensor portion 260, which can be made of any one or more of the rigid or sheeting materials described above. Sensor portion 260 includes a blood and air separation receptacle 262 and a pair of pressure sensor interfaces 264 and 266. Pressure sensor interfaces 264 and 266 enable arterial and venous pressures to be measured. Priming and rinseback connections 268 connect fluidly to pressure sensor interfaces 264 and 266 as illustrated.

Figure 16A:
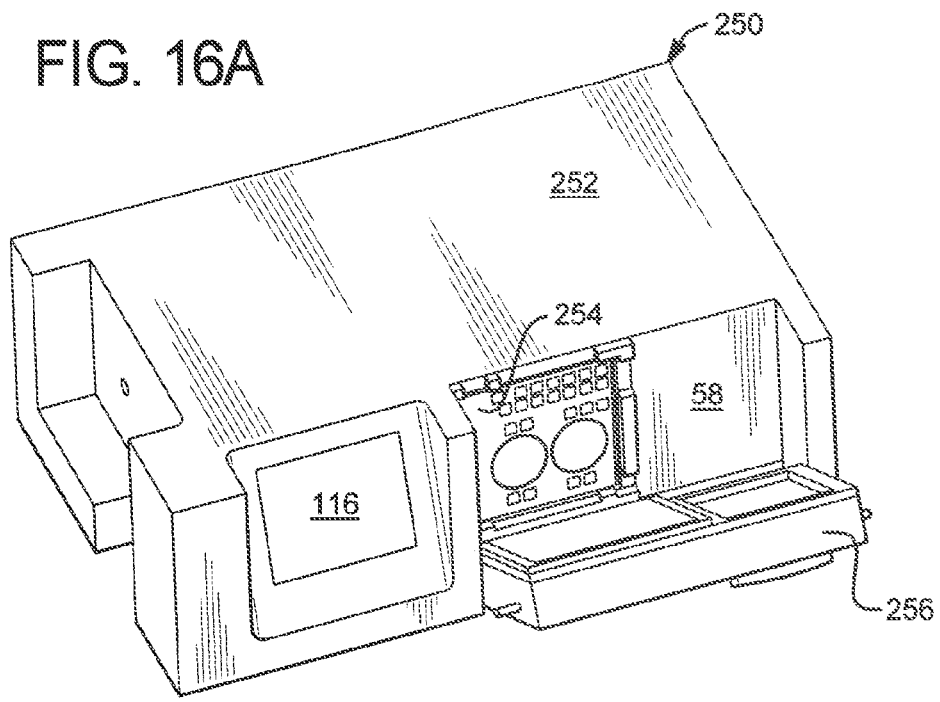
FIGS. 16A and 16B are perspective views (cassette removed and loaded, respectively) of the combined PD/HD system of FIGS. 13A and 13B, in which the blood treatment apparatus is removed so that the system is now configured for PD.
Figure 16B:
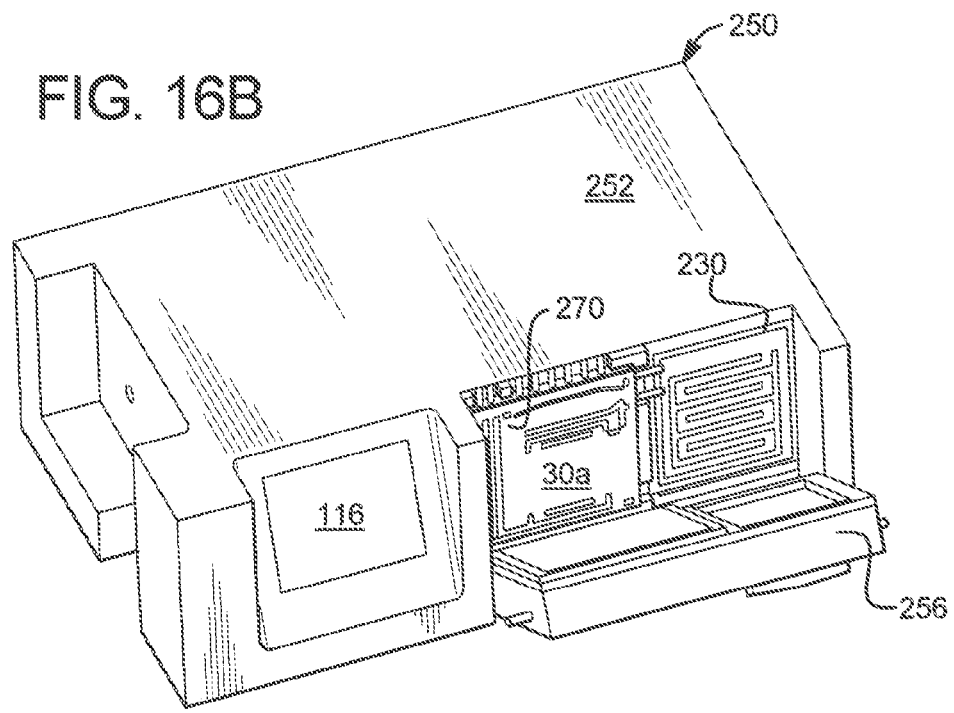

Referring now to FIGS. 16A and 16B, integrated system 250 configured for PD use is illustrated. Integrated system 250 for PD use includes many of the same apparatuses as described above for HD or blood treatment use, such as the same housing 252, same GUI 116, same cassette interface 254 and the same heater 58. As seen in FIGS. 16A and 16B however, blood pump 50 and dialyzer holder 258 are not installed. A patient performing PD only receives integrated system 250 as illustrated in FIGS. 16A and 16B. If the patient later wishes to perform HD or a blood treatment therapy, blood pump 50 and dialyzer holder 258 are installed. GUI 116 is set to run a combined PD/HD therapy regime or an HD regime only.

FIG. 16B shows PD dialysate cassette 30*a* installed into housing 252 of system 250 in the same manner as HD dialysate cassette 30*b* is installed in FIG. 13B. PD cassette 30*a* includes the same fluid heating pathway 230 as does HD dialysate cassette 30*b*. A valve and pump portion 270 of PD cassette 30*a* interfaces with cassette 254 as seen in FIG. 16B in the same manner as does valve and pump portion 240 of HD dialysate cassette 30*b*.

Figure 17A:
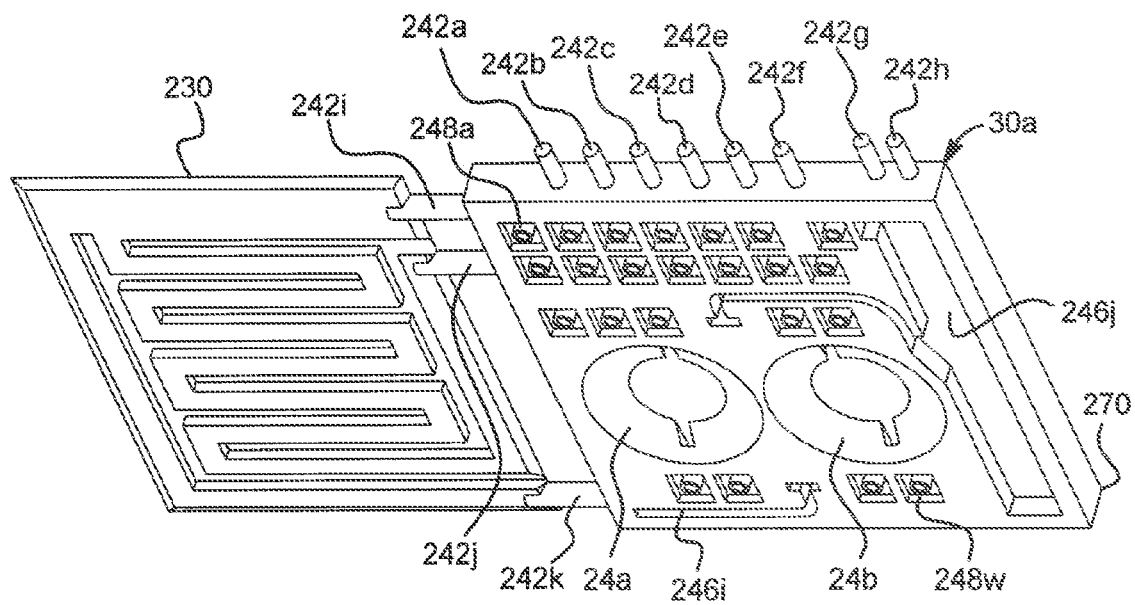
FIGS. 17A and 17B are perspective views of a PD dialysate cassette that can be loaded into the area of the PD/HD system of FIGS. 13A, 13B, 16A and 16B.
Figure 17B:
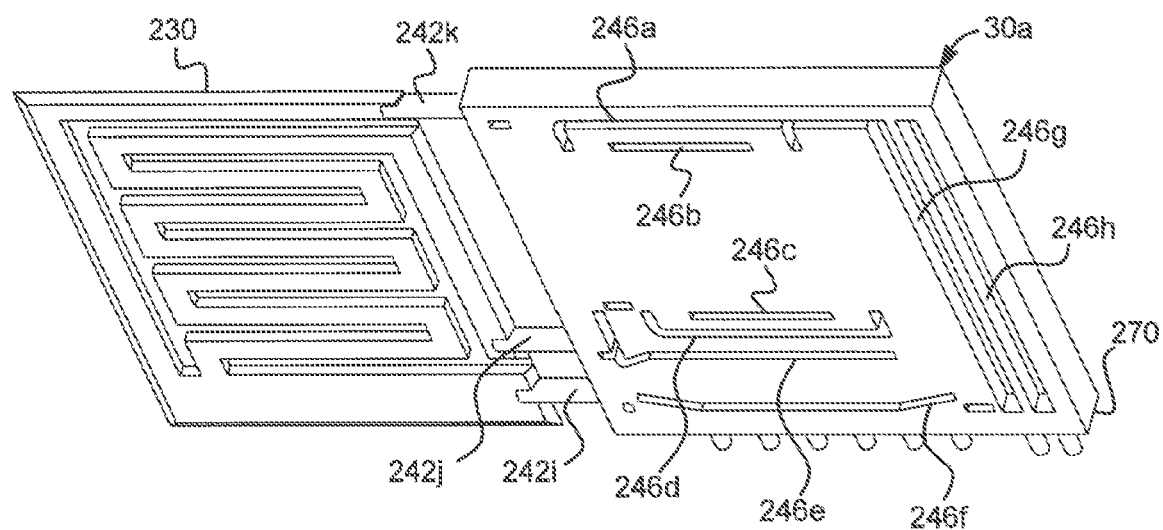

FIGS. 17A and 17B illustrate PD cassette 30*a* from two directions. Noticeably, PD cassette 30*a* includes the same fluid heating pathway 230, ports 242, pathways 246 and valve port seats 248 as does blood dialysate cassette 30*b*. These same ports, pathways and valve seats are also located in the same position for both cassettes 30*a* and 30*b*. This allows the same valve actuators within housing 252 to operate with either cassette.

FIG. 17A illustrates that volumetric pumping portions 24*a* and 24*b* are located in the same position on the same side of dialysate cassette 30*a* as those components located on blood dialysate cassette 30*b*. The primary difference between PD dialysate cassette 30*a* and HD dialysate cassette 30*b* is that the two additional pumps 24*c* and 24*d* of HD dialysate cassette 30*b* are not provided or needed with PD cassette 30*a*. A reason for this is that PD is generally a batch operation in which more fluid is removed from the patient than is pumped to the patient, the difference making up the amount of UF from the patient. Here, the same pump actuators (mechanical, pneumatic or combined) operable with pumping portions 24*a* and 24*b* perform both jobs of (i) delivering dialysate to and from the patient's peritoneum and (ii) controlling UF. However, if CFPD is performed, the two additional pumps would provide for higher flowrates.

With HD on the other hand, two pumps are dedicated to delivering dialysate to and from the dialyzer, while the other two pumps are dedicated to UF. With volumetric or diaphragm pumps, two pump actuators and pump portions are provided to alternate cycles (filling and expelling), so that a substantially constant flow of dialysate is produced. The pumps will typically operate against higher backpressure when performing HD.

Figure 18A:
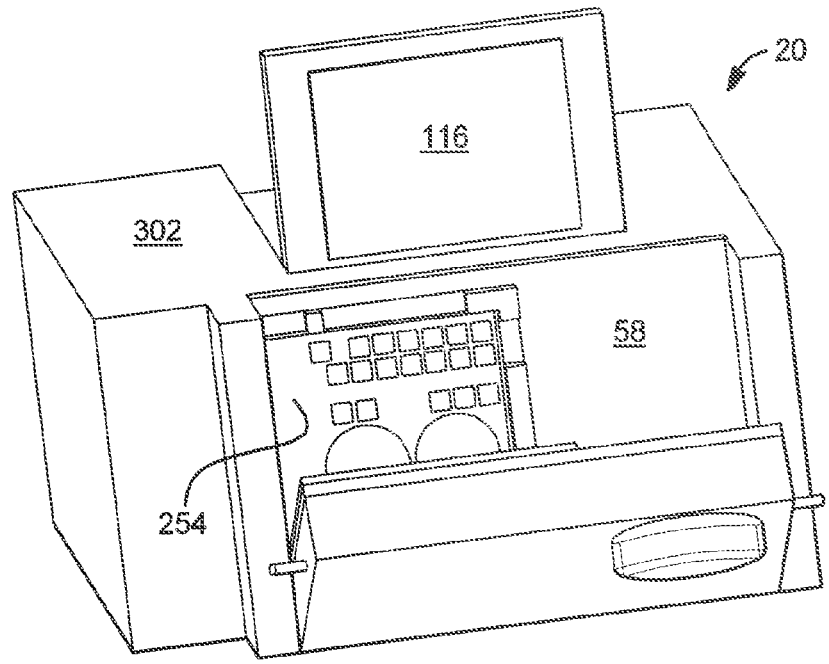
Figure 18B:
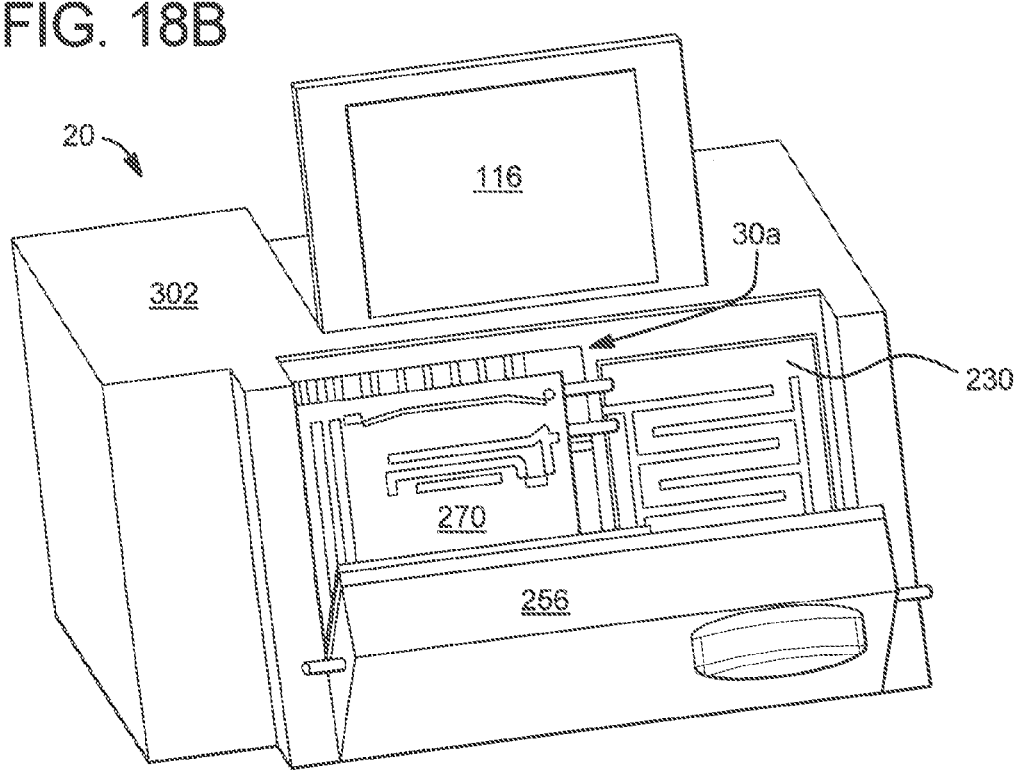
Figure 18C:
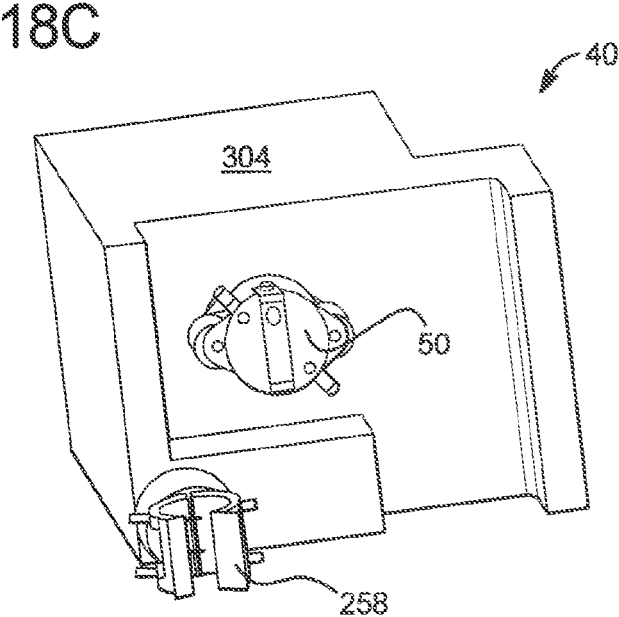
Figure 18D:
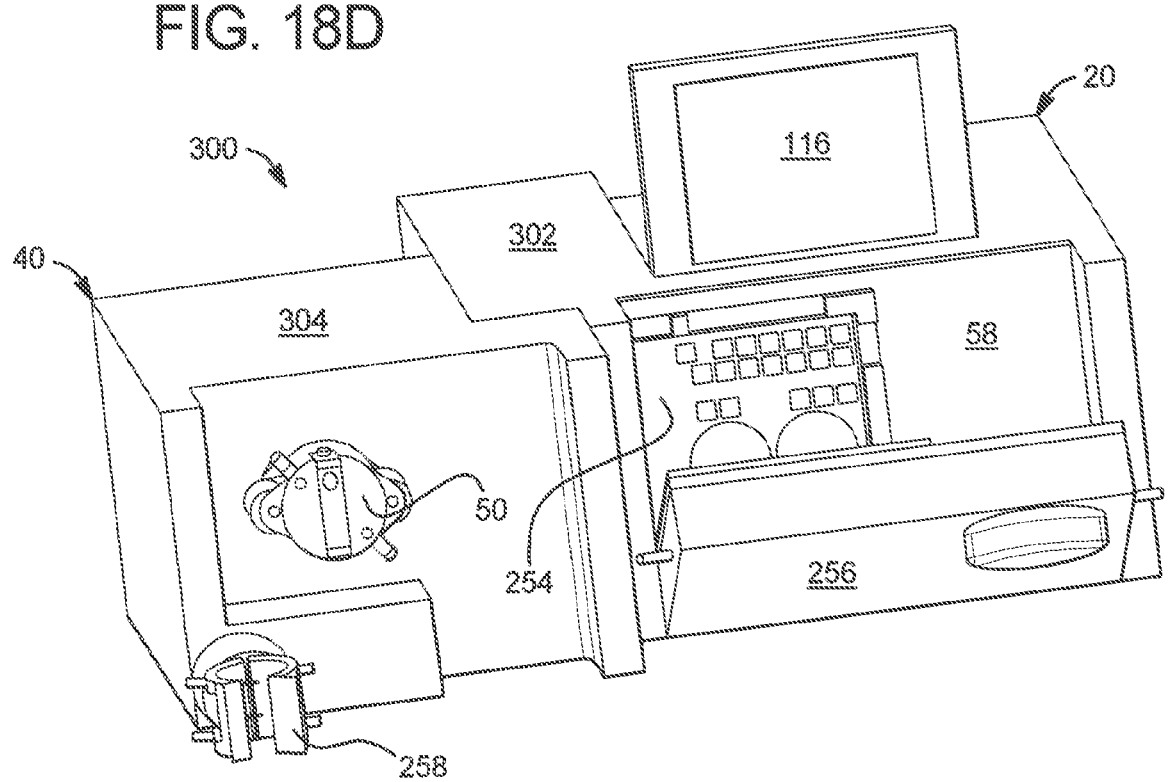

Referring now to FIGS. 18A to 18E, another embodiment for a combined PD/HD system is illustrated by system 300 (FIGS. 18D and 18E). Here, a separate HD unit 40 (FIG. 18C) is operated separate from or docked to (as seen in FIGS. 18D and 18E) dialysate unit 20 (FIGS. 18A and 18B) to form PD/HD system 300. As seen in FIG. 18E, blood cassette 44 is separated from the dialysate HD cassette 30*b*, such that the same blood cassette 44 (and associated blood pump 50) can be mounted on separate unit 40 (of FIG. 18C) or the integrated system 250 described above. Accordingly, many components of system 250 are shown again with system 300. Those components are numbered the same as above.

PD unit 20 and HD unit 40 of system 300 include housings 302 and 304, respectively. PD unit 20 includes GUI 116 (here in hinged or fold-away form) described above in connection with FIG. 12. Dialysate housing 302 includes a cassette interface 254 which interfaces interchangeably with PD dialysate cassette 30*a* and HD dialysate cassette 30*b*. Housing 302 has a hinged to door 256, which compresses PD dialysate cassette 30*a* or HD dialysate cassette 30*b* (according to whichever treatment is being performed) in place against cassette interface 254 as described in U.S. Application No. 2004/019313A1, entitled, Systems, Methods and Apparatuses for Pumping Cassette-Based Therapies and in U.S. Pat. No. 6,261,065, entitled, System and Methods for Control Of Pumps Employing Electrical Field Sensing, both of which are assigned to the eventual assignee of the present disclosure and incorporated herein by reference.

As seen in FIGS. 18B and 18E, respectively, both PD dialysate cassette 30*a* and HD dialysate cassette 30*b* include or are attached to an inline heating path 230. Hinged door 256 also compresses inline fluid heating pathway 230 against a heater 58 built into housing 302 of PD unit 20 of system 300. System 300 (and system 250) alternatively use batch heating via a warmer bag for example.

In FIGS. 18A and 18B, system 300 is configured for PD use. Here, HD unit 40 is not used. A patient performing PD only receives only dialysate unit 20 of system 300 as illustrated in FIGS. 18A and 18B. If the patient later wishes to perform HD or a blood treatment therapy, HD unit 40 including pump 50 and dialyzer holder 258 are shipped to the patient. GUI 116 senses the addition of HD unit 40 and runs a combined PD/HD therapy regime or an HD regime only. System 300 therefore has an initial hardware advantage over integrated system 250 because PD unit 20 does not have to provide the hardware and software space and support for the components of HD unit 40. For example, housing 252 of system 250 has to house each CPU and controller for both HD and PD use. Here, HD unit 40 of system 300 can house the blood pumping controllers, such that they do not have to be shipped initially with PD unit 20.

FIG. 18B shows PD dialysate cassette 30a installed into housing 302 of dialysate unit 20 in the same manner as HD dialysate cassette 30b is installed in housing 302 of FIG. 18E. PD cassette 30a includes the same fluid heating pathway 230 as does HD dialysate cassette 30b. Valve and pump portion 270 of PD cassette 30a interfaces with cassette interface 254 (FIG. 18A) in the same manner as does valve and pump portion 240 of HD dialysate cassette 30b.

PD cassette 30a includes the same fluid heating pathway 230, ports 242, pathways 246 and valve port seats 248 (FIGS. 17A and 17B) as does blood dialysate cassette 30b (FIGS. 14A and 14B). These same ports, pathways and valve seats are also located in the same position for both cassettes 30a and 30b. This allows the same valve actuators within housing 302 to operate with either cassette.

Volumetric pumping portions 24 are located in the same position on the same side of dialysate cassette 30a as those components located on blood dialysate cassette 30b. The primary difference between PD dialysate cassette 30a and HD dialysate cassette 30b, as before, is that the two additional pumps 24c and 24d on HD dialysate cassette 30b are not provided or needed with PD cassette 30a.

FIGS. 18D and 18E show system 300 configured for a blood treatment or HD use and include many of the same apparatuses as for PD use, such as the same GUI 116, same cassette interface 254 and the same heater 58 (FIG. 18D). HD unit 40 can be operated externally from PD unit 20, e.g., via wired or wireless communication, or be physically and electronically docked to PD unit 20 as seen in FIGS. 18D and 18E.

Separate HD unit 40 in FIGS. 18C and 18E includes blood pump 50 and dialyzer holder 258. As seen in FIG. 18E, dialyzer holder 258 clamps onto and holds dialyzer 42 when system 300 is to be used for a blood treatment, such as hemodialysis. FIG. 18E also shows HD or blood treatment cassette 44 installed, such that pump tubing 244 of cassette 44 is pulled around and placed in operable communication with blood pump 50.

HD disposable dialysate cassette 30b in an embodiment is the same as described above for integrated system 250. Cassette 30b includes an attached fluid heating pathway 230 as discussed above, which attaches to a valve and pump portion 240 of cassette 30b. Valve and pump portion 240 includes ports 242, flow paths 246 and valve port seats 248 as described above. HD dialysate cassette 30b defines or includes multiple pumping portions 24 as described above.

Blood cassette 44 in the embodiment illustrated in FIG. 18C is the same as described above in connection with FIG. 15. Blood cassette 44 includes peristaltic pumping tube 244. Peristaltic pumping tube 244 connects fluidly to a sensor portion 260, which can be made of any one or more of the rigid or sheeting materials described above. Sensor portion 260 includes a blood and air separation receptacle 262 and a pair of pressure sensor interfaces 264 and 266. Pressure sensor interfaces 264 and 266 enable arterial and venous pressures to be measured. Priming and rinseback connections 268 connect fluidly to pressure sensor interfaces 264 and 266 as illustrated.

Control Methodology

Referring now to FIG. 19, one sequence suitable or for implementing the various systems described above is illustrated by sequence 150. Sequence 150 applies to any mechanical configuration discussed herein. Sequence 150 also applies to any of the types of blood treatment modalities discussed herein, such as HD, HF or HDF (including HDF using separate substitution fluid and pump, HDF using the push-pull method, HDF using single needle and HDF using the dual dialyzers of FIGS. 18 and 20). For convenience, each of the different blood treatment modalities is referred to in FIGS. 19 to 22 as a blood treatment. Generally, sequence 150 enables the patient or caregiver to enter whether PD or a blood treatment is to be performed manually. In one embodiment, sequence 150 is stored in and carried out in control unit 26 of PD unit 20 at least substantially exclusively or in combination with controller 46 of blood HD 40. Again, the dialysate and blood units can be combined, in which processing and memory storage is located in a centralized processing area within the combination machine.

Upon starting sequence 150 as seen in connection with oval 152, a user interface operating with control unit 26 and/or controller 46 provides initialization information to the patient or caregiver, such as a current date and time, patient identification information, last therapy information and other desirable information. Patient data may be retrieved from a data card or other types of data storage device, which is plugged or inserted into PD unit 20 in one embodiment. Alternatively, PD unit 20 allows internet or network access, wherein patient data is retrieved from a network or internet database.

As seen in connection with block 156, the patient or caregiver enters the patient's current weight. In block 158, the patient or caregiver either enters the patient's dry weight or confirms the dry weight stored already in control unit 26 of dialysate unit 20 for example.

In sequence 150, the patient can determine which modality to use based on the patient's preference that day. Alternatively, the patient enters the type of treatment according to a schedule or calendar prescribed by a doctor or caregiver. In any case, the patient may wish to see a calendar of past treatments as determined in connection with diamond 160 to help make decision (if the patient decides on his/her own) or to see which type of treatment has been scheduled by the doctor or caregiver. If a calendar is selected in connection with diamond 160, sequence 150 causes a calendar of previous treatments including treatment type to be displayed on the user interface of PD unit 20, for example, as seen in connection with block 162.

Whether or not a calendar is shown, sequence 150 next prompts the patient to enter a therapy selection, namely a PD or blood treatment selection, as indicated in connection with diamond 164. If the patient chooses a blood treatment for example, sequence 150 determines whether there is a last bag volume of PD dialysate in the patient peritoneum, which needs to be removed, as indicated in connection with diamond 166.

In certain PD treatments, the patient is left at the end of therapy with a volume of PD dialysate in the patient's peritoneum, known as a last fill or last bag volume of dialysate. This volume stays in the patient until the next treatment, which then removes the previous last bag volume as its first step. Accordingly, if the current treatment is a blood treatment, as indicated by diamond 166, and the previous treatment was a PD treatment, which left a last bag volume in the patient, the volume would need to be removed.

It is contemplated to determined whether a last bag volume exists within the patient in a number of ways. In one way, sequence 150 relies upon the system's knowledge of the previous treatment. For example, control unit 26 of PD unit 20 may recall that the previous treatment was also a blood treatment, in which case no last fill occurred that now needs to be removed. Alternatively, controller 26 may know that the last treatment was a PD treatment, which left a last fill of liquid in the patient's peritoneum, which now needs to be removed. Alternatively, controller 26 may know that PD was performed previously but that no last bag volume was left in the patient. Based on the historical information, sequence 150 causes a determination in connection with diamond 166 to be made.

In an alternative embodiment, a device is used at the time of treatment to determine whether a last bag volume of fluid exists in the patient's peritoneum. It may be desirable not to rely on the patient to recall whether a last fill has occurred. It also may be beneficial not to rely on previous therapy information, so that first time users or users of a machine having undergone memory loss do not have to be accounted for. Accordingly, it is contemplated to plug a patient line or pressure sensing device into fluid communication with the catheter implanted in the patient's peritoneum to determine whether a last bag volume resides within it.

In another alternative embodiment the system using sequence 150 assumes that the patient is full at the beginning of treatment and attempt to drain the patient initially to empty. If no fluid is sensed, indicating that no last fill is present, the system using sequence 150, first checks to see if the patient line and/or catheter is kinked or clamped, blocking drain flow. The check can be done by attempting to push a small amount of fluid to the patient. If a pressure increase is sensed, the line or catheter is assumed to be kinked or clamped, prompting the system to post an audio, visual or audiovisual alarm. If no pressure increase is sensed the patient's peritoneum is assumed to be empty. If fluid is sensed, indicating that a last fill is present, the system using sequence 150, drains the patient until and performs either a blood treatment or PD as prescribed or desired.

If a blood treatment is chosen and no last fill volume resides within the patient's peritoneum, the system using sequence 150 causes the user interface of PD unit 20 for example to provide blood treatment setup procedure information specific to a blood treatment that does not require an additional hookup for last bag removal, as seen in connection with block 168. Upon receiving feedback that the setup procedure is complete, system 150 causes the user interface to perform the blood treatment without an additional last bag removal step, as seen in connection with block 170.

If a blood treatment is selected and a last bag volume resides within the patient's peritoneum, system 150 causes the user interface to provide blood treatment setup procedure information that includes an additional hookup for last bag removal, as seen in connection block 172. This is the hookup from cassette 30b to patient 14. Upon receiving appropriate feedback that such setup procedure has been completed, sequence 150 prompts the system to perform the blood treatment with an additional last bag removal step. Here, unlike with PD, the additional last bag removal step can be done at the beginning of treatment, concurrently with the blood treatment, at the end of the blood treatment, or any combination thereof.

At the end of the blood treatment, sequence 150 causes the system to perform a blooded treatment shutdown procedure, which includes among other things logging any necessary or desirable blood treatment data, such as volume of solution delivered and removed from the dialyzers or blood filters, amount of ultrafiltrate removed, dialysate effectiveness data, such as kT/v, blood and dialysate pressures monitored throughout therapy, any alarm conditions occurring during therapy, dialysate and blood temperature, and any other desirable information. Sequence 150 then ends as seen in connection with oval 190.

If the patient or caregiver instead selects a PD modality in connection with diamond 164, sequence 150 causes the user interface to provide a PD setup procedure and to receive feedback that PD treatment can begin, as seen in connection with block 178. The last bag or last volume issue also exists in the PD treatment portion of sequence 150 because the previous treatment could have been a blood treatment or a previous PD treatment. The type of treatment performed previously likely determines whether a last bag volume of fluid resides in the patient's peritoneum. Any of the above-mentioned apparatuses and methods for determining whether a last bag volume of fluid resides within the patient's peritoneum discussed in connection with diamond 166 is also applicable to diamond 180.

If no last bag volume exists, sequence 150 causes the machine to perform a PD treatment in which a first cycle is a fill cycle, as shown in connection block 182. Because no volume of fluid resides within the patient's peritoneum at the beginning of therapy, the patient needs to receive an initial fill volume.

On the other hand if there is a last fill volume from the previous treatment as determined in connection with diamond 180, sequence 150 causes the PD machine to perform a PD treatment in which a first cycle is a last bag removal cycle, as seen in connection with block 184.

The information shown in connection with diamond 186 is optional and therefore diamond 186 is shown in phantom. It is contemplated in an alternative embodiment that if it is known already that the subsequent therapy to the current therapy is going to be a blood treatment, then a last bag volume of PD dialysate is not delivered to the patient. In this manner, the determination in connection with diamond 166 and subsequent steps discussed in connection with blocks 172 and 174 of the blood treatment are not needed. Otherwise, the last bag volume of PD dialysate is delivered to the patient as determined in connection with diamond 186.

After treatment, sequence 150 causes PD machine to perform a PD shutdown procedure and log any necessary PD treatment data, such as volume of fluid delivered, average dialysate temperature, any alarm conditions, amount of UF removed, treatment time, number of cycles, and last bag volume, for example. Whether PD or blood treatment is selected, sequence 150 ends as seen in connection with oval 190.

Figure 20:
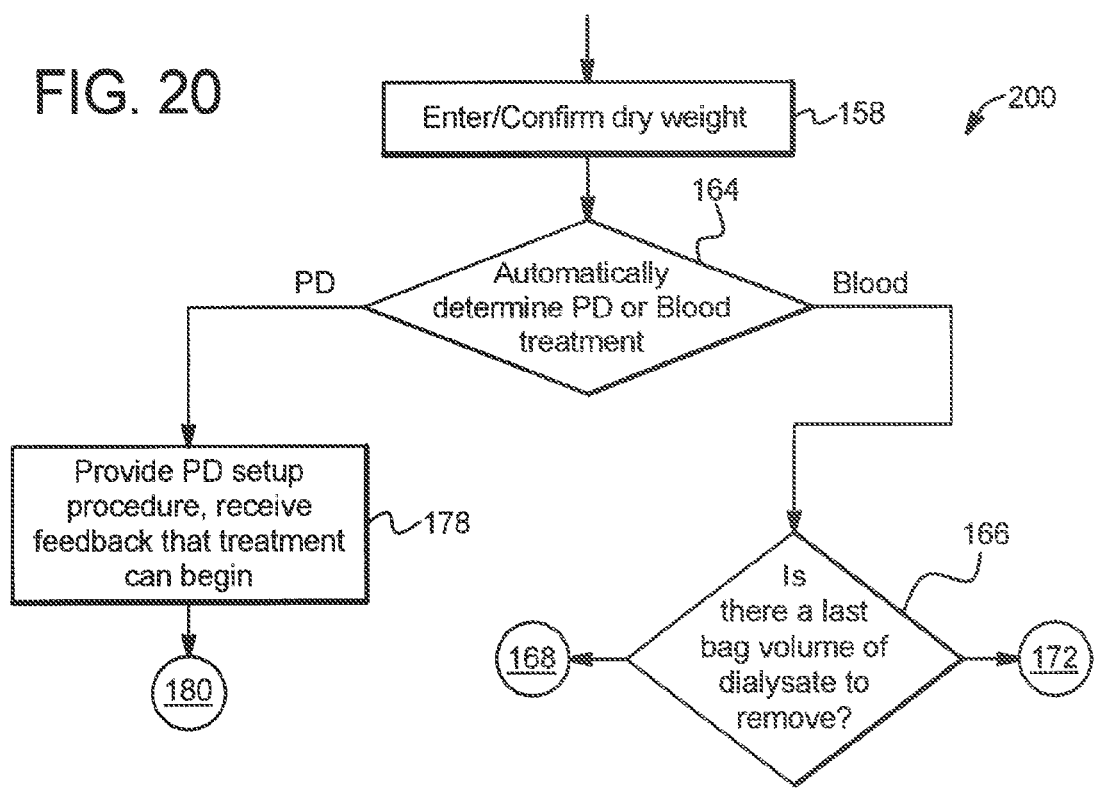
FIG. 20 is a schematic flow diagram illustrating a first alternative operational sequence for the PD/blood treatment systems described herein.

Referring now to FIG. 20, an alternative sequence in which the type of treatment is selected automatically is shown in connection with sequence 200. FIG. 20 shows the portion of sequence 200 that differs from sequence 150 of FIG. 19. Accordingly, the steps not shown do not need to be repeated but are incorporated herein by reference. At block 158 (as in sequence 150) sequence 200 causes the user interface of PD unit 20, in communication with control unit 26 for example, to prompt the patient or caregiver to enter the patient's dry weight or confirms a dry weight already known to the system. The patient's weight at the beginning of therapy and the patient's dry weight, or the weight at which the patient should weigh at the end of treatment, determine how much fluid needs to be removed from the patient in the form of UF. The volume difference between the patient's weight and dry weight is removed over the course of treatment. As discussed above, in an embodiment UF removal may be performed according to an ultrafiltrate profile, in which the ultrafiltration rate varies over time, but which has an average value that removes the required amount of UF over the total treatment time.

As seen in connection with diamond 164, system 200 automatically determines whether to perform a PD or blood treatment. In one embodiment, a message is displayed informing the patient that the current day's treatment is either a PD treatment or blood treatment. If a PD treatment, sequence 200 causes PD unit 20 to provide a PD setup procedure and receive feedback that treatment can begin as shown in connection with block 178 and described above in connection with sequence 150. Sequence 200 then continues to perform the remainder of the PD therapy beginning with the determination made in connection with step 180 as seen in FIG. 20.

If a blood therapy is chosen instead, sequence 200 determines whether there is a last bag volume of dialysate to remove as shown in connection with diamond 166 and as described above in connection with sequence 150. The remainder of blood therapy then occurs as shown in connection with steps 168 or 172 and continuing to the end of each sequence.

Controller unit 26 of PD unit 20 can store a database containing a set of therapies for particular days. Alternatively, an algorithm determines which type of therapy is to be used. For example, control unit 26 can be preset for the system to perform PD for X number of consecutive treatments, after which the system performs a blood treatment for Y number of consecutive treatments. The algorithm repeats this sequence, and X can be the same or different than Y.

Figure 21:
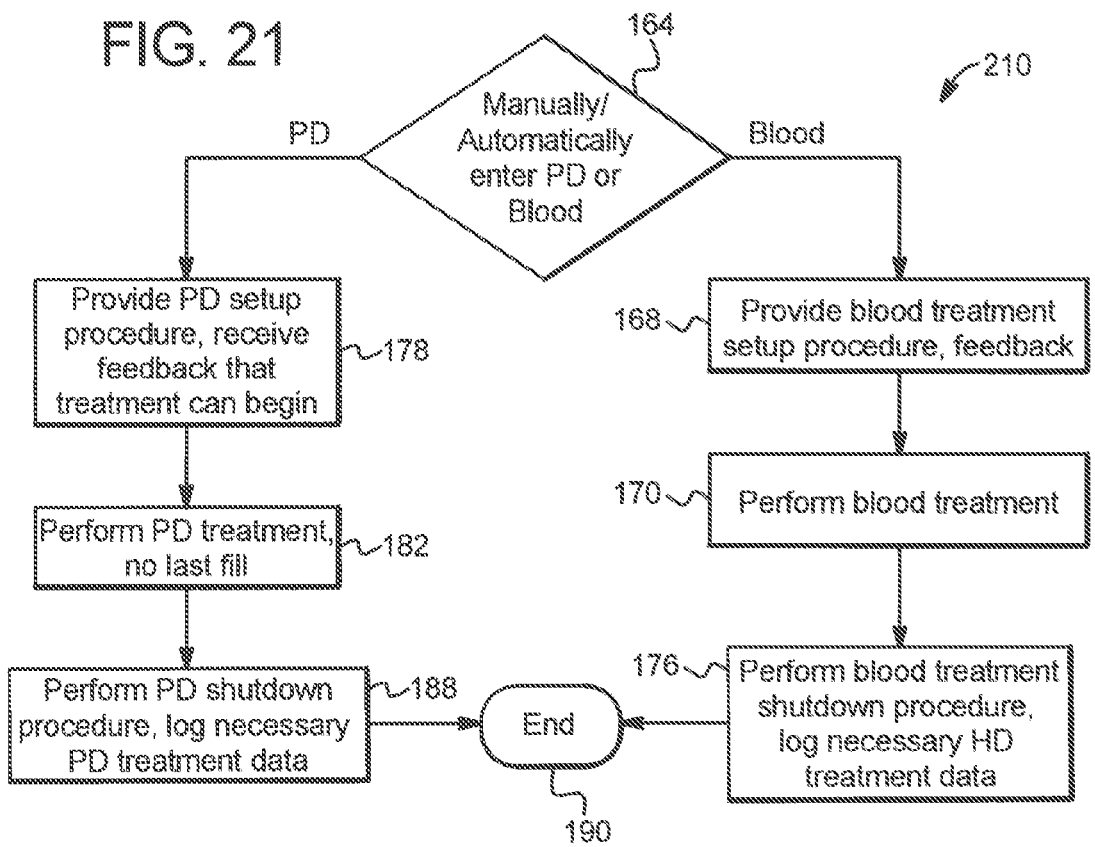
FIG. 21 is a schematic flow diagram illustrating a second alternative operational sequence for the PD/blood treatment systems described herein.

Referring now to FIG. 21, a further alternative sequence, which simplifies sequence 150 is illustrated by sequence 210. As seen in connection with diamond 164, sequence 210 can employ the manual or automatic determination of whether a PD or blood treatment is to be performed. In sequence 210, the PD treatment does not provide a last bag volume of dialysate to the patient. As seen in connection with block 178, the PD treatment provides a PD setup procedure and receives feedback that PD treatment can begin. In connection with block 182, PD unit 20 performs the PD treatment without performing a last fill, as seen in connection with block 182. Next sequence 210 causes PD unit 20 to perform a PD shutdown procedure and to log any necessary PD treatment data, examples of which are provided above as seen in step 188.

The elimination of the last bag from the PD treatment simplifies the PD and blood treatment steps because neither treatment has to take into account whether there may be a last bag volume of fluid in the patient at the beginning of the PD or blood treatment. Here, the blood treatment steps are simplified to providing a blood treatment setup procedure and receiving the appropriate feedback as discussed herein in sequence 150 shown in connection with block 168. Next, the blood treatment is performed pursuant to block 170. Afterwards, system 210 causes HD unit 40 to perform a blood treatment shutdown procedure and to log any necessary HD treatment data as described above and is shown here in connection with block 176.

Referring now to FIG. 22, yet another alternative sequence 220 is illustrated. Here, the determination of whether PD or blood treatment can be made manually or automatically as shown and described in connection with diamond 164. If PD is chosen in step 164, sequence 220 then determines whether the subsequent or next therapy will be PD or a blood treatment. Here, control unit 26 of PD unit 20 either already knows what the next treatment is going to be or the patient enters the type of next treatment upon entering the type of the current treatment. If the next therapy is a PD therapy, then system 220 causes PD unit 20 to perform a PD setup procedure including the setup of a last bag supply of dialysate, as seen in connection with block 194. Next, the PD unit 20 performs a PD procedure in which the first cycle is a last bag removed cycle and the last cycle is a last fill of PD dialysate.

Alternatively, if in connection with the determination of diamond 192 the next therapy is determined to be a blood treatment, then sequence 220 causes PD unit 20 to perform a PD setup procedure, which includes no last bag supply. Next, system 220 causes dialysate unit 20 to perform a PD procedure in which the first cycle is a last bag removal cycle and the last cycle is a removal of the last fill, meaning no last bag is provided, as seen in connection with block 198. In either case, the system performs a PD shutdown procedure and logs any necessary PD treatment data, as seen in connection with block 188. Sequence 220 then ends at step 190.

If a blood treatment is chosen instead in step 164, system 220 causes HD unit 40 to provide a blood treatment setup procedure with additional hookup to the patient for last bag removal, as seen in connection with block 172. Next, the system performs a blood treatment with an additional last bag removal step, which can occur before, during or after the blood treatment. It may that no last bag is present, and the patient knows that no last bag is present, in which case the additional hookup for last bag removal is not needed.

Finally, system 220 causes HD unit 40 to perform a blood treatment shutdown procedure, log any necessary HD treatment data as described above and shown here in connection with block 176. Next, sequence 220 ends regardless of whether PD or blood treatment is chosen, as shown in connection with oval 190.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method for peritoneal dialysis and extracorporeal blood treatments, the method comprising:
   determining, via a base unit controller, whether a peritoneal dialysis treatment or an extracorporeal blood treatment is to be performed by detecting whether a blood treatment unit is docked to a base unit of the base unit controller;

when the peritoneal dialysis treatment is to be performed, operate first software instructions that cause the base unit to use a first fluid stored in a fluid container; and when the extracorporeal blood treatment is to be performed, operate second software instructions that cause the base unit to use a second, different fluid from an online source, and selectively move the second, different fluid to the blood treatment unit for use in the extracorporeal blood treatment, the blood treatment unit being operable with the base unit to perform the extracorporeal blood treatment on a patient, the blood treatment unit including a blood pump configured to pump blood from the patient and back to the patient and a controller for controlling the blood pump, wherein the base unit controller is separate from the controller of the blood treatment unit.

2. The method of claim 1, wherein the first fluid is a peritoneal dialysis dialysate and the second fluid is an extracorporeal blood treatment dialysate.

3. The method of claim 1, wherein the second fluid is a replacement fluid.

4. The method of claim 1, wherein the blood treatment unit further includes a user interface for displaying at least one of blood pump settings or blood parameter readings.

5. The method of claim 1, wherein if the extracorporeal blood treatment is to be performed, the second software instructions additionally cause the base unit in combination with the base unit controller to:

detect blood in a dialysate return line when the blood treatment unit is docked to the base unit; and provide a notification indicative of the detected blood.

6. The method of claim 1, wherein if the extracorporeal blood treatment is to be performed, the second software instructions additionally cause the base unit in combination with the base unit controller to:

monitor sodium in dialysis fluid when the blood treatment unit is docked to the base unit; and provide a notification indicative of the monitored sodium.

7. The method of claim 1, wherein if the extracorporeal blood treatment is to be performed, the second software instructions additionally cause the base unit in combination with the base unit controller to prepare dialysis fluid using the second, different fluid from the online source, and wherein the dialysis fluid is instead selectively moved to the blood treatment unit for use in the extracorporeal blood treatment.

8. The method of claim 1, wherein the controller of the blood treatment unit is programmed to control at least one of the following: (i) air in blood detection, (ii) operational speed of the blood pump, (iii) blood line priming, (iv) blood rinseback, (v) blood line access disconnection, or (vi) valves associated with a blood treatment disposable.

9. The method of claim 1, wherein the peritoneal dialysis treatment is performed at a first time and the extracorporeal blood treatment is performed at a second time.

10. The method of claim 1, wherein the blood treatment unit includes a blood filter that receives the second, different fluid from the base unit for use in the extracorporeal blood treatment.

11. A method for peritoneal dialysis and extracorporeal blood treatments, the method comprising:

determining, via a base unit controller, whether a peritoneal dialysis treatment or an extracorporeal blood treatment is to be performed by determining whether a peritoneal dialysis unit is docked to a base unit of the base unit controller;

when the peritoneal dialysis treatment is to be performed, operate first software instructions that cause the base unit to receive, in a user interface of the peritoneal dialysis unit, user inputs related to the peritoneal dialysis treatment, use a first fluid stored in a fluid container, selectively move the first fluid to the peritoneal dialysis unit for use in the peritoneal dialysis treatment, and pump, using a dialysis fluid pump and a control unit of the peritoneal dialysis unit, the first fluid through a patient line to a peritoneal cavity of a patient for a dwell period of the peritoneal dialysis treatment according to the user inputs to perform the peritoneal dialysis treatment; and when the extracorporeal blood treatment is to be performed, operate second software instructions that cause the base unit to use a second, different fluid from an online source for the extracorporeal blood treatment, wherein the base unit controller is separate from the control unit of the peritoneal dialysis unit.

12. The method of claim 11, wherein the first fluid is a peritoneal dialysis dialysate and the second, different fluid is an extracorporeal blood treatment dialysate.

13. The method of claim 11, wherein determining the peritoneal dialysis treatment is to be performed includes performing a handshake routine between the base unit controller and the control unit of the peritoneal dialysis unit to confirm that the peritoneal dialysis unit is properly docked to the base unit.

14. The method of claim 13, wherein the base unit and the peritoneal dialysis unit are configured to share data via a wired or wireless connection.

15. The system of claim 11, wherein the user interface controls both the base unit and the peritoneal dialysis unit.

16. The method of claim 11, wherein the peritoneal dialysis treatment is performed at a first time and the extracorporeal blood treatment is performed at a second time.

* * * * *